(12) United States Patent
Yuqiu et al.

(10) Patent No.: US 6,573,368 B2
(45) Date of Patent: *Jun. 3, 2003

(54) COMPOSITIONS FOR THE TREATMENT AND DIAGNOSIS OF BREAST CANCER AND METHODS FOR THEIR USE

(75) Inventors: Jiang Yuqiu, Kent, WA (US); Davin C. Dillon, Seattle, WA (US); Jennifer L. Mitcham, Redmond, WA (US); Jiangchun Xu, Bellevue, WA (US)

(73) Assignee: Corixa Corporation, Seattle, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/339,338

(22) Filed: Jun. 23, 1999

(65) Prior Publication Data

US 2002/0102602 A1 Aug. 1, 2002

Related U.S. Application Data

(63) Continuation-in-part of application No. 09/285,480, filed on Apr. 2, 1999, which is a continuation-in-part of application No. 09/222,575, filed on Dec. 28, 1998, now Pat. No. 6,387,697.

(51) Int. Cl.$^7$ .......................... C12N 5/00; C07H 21/02; C07H 21/04
(52) U.S. Cl. .................... 536/23.1; 536/24.1; 536/24.3; 536/23.6; 435/320.1; 435/455; 435/252.3; 435/254.2
(58) Field of Search ............................... 536/23.1, 23.2, 536/23.4, 23.5, 24.1, 24.3, 24.31, 24.32, 24.33; 435/320.1, 455, 325, 243

(56) References Cited

U.S. PATENT DOCUMENTS

| | | | |
|---|---|---|---|
| 5,215,926 A | 6/1993 | Etchells, III et al. | ........ 436/501 |
| 5,240,856 A | 8/1993 | Goffe et al. | ................ 435/299 |
| 5,891,857 A | 4/1999 | Holt et al. | |
| 5,986,170 A | 11/1999 | Subjeck | ......................... 800/2 |

FOREIGN PATENT DOCUMENTS

| | | |
|---|---|---|
| WO | WO 89/06280 | 7/1989 |
| WO | WO 91/16116 | 10/1991 |
| WO | WO 92/07243 | 4/1992 |
| WO | WO 96/29430 | 9/1996 |
| WO | WO 98/21331 | 5/1998 |
| WO | WO 98/33915 | 8/1998 |
| WO | WO 98/54963 | 12/1998 |
| WO | WO 99/09155 | 2/1999 |
| WO | WO 00/08210 | 2/2000 |
| WO | WO 00/43420 | 7/2000 |
| WO | WO 00/60076 | 10/2000 |
| WO | WO 00/73801 | 12/2000 |
| WO | WO 01/37779 | 5/2001 |
| WO | WO 01/47959 | 7/2001 |

OTHER PUBLICATIONS

Russell et al. Structural features can be unconserved inproteins with similar folds. Journal of Molecular Biology, vol. 244, pp. 332–350 (1994).*
Geneseq Accession No. V41453 (May 22, 1998).*
EST Accession No. AA219147 (Feb. 7, 1997).*
GenBank Accession No. AL157387, Feb. 18, 2000.
GenBank Accession No. AC036170, Apr. 9, 2000.
Jäger, D. et al, "Identification of a Tissue–specific Putative Transcription Factor in Breast Tissue by Serological Screening of a Breast Cancer Library," *Cancer Research* 61(5): 2055–2061, Mar. 1, 2001.
GenBank Accession No. AC069200, May 24, 2000.
Sulston et al., "Toward a complete human genome sequence," *Genome Research* 8(11):1097–1108, 1998.
GenBank Accession No. AF269087, Mar. 28, 2001.
GenBank Accession No. AAK27325, Mar. 28, 2001.
Chang and Shu, "Current status of adoptive immunotherapy of cancer," *Critical Reviews in Oncology/Hematology* 22(3):213–228, Apr. 1996.
Cheever and Chen, "Therapy with cultured T cells: principles revisited," *Immunological Reviews*, 157: 177–194, 1997.
Cheever et al., "Potential uses of interleukin 2 in cancer therapy," *Immunobiol*, 172:365–382, 1986.
Cole et al., "Characterization of the functional specificity of a cloned T–cell receptor heterodimer recognizing the MART–1 melanoma antigen," *Cancer Research*, 55:748–752, Feb. 15, 1995.
Durrant L., "Cancer vaccines," *Anti–Cancer Drugs*, 8:727–733, 1997.
Eshhar Z., "Tumor–specific T–bodies: toward clinical application," *Cancer Immunol Immunother*, 45:131–136, 1997.
Hwu et al., "In vivo antitumor activity of T cells redirected with chimeric antibody/T–cell receptor genes," *Cancer Research*, 55:3369–3373, Aug. 1, 1995.
Porter–Jordan and Lippman, "Overview of the biologic markers of breast cancer," *Breast Cancer* 8:(1):73–100, Feb. 1994.
Wei et al., "Protection against mammary tumor growth by vaccination with full–length, modified human ErbB–2 DNA," *Int. J. Cancer*, 81:748–754, 1999.
GenBank Accession No. AA864891, Feb. 20, 1998.
GenBank Accession No. AA398925, Apr. 25, 1997.
Stratagene 1991 product catalog, Prime–It™ Random Labeling Kit, catalog No. 300387, p. 66.

* cited by examiner

*Primary Examiner*—Michael Borin
(74) *Attorney, Agent, or Firm*—Seed Intellectual Property Law Group PLLC

(57) ABSTRACT

Compounds and methods for the treatment and diagnosis of breast cancer are provided. The inventive compounds include polypeptides containing at least a portion of breast tumor antigen. Vaccines and pharmaceutical compositions for immunotherapy of breast cancer comprising such polypeptides, or polynucleotides encoding such polypeptides, are provided, together with polynucleotides for preparing the inventive polypeptides. The inventive polypeptides may be used to generate antibodies useful for the diagnosis and monitoring of breast cancer.

10 Claims, 1 Drawing Sheet

SYN18C6 NORTHERN BLOT

Figure 1:
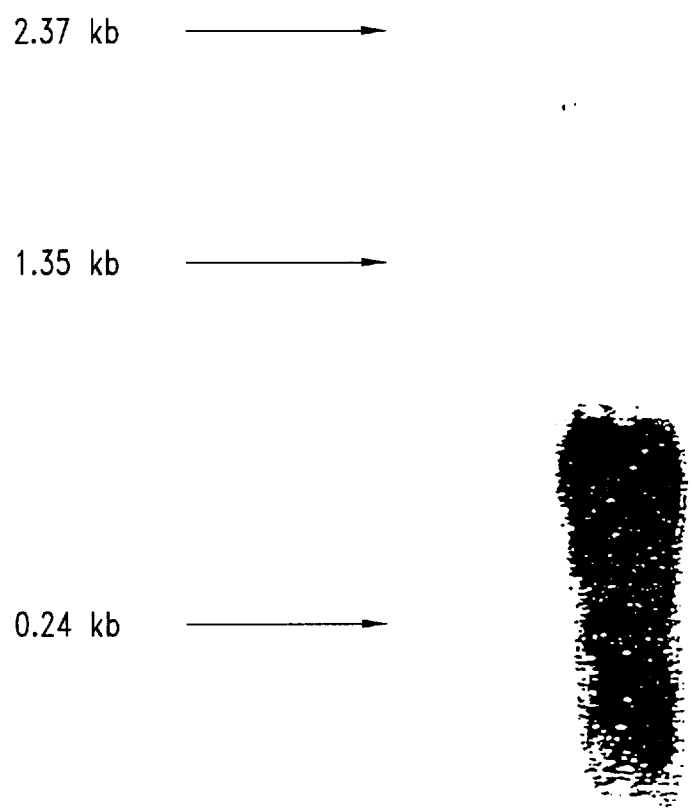

SEQUENCE LISTING

<160> NUMBER OF SEQ ID NOS: 315

<210> SEQ ID NO 1
<211> LENGTH: 281
<212> TYPE: DNA
<213> ORGANISM: Homo sapien

<400> SEQUENCE: 1

```
caatgacagt caatctctat cgacagcctg cttcatattt agctattgtt cgtattgcct      60
tctgtcctag gaacagtcat atctcaagtt caaatgccac aacctgagaa gcggtgggct     120
aagataggtc ctactgcaaa ccaccoctcc atatttccgt acgcaattac aattcagttt     180
ctgtgacatc tctttacacc actggaggaa aaatgagata ttctctgatt tattctacta     240
```

```
taacactcta catagagcta tggtgagtgc taaccacatc g                  281
```

<210> SEQ ID NO 2
<211> LENGTH: 300
<212> TYPE: DNA
<213> ORGANISM: Homo sapien

<400> SEQUENCE: 2

```
gaggtcctgg gctaacctaa tggtttatta ttggtggaga gaaagatctg gaaatacttg    60
aggttattac atactagatt agcttctaat gtgaaccatt tttcttttaa cagtgataaa   120
ttattatttc cgaagttaac tgttcccttg gtcgtgatac acactcgatt aacaaacata   180
ctgttgtatt ttttccagtt ttgtttggct atgccaccac agtcatcccc aggtctata   240 catactatgt ctcaactgta ttatttgcca tttttggcat tagaatgctt cgggaaggct   300
```

<210> SEQ ID NO 3
<211> LENGTH: 302
<212> TYPE: DNA
<213> ORGANISM: Homo sapien

<400> SEQUENCE: 3

```
ggccgaggta attggttaag tctaaagaga ttattattcc ttgatgtttg ctttgtattg    60
gctacaaatg tgcagaggta atacatatgt gatgtcgatg tctctgtctt ttttttttgtc   120 tttaaaaaat aattggcagc aactgtattt gaataaaatg atttcttagt atgattgtac   180
agtaatgaat gaaagtggaa catgtttctt tttgaaaggg agagaattga ccatttattg   240
ttgtgatgtt taagttataa cttatcgagc acttttagta gtgataactg tttttaaact   300
tg                                                                  302
```

<210> SEQ ID NO 4
<211> LENGTH: 293
<212> TYPE: DNA
<213> ORGANISM: Homo sapien

<400> SEQUENCE: 4

```
tgtaccaatc ctttggcaca agaatatgta agaactatag ttgtttttat tggttttgt    60 tcttgagatt gttttcattc tgtttttgac tgtatctctt taggaggctg aggatggcat   120
tattgcttat gatgactgtg gggtgaaact gactattgct tttcaagcca aggatgtgga   180
aggatctact tctcctcaaa tacgagataa ggcaagataa ttctgctcat tcgagagagg   240
gttaagagtt gtcatcttaa tcataaatcc tgcaggatgg gttcttcaaa ttt          293
```

<210> SEQ ID NO 5
<211> LENGTH: 275
<212> TYPE: DNA
<213> ORGANISM: Homo sapien

<400> SEQUENCE: 5

```
cgaggtttgg aatcagactt ctgtgtccag taaaaaactc ctgcactgaa gtcattgtga    60
cttgagtagt tacagactga ttccagtgaa cttgatctaa tttctttga tctaatgaat    120 gtgtctgctt accttgtctc cttttaattg ataagctcca agtagttgct aattttttga   180
caactttaaa tgagtttcat tcacttcttt tacttaatgt tttaagtata gtaccaataa   240
tttcattaac ctgttctcaa gtggtttagc tacca                              275
```

<210> SEQ ID NO 6
<211> LENGTH: 301

```
<212> TYPE: DNA
<213> ORGANISM: Homo sapien

<400> SEQUENCE: 6
gaggtctggt ttcctgggta tgcctggact gttgcccagt gtaagatctg tgcaagccat     60
attggatgga agtttacggc caccaaaaaa gacatgtcac ctcaaaaatt ttggggctta    120
acgcgatctg ctctgttgcc cacgatccca gacactgaag atgaaataag tccagacaaa    180
gtaatacttt gcttgtaaac agatgtgata gagataaagt tatctaacaa attggttata    240
ttctaagatc tgctttggaa attattgcct ctgatacata cctaagtaaa cataacatta    300
a                                                                    301

<210> SEQ ID NO 7
<211> LENGTH: 301
<212> TYPE: DNA
<213> ORGANISM: Homo sapien

<400> SEQUENCE: 7
gtccagtttg tacacagtga ttccttatgc acgccgaaag ggtttccgta aaatgacat      60 tatatacaaa tctgtacacc catccaccag agcgattctc cagctcccag agggagttat    120
caacttaaag caggatacct gaggtttcat gtctttagtt gccttatcat aatcccaaat    180
atacatttca gggtttgttt tgttttttaa agacactttc ctggaatatg tgcactatgg    240
ttaaaattaa aaacaaaagt aataaaataa aatgatcgct ggaaggactg acctccccac    300
c                                                                    301

<210> SEQ ID NO 8
<211> LENGTH: 301
<212> TYPE: DNA
<213> ORGANISM: Homo sapien

<400> SEQUENCE: 8
ctgtcctcat ctctgcaaag ttcagcttcc ttccccaggt ctctgtgcac tctgtcttgg     60
atgctctggg gagctcatgg gtggaggagt ctccaccaga gggaggctca ggggactggt    120
tgggccaggg atgaatattt gagggataaa aattgtgtaa gagccaaaga attggtagta    180
gggggagaac agagaggagc tgggctatgg gaaatgattt gaataatgga gctgggaata    240
tggctggata tctggtacta aaaagggtc tttaagaacc tacttcctaa tctcttcccc    300
a                                                                    301

<210> SEQ ID NO 9
<211> LENGTH: 301
<212> TYPE: DNA
<213> ORGANISM: Homo sapien

<400> SEQUENCE: 9
gaggtctgcc taagtagagg acaaagactt cctcctttca aggagaaact gagcccagga     60
ttggtaagtt taaggcactt aaccttgacc agctctgtag gtctggagca ttctggtccc    120
tggccgcttt caccaccagg cccttctcac ttatccacct cacatactgc cccagcattc    180
ctttggcatt gcgagctgtg acttgacaca ttttaatgac aagattgaag tagctacctt    240
gcaggataga ttttctgggg tatagggac aaaccaacag tgccatcagg tgtcttaaca     300
c                                                                    301

<210> SEQ ID NO 10
```

<211> LENGTH: 301
<212> TYPE: DNA
<213> ORGANISM: Homo sapien

<400> SEQUENCE: 10

```
ggcaggtcca acagttcttc cagttctggt cgagctttga atcgtccctt gaagtcttct      60
tcagtgtgct ccttcactga cagtctgact ccttcaggaa gactgctttg gattatttcc    120
aagaaaattt ctgcaaacgt agcactcaaa ccgctgatct gaaccactcg ctcatgggtg    180
gtaagcactg agtccaggag cattttgctg ccttggtcct gcaactgcaa cacttctatg    240
gttttggttg gcattgcata actttcctcg actttaatgg agagagattg cagaggttgt    300
g                                                                    301
```

<210> SEQ ID NO 11
<211> LENGTH: 301
<212> TYPE: DNA
<213> ORGANISM: Homo sapien

<400> SEQUENCE: 11

```
aggtctgtga ctttcaccca ggacccagga cgcagccctc cgtgggcact gccggcgcct     60
tgtctgcaca ctggaggtcc tccattacag aggcccagcg cacatcgctg cccccacaaa    120
cgttcagggg tacagccatg gcagctcctt cctctgccgt gagaaaagtg cttggagtac    180
ggtttgccac acacgtgact ggacagtgtc caattcaaat ctttcagggc agagtccgag    240
cagcgcttgg tgacagcctg tcctctcctg ctctccaaag gccctgctcc ctgtcctctc    300
t                                                                    301
```

<210> SEQ ID NO 12
<211> LENGTH: 301
<212> TYPE: DNA
<213> ORGANISM: Homo sapien

<400> SEQUENCE: 12

```
gaggtctggg attacaggca cgtgccacca cacctagcta atttttgagc atggggctca     60
aaggaactgc tctctggggc atgtcagatt tcggatttgg ggctgcacac tgatactctc    120
taagtggtgg aggaacttca tcccactgaa attcctttgg catttggggt tttgtttttc    180
tttttttcct tcttcatcct cctccttttt taaaagtcaa cgagagcctt cgctgactcc    240
accgaagaag tgcaccactg ggagccaccc cagtgccagg cgcccgtcca gggacacaca    300
c                                                                    301
```

<210> SEQ ID NO 13
<211> LENGTH: 256
<212> TYPE: DNA
<213> ORGANISM: Homo sapien

<400> SEQUENCE: 13

```
tttttttggca taaaaaacac aatgattaa tttctaaagc acttatatta ttatggcatg      60
gtttgggaaa caggttatta tattccacat aggtaattat gcagtgcttc tcatggaaaa    120
aatgcttagg tattggcctt ttctctggaa accatatttt tccttttta ataatcaact     180
aaaatgtata tgttaaaaag cctcatcttt tgattttcaa tatacaaaat gctttcttta    240
aaagaacaag attcaa                                                    256
```

<210> SEQ ID NO 14
<211> LENGTH: 301

```
<212> TYPE: DNA
<213> ORGANISM: Homo sapien

<400> SEQUENCE: 14
ggtccttgat agaggaagag gaatatccaa ggcaaagcca ccaccacgtc caacctcctc      60
atcctctacc tttcctgtcc ccagaggtat gagatagacc ccctggcctg gttcctgcac     120
tgtgctaggc ccacagtgga cacttccacc ttaatgagaa taggccccca tggagtggag     180
gtccctcctc catggcctgc aacccaatga ctatggggggt gacacaagtg acctctgccc    240
tgtgatggct caacaccatc acacgcaact gtccagacaa gccccctcaa cgggctgctg     300
t                                                                    301

<210> SEQ ID NO 15
<211> LENGTH: 259
<212> TYPE: DNA
<213> ORGANISM: Homo sapien

<400> SEQUENCE: 15
gtcttgaaag tatttattgt ttaataattc tttctcccct cagccccatc cggccactct      60
ctctttctgc ttttctgatc atcctaaagg ctgaatacat cctcctcctg tgtggaggac     120
acgaagcaat actaaaatca atacactcga tcaggtcttc atcagatacc acgtcactgt     180
gggtagagtg ctaattttca acaaatgtgg tgttcttagg gccccacaag gtagtccttt     240
ctcaaggtcg ctgggccac                                                  259

<210> SEQ ID NO 16
<211> LENGTH: 301
<212> TYPE: DNA
<213> ORGANISM: Homo sapien

<400> SEQUENCE: 16
cgaggttgtt cacattttca aataaataat actccccgta agtaataact gcaaccaatc      60
agtgttattc agtgctatgc ctccttgtaa tgggtagtta ttaattattt tcagagcttt     120
ctggaaatac tgtcctaact ggctatgttt aggatctttg ttatctctga agacaaagaa     180
agaactagga ctcttaattt tggggtgctt cttgactctt agttgggaaa ctgaaaatat     240
ttccaacctt ttacccacgt caatggcata ttctgggaat caccaccacc accaccacta     300
c                                                                    301

<210> SEQ ID NO 17
<211> LENGTH: 301
<212> TYPE: DNA
<213> ORGANISM: Homo sapien

<400> SEQUENCE: 17
gcccgggcag gtctggggcc tagggtggct ctttgcaaag ctgagggggca agctaaggaa      60
gccaggcagg tcaggggccc tttcggcctt ctcaagcctc cacctgagtt ctcgtcaatg     120
ccagtctccc tggtatgatt ggggacatta tcagagaaac atctaatagc gcacatctgg     180
gcacccacac tctgcttcag ttgcatccat cctcccaccc caaattcaac tcctgaccca     240
atacaaaaga cttttttaac caggatttct tcttgcagga aagctgactt ggaaacacgg     300
g                                                                    301

<210> SEQ ID NO 18
<211> LENGTH: 301
<212> TYPE: DNA
```

<213> ORGANISM: Homo sapien

<400> SEQUENCE: 18

| attacaggca | cgtgccacca | cacctagcta | atttttgagc | atggggctca | aaggaactgc | 60 |
| tctctgggc | atgtcagatt | tcggatttgg | ggctgcacac | tgatactctc | taagtggtgg | 120 |
| aggaacttca | tcccactgaa | attcctttgg | catttgggt | tttgttttc | tttttttcct | 180 |
| tcttcatcct | cctccttttt | taaaagtcaa | cgagagcctt | cgctgactcc | accgaagaag | 240 |
| tgcaccactg | ggaccaccc | agtgccaggc | gcccgtccag | ggacacacac | agtcttcact | 300 |
| g | | | | | | 301 |

<210> SEQ ID NO 19
<211> LENGTH: 301
<212> TYPE: DNA
<213> ORGANISM: Homo sapien

<400> SEQUENCE: 19

| agaatctctg | cactgtcatc | aggtacaaca | aaagatcaaa | ccctgtccc | gatgttaact | 60 |
| ttttaactta | aaagaatgcc | agaaaaccca | gatcaacact | ttccagctac | gagccgtcca | 120 |
| caaaggccac | ccaaaggcca | gtcagactcg | tgcagatctt | attttttaat | agtagtaacc | 180 |
| acaatacaca | gctcttaaa | gctgttcata | ttcttccccc | attaaacacc | tgccccgggc | 240 |
| ggccaagggc | gaattctgca | gatatccatc | acactggcgg | ccgctcgagc | atgcatctag | 300 |
| a | | | | | | 301 |

<210> SEQ ID NO 20
<211> LENGTH: 290
<212> TYPE: DNA
<213> ORGANISM: Homo sapien

<400> SEQUENCE: 20

| aggttttttt | tttttttttt | tttttttttt | ttttttccctt | tcaattcatt | taatttcaac | 60 |
| aatctgtcaa | aaaacagcca | ataaacaaat | actgaattac | attctgctgg | gttttttaaa | 120 |
| ggctctaaac | tataaaaaca | tcttgtgtct | cccaccctga | ccaccctgct | acttttccat | 180 |
| ataccacagg | ccacccataa | acacaaagcc | aggggtgaa | gctgacatgg | tctatttgga | 240 |
| gccagtaaac | aggagggcga | taagtcctga | taagcactta | tggacaatat | | 290 |

<210> SEQ ID NO 21
<211> LENGTH: 301
<212> TYPE: DNA
<213> ORGANISM: Homo sapien

<400> SEQUENCE: 21

| agaaaggtaa | ctgccagcca | ggcttgcatt | gtttagccag | aaattgctgc | ttggttctag | 60 |
| actcttttaaa | aaaaaaaaat | acccaggggtt | tgtcatcatt | ttcagaggca | gagtgccaaa | 120 |
| tatcacccaa | agctcttgtg | tctttttttt | acccccttat | tttattttta | tttattaatt | 180 |
| ttttgtgcaa | acatcaaatg | tcactggtgt | tcacagaagg | cttttttgac | tagccttaaa | 240 |
| ttcctgagtc | aaaagattaa | tcagattttc | aggcagtgtt | taatcaggtg | ctttgtcctg | 300 |
| t | | | | | | 301 |

<210> SEQ ID NO 22
<211> LENGTH: 301
<212> TYPE: DNA
<213> ORGANISM: Homo sapien

<400> SEQUENCE: 22

```
gacgccatgc accctccggt aaccagcagc cgcctgtcca tcccccaaga ccggaaaggc    60
agcagcagcc cccgggagcc cagggctgtc ctcggtgcat ctggctgcag agggaaattg   120
atgaccttac acagcaacta gcggccatgc agtccttcac tgacaagttc caggaccttt   180
gaagttggag ccagcgtccg gagctgcagc caagcgagtt tcctccttat cctccttagc   240
cagggctttt tctcttccgc tgcatttgcc cccttcccaa cgcaattcaa agcagttgtg   300
a                                                                  301
```

<210> SEQ ID NO 23
<211> LENGTH: 381
<212> TYPE: DNA
<213> ORGANISM: Homo sapien

<400> SEQUENCE: 23

```
cgaggtccag acagtggacc aagagatacg ctacataaat tggggtttca caattcttac    60
attatttgtc tgtcacagaa gagagctgct tatgattttg aaggggtcag ggagggtggg   120
agttggtaaa gagtagggta tttctataac agatattatt cagtcttatt cctaagatt   180
ttgttgtaac ttaaggtatc ttgctacagt agacagaatt ggtaatagca acttttaaaa   240
ttgtcattag ttctgcaata ttagctgaaa tgtagtacag aaaagaatgt acatttagac   300
atttgggttc agttgcttgt agtctgtaaa tttaaaacag cttaatttgg tacaggttac   360
acatatggac ctcccgggcg g                                             381
```

<210> SEQ ID NO 24
<211> LENGTH: 214
<212> TYPE: DNA
<213> ORGANISM: Homo sapien

<400> SEQUENCE: 24

```
aatgatgtaa aaattaatca acagggctgc cacttgcgaa tcccctccaa ggatgctgtg    60
caaagggtct cattggtcct gatgaataat cttgtgactg tacatattcc tgggtgcatg   120
tccacaaata ctgaggtata gcctgcatgc cactaaaaat aacaaaggtt tcaggggtgg   180
aaacattgtc caccacactg tcatgaccat cttt                               214
```

<210> SEQ ID NO 25
<211> LENGTH: 302
<212> TYPE: DNA
<213> ORGANISM: Homo sapien

<400> SEQUENCE: 25

```
gggggcactg agaactccct ctggaattct tgggggtgt tggggagaga ctgtgggcct    60
ggagataaaa cttgtctcct ctaccaccac cctgtaccct agcctgcacc tgtcctcatc   120
tctgcaaagt tcagcttcct tccccaggtc tctgtgcact ctgtcttgga tgctctgggg   180
agctcatggg tggaggagtc tccaccagag ggaggctcag gggactggtt gggccaggga   240
tgaatatttg agggataaaa attgtgtaag aagccaaaga aattggtagt agggggggaga   300
ac                                                                 302
```

<210> SEQ ID NO 26
<211> LENGTH: 301
<212> TYPE: DNA
<213> ORGANISM: Homo sapien

<400> SEQUENCE: 26

```
ttggagaacg cgctgacata ctgctcggcc acagtcagtg aagctgctgc atctccatta      60
tgttgtgtca gagctgcagc caggattcga atagcttcag ctttagcctt ggccttcgcc     120
agaactgcac tggcctctcc tgctgcctga tttatctgtg cagccttttc tgcttcggag     180
gccaggatct gggcctgttt cttcccttct gccacattga tggccgactc tcgggtcccc     240
tcagactcta gaactgtggc ccgtttccgc cgctctgcct ccacctgcat ctgcatagac     300
t                                                                     301
```

<210> SEQ ID NO 27
<211> LENGTH: 301
<212> TYPE: DNA
<213> ORGANISM: Homo sapien

<400> SEQUENCE: 27

```
aaatcagtca tcacatctgt gaaaagagtg ctagttataa caaatgagat cacaaatttg      60
accatttat tagacaccct ctattagtgt taacagacaa agatgaaggt taagttgaaa     120
tcaaattgaa atcatcttcc ctctgtacag attgcaatat ctgataatac cctcaacttt     180
cttggtgcaa attaattgcc tggtactcac agtccagtgt taacaggcaa taatggtgtg     240
attccagagg agaggactag gtggcaggaa aataaatgag attagcagta tttgacttgg     300
a                                                                     301
```

<210> SEQ ID NO 28
<211> LENGTH: 286
<212> TYPE: DNA
<213> ORGANISM: Homo sapien

<400> SEQUENCE: 28

```
ttttttttg cacaggatgc acttattcta ttcattctcc cccacccttc ccatatttac      60
atccttagag gaagagaggg gtaaggtgat aaagtaactg aaggaccgca agacgggtat     120
gtcccttgtt caccaaatgg tcaaagggtc aaagatcgga ggaggtcagg gggtaacgca     180
ggaacaggtg agggcgtttc gccctctctc cctctcccct tttcaacctc ttaatcactg     240
gctaactcgc gacctcatgg gttaattcgt aagcttacac gcgttg                    286
```

<210> SEQ ID NO 29
<211> LENGTH: 301
<212> TYPE: DNA
<213> ORGANISM: Homo sapien

<400> SEQUENCE: 29

```
gtcatgttct tgctcttcct tctttacaca tttgagttgt gccttctgtt cttaaagaga      60
ttttcctttg ttcaaaggat ttattcctac catttcacaa atccgaaaat aattgaggaa     120
acaggttaca tcattccaat tttgccttgg gtttgaagag tctctcatgg tggcacagtc     180
ctccagggta gctatgttgt tgggctcccc tacatcccag aagctcagag actttgtcaa     240
aggtgtgccg tccacccatt gccactgacc ctcgacaacc tggtctgaca gtccaataaa     300
a                                                                     301
```

<210> SEQ ID NO 30
<211> LENGTH: 332
<212> TYPE: DNA
<213> ORGANISM: Homo sapien

<400> SEQUENCE: 30

```
gagcagaatt gatgcctatg gctccaagtc aaatactgct aatctcattt attttcctgc    60
cacctagtcc tctcctctgg aatcacacca ttattgcctg ttaacactgg actgtgagta   120
ccaggcaatt aatttgcacc aagaaagttg agggtattat cagatattgc aatctgtaca   180
gagggaagat gatttcaatt tgatttcaac ttaaccttca tctttgtctg ttaacactaa   240
tagagggtgt ctaataaaat ggtcaaattt gtgatctcat ttgttataac tagcactctt   300
ttcacagatg tgatgactga tttccagcag ac                                 332

<210> SEQ ID NO 31
<211> LENGTH: 141
<212> TYPE: DNA
<213> ORGANISM: Homo sapien

<400> SEQUENCE: 31
aaaggctatc aagtactttg aaggacagga aggaatgaac acacccaggt ggacgtttgg    60
tttcatttgc aggggttcag ggagggttgc aggggttcag ggagggctct tgtcccacaa   120
ccgggggaag ggagagggca c                                             141

<210> SEQ ID NO 32
<211> LENGTH: 201
<212> TYPE: DNA
<213> ORGANISM: Homo sapien

<400> SEQUENCE: 32
gagctgatct cacagcacat acagaatgat gctactatgt agaccctcac tcccttggga    60
aatctgtcat ctaccttaaa gagagaaaaa agatggaaca taggcccacc tagtttcatc   120
catccaccta cataaccaac atagatgtga ggtccactgc actgatagcc agactgcctg   180
gggtaaacct tttcagggag g                                             201

<210> SEQ ID NO 33
<211> LENGTH: 181
<212> TYPE: DNA
<213> ORGANISM: Homo sapien

<400> SEQUENCE: 33
tttcaaaaca ctcatatgtt gcaaaaaaca catagaaaaa taaagtttgg tgggggtgct    60
gactaaactt caagtcacag acttttatgt gacagattgg agcagggttt gttatgcatg   120
tagagaaccc aaactaattt attaaacagg atagaaacag gctgtctggg tgaaatggtt   180
c                                                                   181

<210> SEQ ID NO 34
<211> LENGTH: 151
<212> TYPE: DNA
<213> ORGANISM: Homo sapien

<400> SEQUENCE: 34
atgtcctgca cagtatagct tggacctctg ggcctgaacc agggtgagca tcaaggcccc    60
catttctcct caccacgggg tcgcttgtca gctccaagaa ccagtctggc cccactgaga   120
acttttcagt cgagggcctg atgaatcttg g                                  151

<210> SEQ ID NO 35
<211> LENGTH: 291
<212> TYPE: DNA
<213> ORGANISM: Homo sapien
```

-continued

```
<400> SEQUENCE: 35
tctttagggc aaaatcatgt ttctgtgtac ctagcaatgt gttcccattt tattaagaaa      60
agctttaaca cgtgtaatct gcagtcctta acagtggcgt aattgtacgt acctgttgtg     120
tttcagtttg ttttcacct ataatgaatt gtaaaaacaa acatacttgt ggggtctgat      180
agcaaacata gaaatgatgt atattgtttt tgttatcta tttatttca tcaatacagt       240 attttgatgt attgcaaaaa tagataataa tttatataac aggttttctg t              291

<210> SEQ ID NO 36
<211> LENGTH: 201
<212> TYPE: DNA
<213> ORGANISM: Homo sapien

<400> SEQUENCE: 36
ctgatacaat tataataacg gttccctgaa ccttttagag tgcaattaag aacaaaaact     60
aaattttgtt tacatgaata tggaataaat acaataatca aaatatgact ctccctaaaa    120
gtgaaacaca caagccaatc cggaactgct gtgcgaaaga taaaatcgag aaaggcaagg    180
tttcggtagg aggacgcgat g                                               201

<210> SEQ ID NO 37
<211> LENGTH: 121
<212> TYPE: DNA
<213> ORGANISM: Homo sapien

<400> SEQUENCE: 37
catcacactg gcggccgctc gagcatgcat ctagagggcc caattcgccc tataatgagt     60
cgtattacaa ttcactggcc gtcgttttac aacgtcgtga ctgggaaaac cctggcgtta    120
c                                                                     121

<210> SEQ ID NO 38
<211> LENGTH: 200
<212> TYPE: DNA
<213> ORGANISM: Homo sapien

<400> SEQUENCE: 38
aaacatgtat tactctatat ccccaagtcc tagagcatga cctgcatgtt ggagatgttg     60
tacagcaatg tatttatcca gacatacata tatgatattt agagacacag tgattctttt   120
gataacacca cacatagaac attataatta cacacaaatt tatggtaaaa gaattaatat   180
gctgtctggt gctgctgtta                                                200

<210> SEQ ID NO 39
<211> LENGTH: 760
<212> TYPE: DNA
<213> ORGANISM: Homo sapien

<400> SEQUENCE: 39
gcgtggtcgt cggccgaggt cctgggctag acctaatggt ttattattgg tggagagaaa     60
gatctggaaa tacttgaggt tattacatac tagattagct tctaatgtga accattttttc   120 ttttaacagt gatcaaatta ttatttcgaa gttaatcgtt cccttggtgg ctgcatacac    180
atcgcattaa caaacatact gttgtatttt ttcccagttt tgtttggcta tgccaccaca    240
gtcatcccca gggtctatac atactatgtt tcaactgtat tatttgccat ttttggcatt    300
agaatgcttc gggaaggctt aaagatgagc cctgatgagg tcaagagga actggaagaa    360 gttcaagctg aattaaagaa gaaagatgaa gaagtaagcc atggcactgt tgatctggac   420
```

```
caaaaaggca ctcaactagg aataaacact ctacagaggt ttctcagtgg ccccatctgt      480
gtgatatgcg gggctacaca aaaatagctt cttttgcttt gttctgttct tatacctgtc      540
tgtgatctga cttggggttg gtgtgaatgt agtagagaaa ggaagctgac agatgaatac      600
tgaacacagg taatcagttt ccttaattag gttgattata agctcctgaa aagcaggaac      660
tgtattttat aattttacct gtttctcccg tggtgtctag gatagtaagt gagcagagca      720
gtaaatactg tttggtttgt tcagacctgc ccgggcggcc                             760

<210> SEQ ID NO 40
<211> LENGTH: 452
<212> TYPE: DNA
<213> ORGANISM: Homo sapien

<400> SEQUENCE: 40
aatcactaaa gatattgact agagaatgct gtgtgctatt tcaattacat ttgttttct        60 tttattaaca ggaattttga ttcttcaagg aagtggctca atttcaattt caggtgacca      120
ggtttatcgt gacttttcct tcttgtttac ttttcgctag aaggggagt tgtaggggca       180 gattcaggta ttggaatagg aaaattacgt ctaaaccatg gaaatcttgg aaatggaatt      240
ggtggaagtg ggcgaaatgg atatgggtaa gggaacacaa aaaaccctga agctaattca      300
tcgctgtcac tgatacttct tttttctcgt tcctggtctt gagagactgg gaaaccaaca      360
gccactgcca gatggctgtg atcaggagg agaactttct tcatctcaaa cgtttcagtc       420 agttcttct ctcacctcgg ccgcgaccac gc                                     452

<210> SEQ ID NO 41
<211> LENGTH: 676
<212> TYPE: DNA
<213> ORGANISM: Homo sapien

<400> SEQUENCE: 41
aatctttgaa tgccaagtct cttctgtact ttcttttatt aacatcatag tctttgcatc        60
aagatacata gcaatgatag caggtttctt tttaaagctt agtattaata ttaaatattt      120
ttccccattt aaattttaca ttacttgcca agaaaaaaaa aaaattaaaa ctcaagttac      180
ttgaagcctg gacacacttc catgattagc cgggctaggt aaaagttggt ggctttattc      240
ttcctgctct ataagcagat ccaggcccta gaaagatggg accagggtat ataattgttt      300
ttgaaaagtg tgctacaaaa atggatggcc tgttataagc caggatacaa agttaaggat      360
gggggtaagg gagggacatt ttcttccaga agaaaagaca gaatttctga agagtcccag      420
tccataattt tcccaaaatg gttggaggag agggtaaaat ctcaacatga gtttcaaagt      480
actgtctctg tgaggggccg gtagatgcct tgctgaggag ggatggctaa tttggaccat      540
gccccatccc cagctaggag aatggaaatg gaaactttaa ttgcccagtg ggtgtgaaag      600
tgggctgaag cttggttggt actgaattct ctaagaggtt tcttctagaa acagacaact      660
cagacctgcc cgggcg                                                      676

<210> SEQ ID NO 42
<211> LENGTH: 468
<212> TYPE: DNA
<213> ORGANISM: Homo sapien

<400> SEQUENCE: 42
agcgtggtcg cggccgaggt ttggccggga gcctgatcac ctgccctgct gagtcccagg       60
```

| | |
|---|---|
| ctgagcctca gtctccctcc cttggggcct atgcagaggt ccacaacaca cagatttgag | 120 |
| ctcagccctg gtgggcagag aggtagggat ggggctgtgg ggatagtgag gcatcgcaat | 180 |
| gtaagactcg ggattagtac acacttgttg attaatggaa atgtttacag atccccaagc | 240 |
| ctggcaaggg aatttcttca actccctgcc cccagccct ccttatcaaa ggacaccatt | 300 |
| ttggcaagct ctatgaccaa ggagccaaac atcctacaag acacagtgac catactaatt | 360 |
| aaaacccct gcaaagccca gcttgaaacc ttcacttagg aacgtaatcg tgtccctat | 420 |
| cctacttccc cttcctaatt ccacagacct gcccgggcgg ccgctcga | 468 |

<210> SEQ ID NO 43
<211> LENGTH: 408
<212> TYPE: DNA
<213> ORGANISM: Homo sapien

<400> SEQUENCE: 43

| | |
|---|---|
| atcatatcaa aacactatct tcccatctgt ttctcaatgc ctgctacttc ttgtagatat | 60 |
| ttcatttcag gagagcagca gttaaacccg tggattttgt agttaggaac ctgggttcaa | 120 |
| acctctttcc actaattggc tatgtctctg gacagttttt ttttttttt tttttttaa | 180 |
| accctttctg aactttcact ttctatggct acctcaaaga attgttgtga ggcttgagat | 240 |
| aatgcatttg taaagggtct gccagatagg aagatgctag ttatggattt acaaggttgt | 300 |
| taaggctgta agagtctaaa acctacagtg aatcacaatg catttacccc cactgacttg | 360 |
| gacataagtg aaaactagcc cgaagtctct ttttcaaatt acttacag | 408 |

<210> SEQ ID NO 44
<211> LENGTH: 160
<212> TYPE: DNA
<213> ORGANISM: Homo sapien

<400> SEQUENCE: 44

| | |
|---|---|
| tggtcgcggc cgaggtcttg tgtgccctgt ggtccagggg accaagaaca acaagatcca | 60 |
| ctctctgtgc tacaatgatt gccacttctc acgcaacact ccaaccagga ctttcaacta | 120 |
| caacttctcc gctttggcaa acaccgtcac tcttgctgga | 160 |

<210> SEQ ID NO 45
<211> LENGTH: 231
<212> TYPE: DNA
<213> ORGANISM: Homo sapien

<400> SEQUENCE: 45

| | |
|---|---|
| cgagcggccg cccgggcagg tctggggagg tgattccatc cagagtcata tctgttgtca | 60 |
| ccccaataag tcgatcagca aggctgacag gctgtgagga aaccccggcc ttgtagcctg | 120 |
| tcacctctgg ggggatgatg actgcctggc agacgtaggc tgtgatagat ttgggagaaa | 180 |
| acctgactca ccctcaggaa tccggaggtc ggtgacattg tcggtgcaca c | 231 |

<210> SEQ ID NO 46
<211> LENGTH: 371
<212> TYPE: DNA
<213> ORGANISM: Homo sapien

<400> SEQUENCE: 46

| | |
|---|---|
| cccgggcagg tctgtgtaac atgccaaggc tttgcacttt ctgcagagca gttttttatt | 60 |
| ttccttatca ggtacaggtt ttggtttttc ttgactatct ctgatgaatt tttcatgagt | 120 |
| ctgtatatgc agaatctttt ccctaaatac tgcttcgtcc catgtctgaa ggcgtaaaat | 180 |

-continued

```
aaagtcattc atcattttt ctttgtacat gtttatttgt tctttttcaa ttacaccaag      240
cattactagt cagaaggaag cacttgctac ctcttgctct tcctctgcct ctggtttgga      300
tcattttgat gacattgccc acattactca tgaaggatga caagattgca ctgtgcaatg      360
tcaattgcct t                                                          371
```

<210> SEQ ID NO 47
<211> LENGTH: 261
<212> TYPE: DNA
<213> ORGANISM: Homo sapien

<400> SEQUENCE: 47

```
gccctgtttt tatacacttc acatttgcag aaatataatg atgccctcat tatcagtgag       60
catgcacgaa tgaaagatgc tctggattac ttgaaagact tcttcagcaa tgtccgagca      120
gcaggattcg atgagattga gcaagatctt actcagagat ttgaagaaaa gctgcaggaa      180
ctagaaagtg tttccaggga tcccagcaat gagaatccta aacttgaaga cctctgcttc      240
atcttacaag aagagtacca c                                               261
```

<210> SEQ ID NO 48
<211> LENGTH: 701
<212> TYPE: DNA
<213> ORGANISM: Homo sapien

<400> SEQUENCE: 48

```
cgagcggccc ccgggcaggt ccaattagta caagtctcat gatataatca ctgcctgcat       60
acatatgcac agatccagtt agtgagtttg tcaagcttaa tctaattggt taagtctcaa      120
agagattatt attcttgatg tttgctttgt attggctaac aaatgtgcag aggtaataca      180
tatgtgatgt ccgatgtctc tgtcttttt tttgtcttta aaaataatt ggcagcaact       240 gtatttgaat aaaatgattt cttagtatga ttgtaccgta atgaatgaaa gtggaacatg      300 tttcttttg aaagggagag aattgaccat ttattattgt gatgtttaag ttataactta      360
ttgagcactt ttagtagtga taactgtttt taaacttgcc taatacccttt cttgggtatt     420 gtttgtaatg tgacttattt aaccccctt tttgtttgtt taagttgctg ctttaggtta      480
acagcgtgtt ttagaagatt taaattttt tcctgtctgc acaattagtt attcagagca      540
agagggcctg attttataga agccccttga aaagaggtcc agatgagagc agagatacag      600
tgagaaatta tgtgatctgt gtgttgtggg aagagaattt caatatgta actacggagc      660 tgtagtgcca ttagaaactg tgaatttcca aataaatttg a                         701
```

<210> SEQ ID NO 49
<211> LENGTH: 270
<212> TYPE: DNA
<213> ORGANISM: Homo sapien

<400> SEQUENCE: 49

```
agcggccgcc cgggcaggtc tgatattagt agctttgcaa ccctgataga gtaaataaat       60
tttatgggcg ggtgccaaat actgctgtga atctatttgt atagtatcca tgaatgaatt      120
tatggaaata gatatttgtg cagctcaatt tatgcagaga ttaaatgaca tcataatact      180
ggatgaaaac ttgcatagaa ttctgattaa atagtgggtc tgtttcacat gtgcagtttg      240
aagtatttaa attaaccact cctttcacag                                      270
```

<210> SEQ ID NO 50

<211> LENGTH: 271
<212> TYPE: DNA
<213> ORGANISM: Homo sapien

<400> SEQUENCE: 50

| | | |
|---|---|---|
| atgcatttat ccatatgaac ttgattattc tgaattactg actataaaaa ggctattgtg | 60 |
| aaagatatca cactttgaaa cagcaaatga attttcaatt ttacatttaa ttataagacc | 120 |
| acaataaaaa gttgaacatg cgcatatcta tgcatttcac agaagattag taaaactgat | 180 |
| ggcaacttca gaattatttc atgaagggta caaacagtct ttaccacaat tttcccatgg | 240 |
| tcttatcctt caaaataaaa ttccacacac t | 271 |

<210> SEQ ID NO 51
<211> LENGTH: 241
<212> TYPE: DNA
<213> ORGANISM: Homo sapien

<400> SEQUENCE: 51

| | | |
|---|---|---|
| tggtcgcggc cgaggtgtga ggagatgaac tttgtgttaa tgggggggcac tttaaatcga | 60 |
| aatggcttat ccccaccgcc atgtaagtta ccatgcctgt ctcctccctc ctacacattt | 120 |
| ccagctcctg ctgcagttat tcctacagaa gctgccattt accagccctc tgtgattttg | 180 |
| aatccacgag cactgcaggc cctccacagc gttactaccc agcaggcact cagctcttca | 240 |
| t | 241 |

<210> SEQ ID NO 52
<211> LENGTH: 271
<212> TYPE: DNA
<213> ORGANISM: Homo sapien

<400> SEQUENCE: 52

| | | |
|---|---|---|
| tccaagactt aaaacttagg aaacacctat gatgccactt taactggaag taatggagac | 60 |
| atctgattcc aaattcacat tttaaatgcc tatttgcaat cagcaaagag ccaggtatgc | 120 |
| tgcatgctgc ttgctgtaag ttacgatttg gcttcactag ctcaaatttt ttcactccac | 180 |
| caaaagataa ggcacaggcc cgtttgtcca atcaagtttg ctgaaaatac tgcagcctga | 240 |
| gtgtagacaa acttcccctg aatttgctag a | 271 |

<210> SEQ ID NO 53
<211> LENGTH: 493
<212> TYPE: DNA
<213> ORGANISM: Homo sapien

<400> SEQUENCE: 53

| | | |
|---|---|---|
| ttagcgtggt cgcggtccga ggtctggcct gactagctca ctctgaagag tgtctttcac | 60 |
| atggattaac caaaaaatgc attactgcct ttggcacact gtcttgaata ttctttctga | 120 |
| caatgagaaa atatgattta atggagtcgt tcaataacct cacaatctcg ctgttccgag | 180 |
| cagatagttt tcgtgccaac aggaactggc acatctagca ggttcacggc atgacctttt | 240 |
| tgtggactgg ctggcataat tggaatgggt tttgattttt cttctgctaa taactcttca | 300 |
| agcttttgaa gttttcaagc attcctctcc agttgcctgt ggttggttct tgaacaccat | 360 |
| ctccaacccc accacctcca gatgcaacct tgtctcgtga tacagacctg cccgggcggc | 420 |
| cctcaagggc gaattctgca gatatccatc acactggcgg ccgctcgagc atgcatctag | 480 |
| agggcccaat tcg | 493 |

<210> SEQ ID NO 54
<211> LENGTH: 321
<212> TYPE: DNA
<213> ORGANISM: Homo sapien

<400> SEQUENCE: 54

```
cgtggtcgcg gccgaggtct gtttgcttgt tggtgtgagt ttttcttctg gagactttgt      60
actgaatgtc aataaactct gtgattttgt taggaagtaa aactgggatc tatttagcca     120
ctggtaagct tctgaggtga aggattcagg acatctcgt ggaacaaaca ctccccactg      180
gactttctct ctggagatac ccttttgaat atacaatggc cttggctcac taggtttaaa     240
tacaaacaag tctgaaaccc actgaagact gagagattgc agcaatattc tctgaattag     300
gatcgggttc cataactcta a                                               321
```

<210> SEQ ID NO 55
<211> LENGTH: 281
<212> TYPE: DNA
<213> ORGANISM: Homo sapien

<400> SEQUENCE: 55

```
ttgcaaatga aactgtggat gtataataag aaaacacaag ggtttattct taacactaaa      60
attaacatgc cacacgaaga ctgcattaca gctctctgtt tctgtaatgc agaaaaatct     120
gaacagccca ccttggttac agctagcaaa gatggttact tcaaagtatg gatattaaca     180
gatgactctg acatatacaa aaaagctgtt ggctggacct gtgactttgt tggtagttat     240
cacaagtatc aagcaactaa ctgttgtttc tccgaagatg g                         281
```

<210> SEQ ID NO 56
<211> LENGTH: 612
<212> TYPE: DNA
<213> ORGANISM: Homo sapien

<400> SEQUENCE: 56

```
gcgtggtcgc ggccgaggtc ctgtccgggg gcactgagaa ctccctctgg aattcttggg      60
gggtgttggg gagagactgt gggcctggag ataaaacttg tcctctctac caccaccctg     120
taccctagcc tgcacctgtc ctcatctctg caaagttcag cttccttccc caggtctctg     180
tgccactctg tcttggatgc tctggggagc tcatgggtgg aggagtctcc accagaggga     240
ggctcagggg actggttggg ccagggatga atatttgagg gataaaaatt gtgtaagagc     300
caaagaattg gtagtagggg gagaacagag aggagctggg ctatgggaaa tgatttgaat     360
aatggagctg ggaatatggc tggatatctg gtactaaaaa aggtctttta agaacctact     420
tcctaatctc ttccccaatc caaaccatag ctgtctgtcc agtgctctct tcctgcctcc     480
agctctgccc caggctcctc ctagactctg tccctgggct agggcagggg aggagggaga     540
gcagggttgg gggagaggct gaggagagtg tgacatgtgg ggagaggacc agacctgccc     600
gggcggccgt cg                                                         612
```

<210> SEQ ID NO 57
<211> LENGTH: 363
<212> TYPE: DNA
<213> ORGANISM: Homo sapien

<400> SEQUENCE: 57

```
gtcgcggccg aggtcctgag cgtcacccta gttctgcccc ttttagctg tgtagacttg       60
gacaagacat ttgacttccc tttctccttg tctataaaat gtggacagtg gacgtctgtc     120
```

-continued

```
acccaagaga gttgtgggag acaagatcac agctatgagc acctcgcacg gtgtccagga    180
tgcacagcac aatccatgat gcgttttctc cccttacgca ctttgaaacc catgctagaa    240
aagtgaatac atctgactgt gctccactcc aacctccagc gtggatgtcc ctgtctgggc    300 ccttttctg ttttttattc tatgttcagc accactggca ccaaatacat tttaattcac    360
cga                                                                  363
```

<210> SEQ ID NO 58
<211> LENGTH: 750
<212> TYPE: DNA
<213> ORGANISM: Homo sapien

<400> SEQUENCE: 58

```
cgtggtcgcg gccgaggtct aattccacct gactggcaga acctgcgccc ctcgcctaac    60
ctgcgccctt ctcccaactc gcgtgcctca cagaacccag gtgctgcaca gccccgagat    120
gtggcccttc ttcaggaaag agcaaataag ttggtccaag tacttgatgc ttaaggaata    180
cacaaaggtg cccatcaagc gctcagaaat gctgagagat atcatccgtg aatacactga    240
tgtttatcca gaaatcattg aacgtgcatg ctttgtccta gagaagaaat ttgggattca    300
actgaaagaa attgacaaag aagaacacct gtatattctc atcagtaccc ccgagtccct    360
ggctggcata ctgggaacga ccaaagacac acccaagctc ggtctcttct tggtgattct    420
gggtgtcatc ttcatgaatg caaccgtgc cagtgaggct gtcttttggg aggcactacg    480
caagatggga ctgcgtcctg gggtgagaca tcccctcct tggagatcta aggaaacttc    540
tcacctatga gtttgtaaag cagaaatacc tggactacag acgagtgccc aacagcaacc    600
ccccggagta tgagttcctc tggggcctcc gtccctacca tgagactagc aagatgaaaa    660
tgctgagatt cattgcagag gttcagaaaa gagaccctcg tgactggact gcacagttca    720
tggaggctgc agatgaggac ctgcccgggc                                    750
```

<210> SEQ ID NO 59
<211> LENGTH: 505
<212> TYPE: DNA
<213> ORGANISM: Homo sapien

<400> SEQUENCE: 59

```
tggccgcccg ggcaggtcca gtctacaagc agagcactct catggggagc accagatgag    60
ttccagccgc agttctttta taagctttaa gtgcctcatg aagacgcgag gatctcttcc    120
aagtgcaacc tggtcacatc agggcacatt cagcagcaga gtctgtttc cagtatagtc    180 cttggtatgg ctaaattcca ctgtcccttt ctcagcagtc aataatccat gataaattct    240
gtacaacact gtagtcaata acagcagcac cagacagcat attaattctt ttaccataaa    300
tttgtgtgta attataatgt tctatgtgtg gtgttatcaa agaatcact gtgtctctaa    360 atatcatata tgtatgtctg gataaataca ttgctgtaca acatctccaa catgcaggtc    420
atgctctaag acttggggat atagagtaat acatgtttcg tggacctcgg ccgcgaccac    480
gctaagggcg aattctgcag atatc                                          505
```

<210> SEQ ID NO 60
<211> LENGTH: 520
<212> TYPE: DNA
<213> ORGANISM: Homo sapien

<400> SEQUENCE: 60

```
cgtggtcgcg gccgaggtcc tcaggacaag gaaacaggta tcagcatgat ggtagcagaa    60
```

```
accttatcac caaggtgcag gagctgactt cttccaaaga gttgtggttc cgggcagcgg    120
tcattgcctg cccttgctgg agggctgatt ttagtgttgc ttattatgtt ggccctgagg    180
atgcttcgaa gtgaaaataa gaggctgcag gatcagcggc aacagatgct ctcccgtttg    240
cactacagct ttcacggaca ccattccaaa aaggggcagg ttgcaaagtt agacttggaa    300
tgcatggtgc cggtcagtgg gcacgagaac tgctgtctga cctgtgataa aatgagacaa    360
gcagacctca gcaacgataa gatcctctcg cttgttcact ggggcatgta cagtgggcac    420
gggaagctgg aattcgtatg acggagtctt atctgaacta cacttactga acagcttgaa    480
ggacctgccc gggcggccgc tcgaaagggg cgaattctgc                          520
```

<210> SEQ ID NO 61
<211> LENGTH: 447
<212> TYPE: DNA
<213> ORGANISM: Homo sapien

<400> SEQUENCE: 61

```
agagaggtgt tttattcttt tggggacaaa gccgggttct gtgggtgtag gattctccag     60
gttctccagg ctgtagggcc cagaggctta atcagaattt tcagacaaaa ctggaacctt    120
tcttttttcc cgttggttta tttgtagtcc ttgggcaaac caatgtcttt gttcgaaaga    180
gggaaaataa tccaaacgtt tttcttttaa cttttttttt aggttcaggg gcacatgtgt    240
aggcttgcta tataggtaaa ttgcatgtca ccagggtttg ttgtacagat tatttcatca    300
tccagataaa aagcatagta ccagataggt agttttttga tcctcacccct ccttccatgc    360 tccgacctca ggtaggcccc agtgtctgac ctgcccggcg gccgctcga aagggccaat     420 tctgcagata tccatcacac tggccgg                                        447
```

<210> SEQ ID NO 62
<211> LENGTH: 83
<212> TYPE: PRT
<213> ORGANISM: Homo sapien

<400> SEQUENCE: 62

```
Lys Lys Val Leu Leu Ile Thr Ala Ile Leu Ala Val Ala Val Gly
 1               5                  10                  15

Phe Pro Val Ser Gln Asp Gln Glu Arg Glu Lys Arg Ser Ile Ser Asp
                20                  25                  30

Ser Asp Glu Leu Ala Ser Gly Phe Phe Val Phe Pro Tyr Pro Tyr Pro
            35                  40                  45

Phe Arg Pro Leu Pro Pro Ile Pro Phe Pro Arg Phe Pro Trp Phe Arg
        50                  55                  60

Arg Asn Phe Pro Ile Pro Ile Pro Ser Ala Pro Thr Thr Pro Leu Pro
65                  70                  75                  80

Ser Glu Lys
```

<210> SEQ ID NO 63
<211> LENGTH: 683
<212> TYPE: DNA
<213> ORGANISM: Homo sapien

<400> SEQUENCE: 63

```
acaaagattg gtagctttta tattttttta aaaatgctat actaagagaa aaaacaaaag     60
accacaacaa tattccaaat ataggttga gagaatgtga ctatgaagaa agtattctaa    120
ccaactaaaa aaaatattga aaccactttt gattgaagca aatgaataa tgctagattt    180
```

```
aaaaacagtg tgaaatcaca ctttggtctg taaacatatt tagctttgct tttcattcag      240
atgtatacat aaacttattt aaaatgtcat ttaagtgaac cattccaagg cataataaaa      300
aaagwggtag caaatgaaaa ttaaagcatt tattttggta gttcttcaat aatgatrcga      360
gaaactgaat tccatccagt agaagcatct ccttttgggt aatctgaaca agtrccaacc      420
cagatagcaa catccactaa tccagcacca attccttcac aaagtccttc cacagaagaa      480
gtgcgatgaa tattaattgt tgaattcatt tcagggcttc cttggtccaa ataaattata      540
gcttcaatgg gaagaggtcc tgaacattca gctccattga atgtgaaata ccaacgctga      600
cagcatgcat ttctgcattt tagccgaagt gagccactga acaaaactct tagagcacta      660
tttgaacgca tctttgtaaa tgt                                              683

<210> SEQ ID NO 64
<211> LENGTH: 749
<212> TYPE: DNA
<213> ORGANISM: Homo sapien
<220> FEATURE:
<221> NAME/KEY: misc_feature
<222> LOCATION: (1)...(749)
<223> OTHER INFORMATION: n = A,T,C or G

<400> SEQUENCE: 64
ctgttcattt gtccgccagc tcctggactg gatgtgtgaa aggcatcaca tttccatttt      60
cctccgtgta aatgttttat gtgttcgcct actgatccca ttcgttgctt ctattgtaaa     120
tatttgtcat ttgtatttat tatctctgtg ttttcccccct aaggcataaa atggtttact    180
gtgttcattt gaacccattt actgatctct gttgtatatt tttcatgcca ctgctttgtt    240
ttctcctcag aagtcgggta gatagcattt ctatcccatc cctcacgtta ttggaagcat    300
gcaacagtat ttattgctca gggtcttctg cttaaaactg aggaaggtcc acattcctgc    360
aagcattgat tgagacattt gcacaatcta aaatgtaagc aaagtaagtc attaaaaata    420
caccctctac ttgggcttta tactgcatac aaatttactc atgagccttc ctttgaggaa    480
ggatgtggat ctccaaataa agatttagtg tttattttga gctctgcatc ttancaagat    540
gatctgaaca cctctccttt gtatcaataa atagccctgt tattctgaag tgagaggacc    600
aagtatagta aaatgctgac atctaaaact aaataaatag aaaacaccag gccagaacta    660
tagtcatact cacacaaagg gagaaattta aactcgaacc aagcaaaagg cttcacggaa    720
atagcatgga aaaacaatgc ttccagtgg                                       749

<210> SEQ ID NO 65
<211> LENGTH: 612
<212> TYPE: DNA
<213> ORGANISM: Homo sapien

<400> SEQUENCE: 65
acagcagcag tagatggctg caacaacctt cctcctaccc cagcccagaa aatatttctg      60
ccccacccca ggatccggga ccaaaataaa gagcaagcag gccccctttca ctgaggtgct    120 gggtagggct cagtgccaca ttactgtgct ttgagaaaga ggaagggggat ttgtttggca    180 ctttaaaaat agaggagtaa gcaggactgg agaggccaga gaagatacca aaattggcag    240
ggagagacca tttggcgcca gtcccctagg agatgggagg agggagatag gtatgagggt    300
aggcgctaag aagagtagga ggggtccact ccaagtggca gggtgctgaa atgggctagg    360
accaacagga cactgactct aggtttatga cctgtccata cccgttccac agcagctggg    420
```

-continued

```
tgggagaaat caccattttg tgacttctaa taaaataatg ggtctaggca acagttttca      480
atggatgcta aaacgattag gtgaaaagtt gatggagaat tttaattcag gggaattagg      540
ctgataccat ctgaaaccat ttggcatcat taaaaatgtg acaacctggt ggctgccagg      600
gaggaagggg ag                                                         612
```

<210> SEQ ID NO 66
<211> LENGTH: 703
<212> TYPE: DNA
<213> ORGANISM: Homo sapien

<400> SEQUENCE: 66

```
tagcgtggtc gcggccgagg tacattgatg ggctggagag cagggttggc agcctgttct       60
gcacagaacc aagaattaca gaaaaaagtc caggagctgg agaggcacaa catctccttg      120
gtagctcagc tccgccagct gcagacgcta attgctcaaa cttccaacaa agctgcccag      180
accagcactt gtgttttgat tcttcttttt tccctggctc tcatcatcct gcccagcttc      240
agtccattcc agagtcgacc agaagctggg tctgaggatt accagcctca cggagtgact      300
tccagaaata tcctgaccca aaggacgta acagaaaatc tggagaccca agtggtagag      360
tccagactga gggagccacc tggagccaag gatgcaaatg ctcaacaag gacactgctt       420 gagaagatgg gagggaagcc aagacccagt gggcgcatcc ggtccgtgct gcatgcagat      480
gagatgtgag ctggaacaga ccttcctggc ccacttcctg atcacaagga atcctgggct      540
tccttatggc tttgcttccc actgggattc ctacttaggt gtctgccctc aggggtccaa      600
atcacttcag gacacccca gagatgtcct ttagtctctg cctgaggcct agtctgcatt      660
tgtttgcata tatgagaggg tacctgcccg ggcggccgct cga                       703
```

<210> SEQ ID NO 67
<211> LENGTH: 1022
<212> TYPE: DNA
<213> ORGANISM: Homo sapien

<400> SEQUENCE: 67

```
cttgagaaag caggattgtt ttaagttcca agatttaaca aacttactgt tcagcatcat       60
attcaagcct aaaaggaaga taggattttc aagatatatt tccaacttct ttaacatggc      120
accatggatg aactgtttct cagcactgtg ctgcttcact tggaattaag gatgaattgg      180
gaggagacag tatgacatag gtgggtaggt tgggtggtga gggaaccag ttctaatagt       240 cctcaactcc actccagctg ttcctgttcc acacggtcca ctgagctggc ccagtccctt      300
tcactcagtg tgtcaccaaa ggcagcttca aggctcaatg gcaagagacc acctataacc      360
tcttcacctt ctgctgcctc tttctgctgc cactgactgc catggccatc tgctatagcc      420
gcattgtcct cagtgtgtcc aggccccaga caaggaaggg gagccatggt gagactccaa      480
ttcccaggcc ttaatcctta accctagacc tgttgcctct agcatcattt atttatctac      540
ctacctaata gctatctacc agtcattaaa ccatggtgag attctaacca tgtctagcac      600
ctgatgctag agataatttt gttgaatccc ttcaattata aacagctgag ttagctggac      660
aaggactagg gaggcaatca gtattattta ttcttgaaca ccatcaagtc tagacttggt      720
ggcttcatat ttctatcata atccctgggg gtaagaaatc atatagcccc aggttgggaa      780
ggggaaaacg gtttgcaaca ttctcctcct tgtaggaggc gagctctgtc tcactagcta      840
tgcccctcca tcaattcacc ctatactcag atcagaagct gagtgtctga attacagtat      900
attttctaaa ttcctagccc ctgctggtga atttgccctc cccgctcct ttgacaattg       960
```

```
tccccgtgtt cgtctccggg ccctgagact ggccctgctt atcttgctga ccttcatcct    1020
ct                                                                   1022

<210> SEQ ID NO 68
<211> LENGTH: 449
<212> TYPE: DNA
<213> ORGANISM: Homo sapien

<400> SEQUENCE: 68
ccagatccat tttcagtggt ctggatttct ttttattttc ttttcaactt gaaagaaact      60
ggacattagg ccactatgtg ttgttactgc cactagtgtt caagtgcctc ttgttttccc     120
agagatttcc tgggtctgcc agaggcccag acaggctcac tcaagctctt taactgaaaa     180
gcaacaagcc actccaggac aaggttcaaa atggttacaa cagcctctac ctgtcgcccc     240
agggagaaag gggtagtgat acaagtctca tagccagaga tggttttcca ctccttctag     300
atattcccaa aaagaggctg agacaggagg ttattttcaa ttttattttg gaattaaata     360 ctttttttccc tttattactg ttgtagtccc tcacttggat atacctctgt tttcacgata    420
gaaataaggg aggtctagag cttctattc                                       449

<210> SEQ ID NO 69
<211> LENGTH: 387
<212> TYPE: DNA
<213> ORGANISM: Homo sapien
<220> FEATURE:
<221> NAME/KEY: misc_feature
<222> LOCATION: (1)...(387)
<223> OTHER INFORMATION: n = A,T,C or G

<400> SEQUENCE: 69
gcccttagcg tgggtcgcgg cncgangtct ggagcntatg tgatncctat ggtncncagg      60
cnnatactgc tantctcatt tattctcctg cnacctantc ctctnctctg gaatcacacc     120
attattgcct gttaacactg gactgtgagt accangcaat taatttgcac caanaaagtt     180
gagggtatta tcanatattg caatctgtac agagggaaga tgatttcaat ttgatttcaa     240
cttaaccttc atctttgtct gttaacacta atagagggtg tctaataaaa tggcaaattt     300
gngatctcat tnggtataac tacactcttt ttcacagatg tgatgactga atttccanca     360
acctgcccgg gcggncgntc naagggc                                         387

<210> SEQ ID NO 70
<211> LENGTH: 836
<212> TYPE: DNA
<213> ORGANISM: Homo sapien

<400> SEQUENCE: 70
tattccattt acaaaataaa ttcagccctg cactttcttt agatgccttg atttccagaa      60
tggagcttag tgctactgaa tacectggcc acagagccac ctcaggatat tcttttctcc     120
accctagttt atttatttat agatatctgt ttacaaagtc tgtagtaaat cctgatgctg     180
accatctgaa atgtactttt tttctgaatg ctgtttcaat ctaaaatagc agcttttgag     240
aaaacaatga tgtaaattcc ttatgataaa aggatgattc tatatattct ttaatgatat     300
taaatatgcc gaagccaagc acacagtctt tctaaagtgt gtgtatgttt gtgtgaatgt     360
gaatgatact gatcttatat ctgttaaaag ttgttttaaa aagctgtggc atcccattgt     420
tcatatttgc caagtcttct gtaaagatgt ctaggacgaa atattttatg tgctaatgca     480
```

-continued

```
tgtatttgta aaccagattt gtttaccact caaaattaac ttgttttctt catccaaaaa      540
agtttatttc ttccacgtac ttaaattttc tgtgtgggta taatatagct ttctaatttt      600
tttctttcac aaaggcaggt tcaaaattct gttgaaagaa aaatgctttc tgaaactgag      660
gtataacacc agagcttgct gtttaaagga ttatatgatg tacatcagtt ctataaatgt      720
gctcagcagt ttaacatgtg aatcctgttt taaagtgctc agatttcaac tgtgtaagcc      780
attgatataa cgctgtaatt aaaaatgttt atatgaaaaa aaaaaaaaaa aaaaaa         836
```

<210> SEQ ID NO 71
<211> LENGTH: 618
<212> TYPE: DNA
<213> ORGANISM: Homo sapien

<400> SEQUENCE: 71

```
gttgcagtga gctcaagtgt tgggtgtatc agctcaaaac accatgtgat gccaatcatc       60
tccacaggag caatttgttt acctttttt tctgatgctt tactaacttc atcttttaga      120
tttaaatcat tagtagatcc tagaggagcc agtttcagaa aatatagatt ctagttcagc      180
accacccgta gttgtgcatt gaaataatta tcattatgat tatgtatcag agcttctggt      240
tttctcattc tttattcatt tattcaacaa ccacgtgaca aacactggaa ttacaggatg      300
aagatgagat aatccgctcc ttggcagtgt tatactatta tataacctga aaaacaaac      360 aggtaatttt cacacaaagt aatagatatc atgacacatt taaataggg cactactgga      420 acacacagat aggacatcca ggttttgggt caatattgta gacttttggg tggatgagat      480
atgcaggttg atrccagaag gacaacaaaa acatatgtca gatagaaggg aggagcaaat      540
gccaagagct ggagctgagg aagatcactg tgaaattcta tgtagtctag ttggctggat      600
gctagagcaa agaggtgg                                                    618
```

<210> SEQ ID NO 72
<211> LENGTH: 806
<212> TYPE: DNA
<213> ORGANISM: Homo sapien

<400> SEQUENCE: 72

```
tctacgatgg ccatttgctc attgtctttc ctctgtgtgt agtgagtgac cctggcagtg       60
tttgcctgct cagagtggcc cctcagaaca acagggctgg ccttggaaaa accccaaaac      120
aggactgtgg tgacaactct ggtcaggtgt gatttgacat gagggccgga ggcggttgct      180
gacggcagga ctggagaggc tgcgtgcccg gcactggcag cgaggctcgt gtgtccccca      240
ggcagatctg ggcactttcc caacccaggt ttatgccgtc tccagggaag cctcggtgcc      300
agagtggtgg gcagatctga ccatccccac agaccagaaa caaggaattt ctgggattac      360
ccagtccccc ttcaacccag ttgatgtaac caccttcattt tttacaaata cagaatctat      420
tctactcagg ctatgggcct cgtcctcact cagttattgc gagtgttgct gtccgcatgc      480
tccgggcccc acgtggctcc tgtgctctag atcatggtga ctccccgcc ctgtggttgg      540 aatcgatgcc acggattgca ggccaaattt cagatcgtgt ttccaaacac ccttgctgtg      600
ccctttaatg ggattgaaag cacttttacc acatggagaa atatatttt aatttgtgat      660 gcttttctac aaggtccact atttctgagt ttaatgtgtt tccaacactt aaggagactc      720
taatgaaagc tgatgaattt tcttttctgt ccaaacaagt aaaataaaaa taaagtctca      780
tttagatgtt gaaaaaaaaa aaaaaa                                           806
```

<210> SEQ ID NO 73
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 73

```
actctggtaa gcttgttgtt gtccaagtga agctccctca gatgaggcgt gttggccana      60
gagccattgt caacagcaga gatgctgttg aaactcaatc ccaacttagc caaattattc     120
agtcctttca ggctagctgc atcaactctg ctgattttgt tgccatcaag atgtaattcc     180
gtaagggaag gaggaagacc ttgaggaatg ctggygatat tggyatcagc aatgcggatg     240
tasgaagagc ttcttcmttc cctggaaagc cccattttca atyccttgag ctcttcakcg     300
g                                                                    301
```

<210> SEQ ID NO 74
<211> LENGTH: 401
<212> TYPE: DNA
<213> ORGANISM: Homo sapien

<400> SEQUENCE: 74

```
agtttacatg atccctgtaa cagccatggt ctcaaactca gatgcttcct ccatctgcca      60
agtgtgttct ggatacagag cacatcgtgg cttctggggt cacactcagc ttaggctgtg     120
ggtccacaga gcactcatct ggctgggcta tggtggtggt ggctctactc aagaagcaaa     180
gcagttacca gcacattcaa acagtgtatt gaacatcttt taaatatcaa agtgagaaac     240
aagaaggcaa cataataatg ttatcagaaa gatgttagga agtaaggaca gctgtgtaaa     300
gcttgaggct gaaaagtagc ttgccagctt catttctttg gtttcttggg tagtgggccg     360
ccggaacagc aagatgtgag gttctggttc atggatcata t                         401
```

<210> SEQ ID NO 75
<211> LENGTH: 612
<212> TYPE: DNA
<213> ORGANISM: Homo sapien

<400> SEQUENCE: 75

```
ttattttca atttttattt tggttttctt acaaaggttg acattttcca taacaggtgt       60
aagagtgttg aaaaaaaaat tcaaattttt ggggagcgag ggaaggagtt aatgaaactg     120
tattgcacaa tgctctgatc aatccttctt tttctctttt gcccacaatt taagcaagta     180
gatgtgcaga gaaatggaa ggattcagct ttcagttaaa aagaagaag aagaaatggc      240
aaagagaaag ttttttcaaa tttctttctt ttttaattta gattgagttc atttatttga     300
aacagactgg gccaatgtcc acaaagaatt cctggtcagc accaccgatg tccaaaggtg     360
caatatcaag gaagggcagg cgtgatggct tatttgtttt gtattcaatg attgtctttc     420
cccattcatt tgtcttttta gagcagccat ctacaagaac agtgtaagtg aacctgctgt     480
tgccctcagc aacaagttca acatcattag agccctgtag aatgacagcc ttttcaggt     540
tgccagtctc ctcatccatg tatgcaatgc tgttcttgca gtggtaggtg atgttctgag     600
aggcatagtt gg                                                        612
```

<210> SEQ ID NO 76
<211> LENGTH: 844
<212> TYPE: DNA

<213> ORGANISM: Homo sapien

<400> SEQUENCE: 76

| | | | | | |
|---|---|---|---|---|---|
| ggctttcgag | cggccgcccg | ggcaggtctg | atggttctcg | taaaaacccc | gctagaaact | 60 |
| gcagagacct | gaaattctgc | catcctgaac | tcaagagtgg | agaatactgg | gttgaccctg | 120 |
| accaaggatg | caaattggat | gctatcaagg | tattctgtaa | tatggaaact | ggggaaacat | 180 |
| gcataagtgc | caatcctttg | aatgttccac | ggaaacactg | gtggacagat | tctagtgctg | 240 |
| agaagaaaca | cgtttggttt | ggagagtcca | tggatggtgg | ttttcagttt | agctacggca | 300 |
| atcctgaact | tcctgaagat | gtccttgatg | tgcagcykgc | attccttcga | cttctctcca | 360 |
| gccgagcttc | ccagaacatc | acatatcact | gcaaaaatag | cattgcatac | atggatcagg | 420 |
| ccagtggaaa | tgtaaagaag | gccctgaagc | tgatgggtc | aaatgaaggt | gaattcaagg | 480 |
| ctgaaggaaa | tagcaaattc | acctacacag | ttctggagga | tggttgcacg | aaacacactg | 540 |
| gggaatggag | caaaacagtc | tttgaatatc | gaacacgcaa | tgctgttcct | tgacattgca | 600 |
| ccaccaatgt | ccagaggtgc | aatgtcaagg | aacggcaggc | gagatggctt | atttgttttg | 660 |
| tattcaatga | ttgtcttgcc | ccattcattt | gtcttttgg | agcagccatc | gactaggaca | 720 |
| gagtaggtga | acctgctgtt | gccctcagca | acaagttcca | catcgttgga | accctgcaga | 780 |
| agcacagcct | tgttcaarct | gcccgtctcc | tcatccagat | acctcggccg | cgaccacgct | 840 |
| aatc | | | | | | 844 |

<210> SEQ ID NO 77
<211> LENGTH: 314
<212> TYPE: DNA
<213> ORGANISM: Homo sapien

<400> SEQUENCE: 77

| | | | | | |
|---|---|---|---|---|---|
| ccagtcctcc | acttggcctg | atgagagtgg | ggagtggcaa | gggacgtttc | tcctgcaata | 60 |
| gacacttaga | tttctctctt | gtgggaagaa | accacctgtc | catccactga | ctcttctaca | 120 |
| ttgatgtgga | aattgctgct | gctaccacca | cctcctgaag | aggcttccct | gatgccaatg | 180 |
| ccagccatcc | tggcatcctg | gccctcgagc | aggctgcggt | aagtagcgat | ctcctgctcc | 240 |
| agccgtgtct | ttatgtcaag | cagcatcttg | tactcctggt | tctgagcctc | catctcgcat | 300 |
| cggagctcac | tcag | | | | | 314 |

<210> SEQ ID NO 78
<211> LENGTH: 548
<212> TYPE: DNA
<213> ORGANISM: Homo sapien

<400> SEQUENCE: 78

| | | | | | |
|---|---|---|---|---|---|
| accaagagcc | aagtgttaca | caggatattt | taaaaataaa | atgttttttgg | aatcctcacc | 60 |
| tcccatgcta | tcttctaaga | taactacaaa | tattcttcaa | agatttaact | gagttctgcc | 120 |
| aaggacctcc | caggactcta | tccagaatga | ttattgtaaa | gctttacaaa | tcccaccttg | 180 |
| gccctagcga | taattaggaa | atcacaggca | aacctcctct | ctcggagacc | aatgaccagg | 240 |
| ccaatcagtc | tgcacattgg | ttttgttaga | tactttgtgg | agaaaaacaa | aggctcgtga | 300 |
| tagtgcagct | ctgtgcctac | agagagcctc | ccttttggtt | ctgaaattgc | tgatgtgaca | 360 |
| gagacaaagc | tgctatgggt | ctaaaaacctt | caataaagta | actaatgaca | ctcaaggtcc | 420 |
| tgggactctg | agacagacgg | tggtaaaacc | cacagctgcg | attcacattt | ccaatttatt | 480 |
| ttgagctctt | tctgaagctg | ttgcttccta | cctgagaatt | cccatttaga | gagctgcaca | 540 |

```
                                                    gcacagtc                                                548
```

<210> SEQ ID NO 79
<211> LENGTH: 646
<212> TYPE: DNA
<213> ORGANISM: Homo sapien

<400> SEQUENCE: 79

```
accccgtcac tatgtgaata aaggcagcta gaaaatggac tcaattctgc aagccttcat    60
ggcaacagcc catattaaga cttctagaac aagttaaaaa aaatcttcca tttccatcca   120
tgcatgggaa aagggcttta gtatagttta ggatggatgt gtgtataata ataaaatgat   180
aagatatgca tagtggggga ataaagcctc agagtccttc cagtatgggg aatccattgt   240
atcttagaac cgagggattt gtttagattg ttgatctact aattttttc ttcacttata    300
tttgaatttt caatgatagg acttattgga aattggggat aattctgttg tggtattaaa   360
taatattcat tttttaaaaa ctcatcttgg tattgagtta gtgcattgac ttccaatgaa   420
ttgacataag cccatatttc attttaacca gaaacaaaaa ctagaaaatg ttactcccta   480
aataggcaac aatgtatttt ataagcactg cagagattta gtaaaaaaca tgtatagtta   540
ctttagaaac aacttctgac acttgagggt tacccaatgg tctccttccc attctttata   600
tgaggtaaat gcaaaccagg gagccaccga ataaacagcc ctgagt              646
```

<210> SEQ ID NO 80
<211> LENGTH: 276
<212> TYPE: DNA
<213> ORGANISM: Homo sapien
<220> FEATURE:
<221> NAME/KEY: misc_feature
<222> LOCATION: (1)...(276)
<223> OTHER INFORMATION: n = A,T,C or G

<400> SEQUENCE: 80

```
gtctgaatga gcttcnctgc gagatgggan ancataaccc agaantccaa aancntanng    60
aacgnnaaaa cccgntngaa caagnaaaacn gcaactnacg gccgcctgnt gnagggcgag   120
gacgcccacc tctcctcctc ccagttctcc tctggatcgc agncatccan agatgtgacc   180
tcttccagcc gccaaatccg caccaaggtc atggatgtgc acgatggcaa ggtgggtgtc   240
cacccacgaa caggtccttc gcaccaagaa ctgagg                             276
```

<210> SEQ ID NO 81
<211> LENGTH: 647
<212> TYPE: DNA
<213> ORGANISM: Homo sapien

<400> SEQUENCE: 81

```
gtcctgcctt tcatcttttc tttaaaaaaa ataaatgttt acaaaacatt tccctcagat    60
tttaaaattc atggaagtaa taaacagtaa taaaatatgg atactatgaa aactgacaca   120
cagaaaaaca taaccataaa atattgttcc aggatacaga tattaattaa gagtgacttc   180
gttagcaaca cgtagacatt catacatatc cggtggaaga ctggtttctg agatgcgatt   240
gccatccaaa cgcaaatgct tgatcttgga gtaggrtaat ggccccagga tcttgcagaa   300
gctctttatg tcaaacttct caagttgatt gacctccagg taatagtttt caaggttttc   360
attgacagtt ggtatgtttt taagcttgtt ataggacaga tccagctcaa ccagggatga   420
cacattgaaa gaatttccag gtattccact atcagccagt tcgttgtgag ataaacgcag   480
```

| atactgcaat gcattaaaac gcttgaaata ctcatcaggg atgttgctga tcttattgtt | 540 |
| gtctaagtag agagttagaa gagagacagg gagaccagaa ggcagtctgg ctatctgatt | 600 |
| gaagctcaag tcaaggtatt cgagtgattt aagacccttta aaagcag | 647 |

<210> SEQ ID NO 82
<211> LENGTH: 878
<212> TYPE: DNA
<213> ORGANISM: Homo sapien

<400> SEQUENCE: 82

| ccttctttcc ccactcaatt cttcctgccc tgttattaat taagatatct tcagcttgta | 60 |
| gtcagacaca atcagaatya cagaaaaatc ctgcctaagg caagaaaata taagacaaga | 120 |
| ctatgatatc aatgaatgtg ggttaagtaa tagatttcca gctaaattgg tctaaaaaag | 180 |
| aatattaagt gtggacagac ctatttcaaa ggagcttaat tgatctcact tgttttagtt | 240 |
| ctgatccagg gagatcaccc ctctaattat ttctgaactt ggttaataaa agtttataag | 300 |
| atttttatga agcagccact gtatgatatt ttaagcaaat atgttattta aaatattgat | 360 |
| ccttcccttg gaccaccttc atgttagttg ggtattataa ataagagata caaccatgaa | 420 |
| tatattatgt ttatacaaaa tcaatctgaa cacaattcat aaagatttct cttttatacc | 480 |
| ttcctcactg gcccctcca cctgcccata gtcaccaaat tctgttttaa atcaatgacc | 540 |
| taagatcaac aatgaagtat tttataaatg tatttatgct gctagactgt gggtcaaatg | 600 |
| tttccatttt caaattattt agaattctta tgagtttaaa atttgtaaat ttctaaatcc | 660 |
| aatcatgtaa aatgaaactg ttgctccatt ggagtagtct cccacctaaa tatcaagatg | 720 |
| gctatatgct aaaagagaa aatatggtca agtctaaaat ggctaattgt cctatgatgc | 780 |
| tattatcata gactaatgac atttatcttc aaaacaccaa attgtctttta gaaaaattaa | 840 |
| tgtgattaca ggtagagaac ctcggccgcg accacgct | 878 |

<210> SEQ ID NO 83
<211> LENGTH: 645
<212> TYPE: DNA
<213> ORGANISM: Homo sapien

<400> SEQUENCE: 83

| acaaacattt tacaaaaaag aacattacca atatcagtgg cagtaagggc aagctgaaga | 60 |
| ataaatagac tgagtttccg ggcaatgtct gtcctcaaag acatccaaac tgcgttcagg | 120 |
| cagctgaaac aggcttctt cccagtgaca agcatatgtg gtcagtaata caaacgatgg | 180 |
| taaatgaggc tactacatag gcccagttaa caaactcctc ttctcctcgg gtaggccatg | 240 |
| atacaagtgg aactcatcaa ataatttaaa cccaaggcga taacaacgct atttcccatc | 300 |
| taaactcatt taagccttca caatgtcgca atggattcag ttacttgcaa cgatcccgg | 360 |
| gttgtcatac agatacttgt ttttacacat aacgctgtgc catcccttcc ttcactgccc | 420 |
| cagtcaggtt tcctgttgtt ggaccgaaag gggatacatt ttagaaatgc ttccctcaag | 480 |
| acagaagtga gaaagaaagg agaccctgag gccaggatct attaaacctg gtgtgtgcgc | 540 |
| aaaagggagg gggaaggcag gaatttgaaa ggataaacgt ctcctttgcg ccgaggaatc | 600 |
| aggaagcgtg actcacttgg gtctgggacg ataccgaaat ccggt | 645 |

<210> SEQ ID NO 84
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 84

| | | | | | |
|---|---|---|---|---|---|
| tctgatgtca | atcacaactt | gaaggatgcc | aatgatgtac | caatccaatg | tgaaatctct | 60 |
| cctcttatct | cctatgctgg | agaaggatta | gaaggttatg | tggcagataa | agaattccat | 120 |
| gcacctctaa | tcatcgatga | gaatggagtt | catgggctgg | tgaaaaatgg | tatttgaacc | 180 |
| agataccaag | ttttgtttgc | cacgatagga | atagctttta | tttttgatag | accaactgtg | 240 |
| aacctacaag | acgtcttgga | caactgaagn | ttaaatatcc | acangggttt | attttgcttg | 300 |
| g | | | | | | 301 |

<210> SEQ ID NO 85
<211> LENGTH: 296
<212> TYPE: DNA
<213> ORGANISM: Homo sapien
<220> FEATURE:
<221> NAME/KEY: misc_feature
<222> LOCATION: (1)...(296)
<223> OTHER INFORMATION: n = A,T,C or G

<400> SEQUENCE: 85

| | | | | | |
|---|---|---|---|---|---|
| agcgtgggtc | gcggcncgan | gtagagaacc | gactgaaacg | tttgagatga | agaaagttct | 60 |
| cctcctgatc | acagccatct | tggcagtggc | tgttggtttc | ccagtctctc | aagaccagga | 120 |
| acgagaaaaa | agaagtatca | gtgacagcga | tgaattagct | tcagggtttt | ttgtgttccc | 180 |
| ttacccatat | ccatttcgcc | cacttccacc | aattccattt | ccaagatttc | catggtttan | 240 |
| acgtaatttt | cctattccaa | tacctgaatc | tgcccctaca | actccccttc | ctagcg | 296 |

<210> SEQ ID NO 86
<211> LENGTH: 806
<212> TYPE: DNA
<213> ORGANISM: Homo sapien

<400> SEQUENCE: 86

| | | | | | |
|---|---|---|---|---|---|
| tctacgatgg | ccatttgctc | attgtctttc | ctctgtgtgt | agtgagtgac | cctggcagtg | 60 |
| tttgcctgct | cagagtggcc | cctcagaaca | acagggctgg | ccttggaaaa | accccaaaac | 120 |
| aggactgtgg | tgacaactct | ggtcaggtgt | gatttgacat | gagggccgga | ggcggttgct | 180 |
| gacggcagga | ctggagaggc | tgcgtgcccg | gcactggcag | cgaggctcgt | gtgtccccca | 240 |
| ggcagatctg | gcactttcc | caacccaggt | ttatgccgtc | tccagggaag | cctcggtgcc | 300 |
| agagtggtgg | gcagatctga | ccatccccac | agaccagaaa | caaggaattt | ctgggattac | 360 |
| ccagtccccc | ttcaacccag | ttgatgtaac | cacctcattt | tttacaaata | cagaatctat | 420 |
| tctactcagg | ctatgggcct | cgtcctcact | cagttattgc | gagtgttgct | gtccgcatgc | 480 |
| tccgggcccc | acgtggctcc | tgtgctctag | atcatggtga | ctccccgcc | ctgtggttgg | 540 |
| aatcgatgcc | acgattgca | ggccaaattt | cagatcgtgt | ttccaaacac | ccttgctgtg | 600 |
| cccttaatg | ggattgaaag | cacttttacc | acatggagaa | atatattttt | aatttgtgat | 660 |
| gcttttctac | aaggtccact | atttctgagt | ttaatgtgtt | tccaacactt | aaggagactc | 720 |
| taatgaaagc | tgatgaattt | tcttttctgt | ccaaacaagt | aaaataaaaa | taaagtcta | 780 |
| tttagatgtt | gaaaaaaaaa | aaaaaa | | | | 806 |

<210> SEQ ID NO 87

```
<211> LENGTH: 620
<212> TYPE: DNA
<213> ORGANISM: Homo sapien

<400> SEQUENCE: 87
tttttgcatc agatctgaaa tgtctgagag taatagtttc tgttgaattt ttttttgttc      60 attttctgc acagtccatt ctgttttat tactatctag cttgaaata tatagtttga       120 aattatgaca tccttcctct tgttatttt cctcatgatt gctttggcta ttcaaagttt     180
attttagttt catgtaaatt tttgaattgt attttccatt attgtgaaaa tagtaccact     240
gcaattttaa taggaagttt attgaatcta tagattactt tggataatat ggcacttcaa     300
taatattcat gttttcaatt catagacaaa atattttaaa atttatttgt atcttttcta     360
atttttcctt tttttattgt aaagatttac ctccttggtt aatattttcc tcagaaattt     420
attatttaag gtatagtcaa taaaattttc ttcctctatt ttgtcagata gtttaagtgt    480
atgaaaccat agatatactt gtatgttaat tttatatttt gctaatttac tgagtgtatt    540
tattagttta gagaggtttt aatgtactgt ttatggtttt ttaaatataa gattacttat    600
tttttaaaaa aaaaaaaaaa                                                620

<210> SEQ ID NO 88
<211> LENGTH: 308
<212> TYPE: DNA
<213> ORGANISM: Homo sapien
<220> FEATURE:
<221> NAME/KEY: misc_feature
<222> LOCATION: (1)...(308)
<223> OTHER INFORMATION: n = A,T,C or G

<400> SEQUENCE: 88
tagctgtgnt cagcaggccg aggttttttt ttttttgag atggagtctc gccctgtcac      60
ccaggctgga gtgcagtggc ctgatctcag ctcactgcaa gctccacctc ctggattcac    120
gctattctcc tgcctcagcc tcccaagtag ctgggactac aggcgcccgc caccacgccc    180
agctaatttt ttgnatttt agtacnagat gcggtttcat cgtgttagcc agcatggnct    240
cgatctcctg acctcgtgaa ctgcccgcct cggcctccca agacctgcc cgggcnggcc    300 gctcgaaa                                                             308

<210> SEQ ID NO 89
<211> LENGTH: 492
<212> TYPE: DNA
<213> ORGANISM: Homo sapien
<220> FEATURE:
<221> NAME/KEY: misc_feature
<222> LOCATION: (1)...(492)
<223> OTHER INFORMATION: n = A,T,C or G

<400> SEQUENCE: 89
agcggccgcc cgggcaggtc tgttaagtaa catacatatc accttaataa aaatcaagat      60
gaaatgtttt agaaactatt ttatcaaaag tggctctgat acaaagactt gtacatgatt    120
gttcacagca gcactattaa tgccaaaaag tagacaaaac ctaaatgtcc attaactgat    180
aagcaaaatg tggtatatcc atacaatgga atattatgta gcccacaaca tggcatggag    240
tactacaaca tggatgagcc tcaaaaacgt tatgctaaat gaaaaaagtc agatataggga    300 aaccacatgt catatgatcc catttatatg aaatagccag aaaaggcaag tcatagaaac    360
aagatagatc ggaaaatggg ttggaggact acaaatggca ccaggatct ttgaagttga    420 tggaaatggt ctaaaatcag actgtggntg tggttgaaca agtctgtaaa tttaccaaaa    480
```

```
tgcgttaata ca                                                        492
```

<210> SEQ ID NO 90
<211> LENGTH: 390
<212> TYPE: DNA
<213> ORGANISM: Homo sapien
<220> FEATURE:
<221> NAME/KEY: misc_feature
<222> LOCATION: (1)...(390)
<223> OTHER INFORMATION: n = A,T,C or G
<400> SEQUENCE: 90

```
tcgagcggcc gcccgggcag gtacaagctt tttttttttt tttttttttt ttttctaaca     60
gttctctgtt ttattgcaat acagcaaagt ctggttaata ttaagngata tcaacataaa    120
gtattggtga ggagtctttt gtgacatttt ttaccatccc accttaaata tttctgtgca    180
aaanaatcca catcattgtt tggtancana ggatctctta aaaagttccc taanacactg    240
agggcataaa accaaacaaa ataaaataag gagtgatagg ctaaagcagt atcttcccct    300
ccatccacat ttgncaagca ttatattcta accaaaaaat gatcacacca ggccatgcaa    360
aactgtccaa tattaccgag aaaaaaccct                                     390
```

<210> SEQ ID NO 91
<211> LENGTH: 192
<212> TYPE: DNA
<213> ORGANISM: Homo sapien
<400> SEQUENCE: 91

```
agcgtggtcg cggccgaggt ctgtcaatta atgctagtcc tcaggattta aaaaataatc     60
ttaactcaaa gtccaatgca aaacattaa gttggtaatt actcttgatc ttgaattact    120
tccgttacga aagtccttca cattttttcaa actaagctac tatatttaag gcctgcccgg    180
gcggccgctc ga                                                        192
```

<210> SEQ ID NO 92
<211> LENGTH: 570
<212> TYPE: DNA
<213> ORGANISM: Homo sapien
<220> FEATURE:
<221> NAME/KEY: misc_feature
<222> LOCATION: (1)...(570)
<223> OTHER INFORMATION: n = A,T,C or G
<400> SEQUENCE: 92

```
agcgtggtcg cggccgaggt ctgacaacta acaaagaagc aaaaactggc atcttggaca     60
tcctagtatt acacttgcaa gcaattagaa cacaaggagg gccaaggaaa aagtttagct    120
ttgaatcact tccaaatcta ctgattttga ggttccgcag tagttctaac aaaacttttc    180
agacaatgtt aactttcgat taagaaagaa aaaaccccca aacatcttca ggaattccat    240
gccaggttca gtctcttcca gtgagcccgc ttgctaaaag tccacgtgca ccattaatta    300
gctgggctgg cagcaccatg taaaagaag cctattcacc accaaccaca cagactagac    360
atgtaaagta ggatcaagta atggatgaca accatggtcg tggaatatgg tcaatgagag    420
tcagaaaagt acaggcacca gtacaagcag cagataacga aattgacggg ccaaaggata    480
aaaataggct tatttaaata ggatgctaca gaacacatnc acttctaatt ggaagctgct    540
ttacactggg tggcattgna ccatatgcat                                     570
```

<210> SEQ ID NO 93

<211> LENGTH: 446
<212> TYPE: DNA
<213> ORGANISM: Homo sapien
<220> FEATURE:
<221> NAME/KEY: misc_feature
<222> LOCATION: (1)...(446)
<223> OTHER INFORMATION: n = A,T,C or G

<400> SEQUENCE: 93

| | | | | | |
|---|---|---|---|---|---|
| tcgagcggcc | gcccgggcag | gtccaggttt | ttatttagtt | gtgtaatctt | ggacaagtta | 60 |
| cctaactttt | ttgagtctga | atatatttaa | tctgcaaaat | gagaatcatg | ataatacgtc | 120 |
| ataggcttaa | ttaggaggat | taaatgaaat | aatttatagg | tggtgccatg | gttacataca | 180 |
| agtattagta | gttaattctt | ttcctttgtt | tactttata | gtataggttg | gatgaaggtt | 240 |
| ccagtatagg | caaaaatact | acttgggggt | aaagtagagt | gtgatacttt | atttgaaatg | 300 |
| ttccctgaat | ctgatcttta | cttttgnta | ctgctgcact | acccaaatcc | aaattttcat | 360 |
| cccaacattc | ttggatttgt | gggacagcng | tagcagcttt | tccaatataa | tctatactac | 420 |
| atcttttctt | actttggtgc | tttttg | | | | 446 |

<210> SEQ ID NO 94
<211> LENGTH: 409
<212> TYPE: DNA
<213> ORGANISM: Homo sapien

<400> SEQUENCE: 94

| | | | | | |
|---|---|---|---|---|---|
| cgagcggccg | cccgggcagg | tccatcagct | cttctgctta | gaatacgagg | cagacagtgg | 60 |
| agaggtcaca | tcagttatcg | tctatcaggg | tgatgaccca | agaaaggtga | gtgagaaggt | 120 |
| gtcggcacac | acgcctctgg | atccacccat | gcgagaagcc | ctcaagttgc | gtatccagga | 180 |
| ggagattgca | aagcgccaga | gccaacactg | accatgttga | aggcgttctc | tccaggctgg | 240 |
| attcactgca | ctcggaagaa | ttctgcccag | ggaatttagt | gtggggtac | caggaccagt | 300 |
| ttgtcttgat | cttgagaccc | ccagagctgc | tgcatccata | gggtgttgca | ggactacacc | 360 |
| tggcctgcct | tgcagtcatt | ctttcttata | tgttgaccca | tttgcccaa | | 409 |

<210> SEQ ID NO 95
<211> LENGTH: 490
<212> TYPE: DNA
<213> ORGANISM: Homo sapien
<220> FEATURE:
<221> NAME/KEY: misc_feature
<222> LOCATION: (1)...(490)
<223> OTHER INFORMATION: n = A,T,C or G

<400> SEQUENCE: 95

| | | | | | |
|---|---|---|---|---|---|
| tcgagcggcc | gcccgggcag | gtcctacttg | tttgcagctt | ccacacactg | cacctaccta | 60 |
| ctacctctct | tccatgctta | actgggttta | gaaaggtgag | ctatgcgtag | aagaactact | 120 |
| tgggatattc | aagtgctgta | tttgaacgat | aagcctatag | ataacagtct | gaagctgcaa | 180 |
| gggagacttt | gttagtacac | tactataaac | aggtaaacta | cctgtttgta | cttgatatag | 240 |
| tgcatatgaa | atgactgatt | taatacaaaa | ctacagaaca | tgcaaaattt | tttctgagat | 300 |
| gttaagtatt | acttcagtgg | agaacaaaac | ttacttaacc | tttcgctaat | gcatgtagta | 360 |
| ccagaaagca | aacatggttt | tagcttcctt | tactcaaaat | atgaacatta | agtggttgtg | 420 |
| aatttttgtct | gccaagtggt | tcagaaaata | cattataaat | aacctaagtt | aaaaaaaaga | 480 |
| aactgngaac | | | | | | 490 |

<210> SEQ ID NO 96
<211> LENGTH: 223
<212> TYPE: DNA
<213> ORGANISM: Homo sapien

<400> SEQUENCE: 96

| | | | | |
|---|---|---|---|---|
| agcgtggtcg cggccgaggt ctggaagccc accctaggac ttgaatggca ccttgtcctt | | | | 60 |
| tctctgccag taatgcaatc caacacaata tgctacagga aaaacagaat ttccacggtg | | | | 120 |
| ccgccctctg gtacaaggga aacagcacgc aaagcaaaag ccacagagg gctccctgag | | | | 180 |
| aatccagtac aactaagcga ggacctgccc gggcggccgc tcg | | | | 223 |

<210> SEQ ID NO 97
<211> LENGTH: 527
<212> TYPE: DNA
<213> ORGANISM: Homo sapien
<220> FEATURE:
<221> NAME/KEY: misc_feature
<222> LOCATION: (1)...(527)
<223> OTHER INFORMATION: n = A,T,C or G

<400> SEQUENCE: 97

| | | | | |
|---|---|---|---|---|
| tcgagcggcc gcccgggcag gtctgtgcag agacactga agtgggtagt gtccataatc | | | | 60 |
| tttttagcct gttgctgaaa ttccagttgt actcctttcaa accaaaatgc ttacaggatc | | | | 120 |
| atgggaaagc ctcggttgca gaaatcaaga caggcaagtg ggaagataac tcggctttga | | | | 180 |
| ggttaaacag atctgggttc aaagcatagt ttcactctct gtcttgtgaa gtgtcctggg | | | | 240 |
| tgaagtcatt tcctctcttg aatttcagag aggatgaaaa tataaaaagt ataataacta | | | | 300 |
| tcttcataat ctttgtgagg attaaagaag acgaagtgtg tgaaaagcta agcacagagc | | | | 360 |
| aggcattcta caataagtag ttattatttt tggaaccatc ccgncccta g ccccagccca | | | | 420 |
| attaccttct cttagnctct tcatatcgaa ngccgtaatc ttgaccttct cttgcnactg | | | | 480 |
| gattggtgct ggttgatgcc caaacttccc gagatgctgt ctgggaa | | | | 527 |

<210> SEQ ID NO 98
<211> LENGTH: 514
<212> TYPE: DNA
<213> ORGANISM: Homo sapien
<220> FEATURE:
<221> NAME/KEY: misc_feature
<222> LOCATION: (1)...(514)
<223> OTHER INFORMATION: n = A,T,C or G

<400> SEQUENCE: 98

| | | | | |
|---|---|---|---|---|
| tcgagcggcc gcccgggcag gtctggctcc catggccctt ggggtggcct gactctgtca | | | | 60 |
| ctattcctaa aaccttctag gacatctgct ccaggaagaa ctttcaacac caaaattcat | | | | 120 |
| ctcaatttta cagatgggaa aagtgattct gagaccagac cagggtcagg ccaaggtcat | | | | 180 |
| ccagcatcag tggctgggct gagactgggc caggggaacc ctgtctgctc ctcttttcc | | | | 240 |
| cagagctgtg agttctctag ccaaggctgc actcttgagg gagagccagg aagcatagct | | | | 300 |
| gaggccatga caacctcact cttcacctga aatttaacc cgtggcagag gatccaggca | | | | 360 |
| catataggct tcggagccaa acaggacctc ggccgcgacc acgctaagcc gaattccagc | | | | 420 |
| acactggcgg ccgttactag tggatcccga gcttnggtac caagcttggc gtaatcatgg | | | | 480 |
| gcatagctgg ttcctggggt gaaaatggta tccg | | | | 514 |

<210> SEQ ID NO 99
<211> LENGTH: 530
<212> TYPE: DNA

<213> ORGANISM: Homo sapien
<220> FEATURE:
<221> NAME/KEY: misc_feature
<222> LOCATION: (1)...(530)
<223> OTHER INFORMATION: n = A,T,C or G

<400> SEQUENCE: 99

```
tcgagcggcc gcccgggcag gtctgaagaa acaggtataa atttggcagc cagtaatttt      60
gacagggaag ttacagcttg catgacttta aatatgtaaa tttgaaaata ctgaatttcg     120
agtaatcatt gtgctttgtg ttgatctgaa aaatataaca ctggctgtcg aagaagcatg     180
ttcaaaaata tttaattcac ttcaaaatgt catacaaatt atggtggttt ctatgcaccc     240
ctaaagcttc aagtcattta gctcaggtac atactaaagt aatatattaa ttcttccagt     300
acagtggtgt ttcataccat tgacatttgc atacccctaga ataatttaag aaagacatgt    360
gtaatattca caatgttcag aaaagcaagc aaaaggtcaa ggaacctgct ttggttcttc     420
tggagatggn ctcatatcag cttcataaac attcattcta caaaatagta agctaaccat     480
ttgaacccca atttccagat taagcatatt ttctcataaa tnatgaagcc                530
```

<210> SEQ ID NO 100
<211> LENGTH: 529
<212> TYPE: DNA
<213> ORGANISM: Homo sapien

<400> SEQUENCE: 100

```
agcgtggtcg cggccgaggt ccaggcacgg tggcttatgt gtgtaatccc agcacttggg      60
gaggctgagg gaggtggatc acttgagtcc aggagtttga gaccagtctg gcaacatgg     120
cgaaacttca tcactaccaa agaagaaaaa aattagccag gtgtggtggt gtatgcctgt     180
agtcccagat actctggtgg ctgaggtgag aggatagctt gagcccagga aattgaggct     240
gcagtgaact atgattgcac tactgtgctc cagcttgggc aacagagtga atcttgtct     300
ccaaaagtcc ttgaaggatt ttaggaagtt gttaaaagtc ttgaaacgat gtttgggggc     360
atgttagggt tcttgaatgt ttaattcctc taataactgc ttattcaaga gaagcatttc     420
tgactgggtg cggggcagtg gcttcatgcc ccataatccc agtactttgg gaggctgaag     480
caggaacatt gcttgagccc aggacttcaa gaacagcctg ggtaacata                 529
```

<210> SEQ ID NO 101
<211> LENGTH: 277
<212> TYPE: DNA
<213> ORGANISM: Homo sapien

<400> SEQUENCE: 101

```
tcgagcggcc gcccgggcag gtcgcaggaa gaggatggaa actgaggagt ccaggaagaa      60
gagggaacga gatcttgagc tggaaatggg agatgattat attttggatc ttcagaagta    120
ctgggatttta atgaatttgt ctgaaaaaca tgataagata ccagaaatct gggaaggcca    180
taatatagct gattatattg atccagccat catgaagaaa ttggaagaat tagaaaaaga    240
agaagagctg agaacagacc tcggccgcga ccacgct                              277
```

<210> SEQ ID NO 102
<211> LENGTH: 490
<212> TYPE: DNA
<213> ORGANISM: Homo sapien

<400> SEQUENCE: 102

```
gcgtggtcgc ggccgaggtc tgacggcttt gctgtcccag agccgcctaa acgcaagaaa      60
```

```
agtcgatggg acagttagag gggatgtgct aaagcgtgaa atcagttgtc cttaattttt      120
agaaagattt tggtaactag gtgtctcagg gctgggttgg ggtccaaagt gtaaggaccc      180 cctgcccttga gtggagagct ggagcttgga gacattaccc cttcatcaga aggaattttc      240
```

```
ggatgttttc ttgggaagct gttttggtcc ttggaagcag tgagagctgg gaagcttctt      300
ttggctctag gtgagttgtc atgtgggtaa gttgaggtta tcttgggata aagggtcttc      360
tagggcacaa aactcactct aggtttatat tgtatgtagc ttatattttt tactaaggtg      420
tcaccttata agcatctata aattgacttc ttttcttag ttgtatgacc tgccccgggc      480
ggccgctcga                                                              490

<210> SEQ ID NO 103
<211> LENGTH: 490
<212> TYPE: DNA
<213> ORGANISM: Homo sapien

<400> SEQUENCE: 103
gagcggccgc ccgggcaggt ccaaaccagc ttgctcataa gtcattaacc aaatccatta       60
taggtaattt gttcagttca atgtttacaa ttcttatgga aaaaattagc aacacacaca      120
tttaaaacgt gtgcatttac ctttgcgtga gtgcttaaaa tacatatttc tatttcaaga      180
tgacatttaa aaattattct aatatatcag cagcaaaaat ataatttgca attacaaaaa      240
actaaactag aatccttaag ttattctcat gtttacagtt gtgattcttt aataaatact      300
attatgcagc tctattgttt aagctttctg gatttggttt aaacacatgc atatatattg      360
tcaattgtgg gaagctttac aagttatatt ccatgcactt tttggacaga gttctaacag      420
agccagccag tccacaaaac aggcaagaca aaagttgaat taactggggc aaaataggac      480
tcttatgcaa                                                              490

<210> SEQ ID NO 104
<211> LENGTH: 489
<212> TYPE: DNA
<213> ORGANISM: Homo sapien

<400> SEQUENCE: 104
cgtggtcgcg gccgaggtcc aggctggtct cgaactcctg accttgtgat ctgcccgcct       60
cggcctccca agtgttggg attacaggca tgagccactg cgcccgaccg agttgaacat      120
ttaatgtcag actaggccag agtttctcaa tcttttttatt ctcacttccc aaaggagccg      180
ttggagattt tcccctcaat ctctctcctt catgaaattt cataccacaa atatagtatg      240
ttttatttat gtactgtgac cctttgaagg atcacaaacc aatataatag ttttttcttt      300
taacccgtca aggaccaagt ttttgccccct gttggaaatg cataaactgg actgatgaat      360
tggtatagat ggcttttatc atgaggatca gaaaacttg aaattccttg ctacgacac      420 tccatattta tcaccgtata gggaggacct tggtatgggg aagtagaaac acttctacac      480
tttacagca                                                               489

<210> SEQ ID NO 105
<211> LENGTH: 479
<212> TYPE: DNA
<213> ORGANISM: Homo sapien
<220> FEATURE:
<221> NAME/KEY: misc_feature
<222> LOCATION: (1)...(479)
<223> OTHER INFORMATION: n = A,T,C or G
```

<400> SEQUENCE: 105

| gcgtggtcgc ggccgaggtc tgactggctt cagccccaga agttgagctg gcctttagac | 60 |
| aaaataattg cacctccctc tgctgcttat tcccttccgt ttttcatttg agtgtgaaca | 120 |
| gttagataaa atctgtggct gnctcttcca ccttgctcta gtttccattg ctgtgagcag | 180 |
| gccctcctat gccccgcatt tagctacaat gctgtggact cacttgattc tttttctccg | 240 |
| agctttgtct agaaatatgt gaaggtgagg ttaagtgctt ctctgtgtag atccacttag | 300 |
| ccctgtctgc tgtctcgatg ggcgttgctt cgtctctcct ctcttccatc ctttccattt | 360 |
| gcttctcacc accttctggc ttcttttctt aatgcaataa aggcagtttc taacaaagaa | 420 |
| agaatgtggg ctttggagtt agacagacct ggntttaaat tctgcttctg gctctccaa | 479 |

<210> SEQ ID NO 106
<211> LENGTH: 511
<212> TYPE: DNA
<213> ORGANISM: Homo sapien

<400> SEQUENCE: 106

| tcgcggccga ggtccaaaac gtggattcca atgacctgcc ttgagcccgc ggttgccagg | 60 |
| agttggacct gcagtagtat gggaagctca cggcctaaat accgactgcc ctctgacccc | 120 |
| accgtccagc gattctagaa catttctagt aggaaagaca tagcaaggga ttttcatgat | 180 |
| tgggaaatac tgggagacaa gctgaagatt tgttaagggc tatgcttctg tcatctttta | 240 |
| ggtatttaag gctactcctt tagctagcta ctttgagctg tttaaagtga ctatctccct | 300 |
| acacagagtt acacaatgag catctctgaa agagaatatt accctggatt tccaaagatg | 360 |
| tactctaaca ggatgaccag gcaaaaggtg acccggggga ggagtctgtt ataacactcg | 420 |
| gacccacatg ttctcaaggc acttcagaac tttgggaaat cattttgtac cggatcctca | 480 |
| gaaagcattt atggaaatac acatccttta g | 511 |

<210> SEQ ID NO 107
<211> LENGTH: 451
<212> TYPE: DNA
<213> ORGANISM: Homo sapien

<400> SEQUENCE: 107

| ggccgcccgg gcaggtccag aatatcaaat caaaaggtca caaatgttca cttcctcctc | 60 |
| caccctctta catattggat cttcaattgc aatagggagt gtaagatggg cattttagag | 120 |
| acgtagttgc atcagcagaa gcaaacccat cttatacaaa tgggttttgg ggataggaaa | 180 |
| aggctgctaa aaattcacaa gtcaccattc cccagaagca atgaatagcc gtagaagacc | 240 |
| aaggaagatc aacaagtttc caaagtgcta aagccagaga tttggcccct ccaaaatacc | 300 |
| accaggacgc ctggacccgt gggctctccg catgtcacca ctgactgcca ggatgctgct | 360 |
| gcacctccct tccttgagac acaacagaga gacagtgaag tcacccaaga ctgggatcat | 420 |
| cagaggctcc tcatgcttgc tacagagaag c | 451 |

<210> SEQ ID NO 108
<211> LENGTH: 461
<212> TYPE: DNA
<213> ORGANISM: Homo sapien

<400> SEQUENCE: 108

| ccgcccgggc aggtcctgaa acattcaga ctaatcaaaa tggtactact gtaacttctt | 60 |
| ataatacata atataaaagt ttttgaaaga tatagacaca attaacccct aaacaacaca | 120 |

```
ctatctgatt ctcaaaagca atggctattt aacaagatgt aaaaggacaa taacatatca    180
aagaactttc acacacctaa agatagcatt tagcagcaag ttagtcagac aaaacaaaca    240
caaatatttt cacatttcct atgtttgttt ttaactttac ttcataaagc cactgataat    300
tgaggtttct ttcaagtata agatttctaa aattaaaaac tgttttttgac atatttttat   360 aaagaaataa aaagcaaaac gcaatccaac tatttatatg agtccctctt ctccaacagc    420
tttagatggt tttctgagta ctttttttaca cagaatattt t                       461
```

<210> SEQ ID NO 109
<211> LENGTH: 441
<212> TYPE: DNA
<213> ORGANISM: Homo sapien

<400> SEQUENCE: 109

```
ggccgcccgg gcaggtctga ttataagaga aagaaatcca gtgacacgag ggcaggcagg     60
ccccgctctg ctctgatcga gaaaagcttc ctgatgtcag ggagatggaa ctgccaccat    120
cagaaccatg gcactttggg tgaaggtgtg tcagcgacca aggggcagg aaatgggcag     180 tgactaaggg ggcaggaaac aggcaggcac atggcaaggt tctcccagcc catcagccca    240
gtgatggcct cgattttgaa gctgcactac tgtctgaaaa gcacaattac tggtgactct    300
taacaaactt cagcatactg gggaaggaga ctgtcaagta actgaattgg aaagatgaaa    360
aagaaccatc tctaaaagtt gatgcttgtc agaagaataa cctcctttgt gcaagtcttg    420
caacatcttc attcaaccac a                                              441
```

<210> SEQ ID NO 110
<211> LENGTH: 451
<212> TYPE: DNA
<213> ORGANISM: Homo sapien
<220> FEATURE:
<221> NAME/KEY: misc_feature
<222> LOCATION: (1)...(451)
<223> OTHER INFORMATION: n = A,T,C or G

<400> SEQUENCE: 110

```
ggtcgcggcc gaggtctggg gaagggggtga gaatccctgg gccttgccca gtcctgagct    60
ctgggtgtct gcagggaagc acagtggtga gttagtgtta aagaaagcat ccagagaggt   120
aagaggggct tgggtagcac cctttgcctc tgtcacttcc gcaaaaactt cttgttgagg    180
aggaagatga gaaggttgac attgactttg gccttgttga agagtttcat gacagccaca    240
ccctcatact ggagctgcan gagatcctga tagtgaagct tgaaatcgct ccatgtccac    300
acccaggaac ttggcattta cttcaaactt tcctgcctca tctcccggcg tgatgtcaaa    360
natgacgttt cttgaagtga gaggcgggaa agatcttcaa tttccaccaa agacacccctt  420 tttccaggaa gcttgagcaa caagtgtaat g                                   451
```

<210> SEQ ID NO 111
<211> LENGTH: 407
<212> TYPE: DNA
<213> ORGANISM: Homo sapien
<220> FEATURE:
<221> NAME/KEY: misc_feature
<222> LOCATION: (1)...(407)
<223> OTHER INFORMATION: n = A,T,C or G

<400> SEQUENCE: 111

```
ggccgacgtt cgacctgact tctttngagc agntgncact accccgtcttg aggaatgccg    60
```

-continued

| | | |
|---|---|---|
| actgcagaca gtggcccang gcaaagagtg tgcgtcatcg atganattgg naagatggag | 120 |
| ctcttcagtc agnttttcat tcaagctgnt cgtcagacgc tgtctacccc agggactata | 180 |
| atcctnggca caatcccagt tcctanagga aagccactgn ctcttgtaga agaaatcana | 240 |
| cacanaaagg atgtgaacng tgtttaatgt caccaaggga aaacatgaaa ccaccttctg | 300 |
| ccagatatcg ggacgttgcg tgcagatcaa gcacgnaagt gaagacgcgt gcattccttg | 360 |
| ccttccgtga acgantgccc agntcaagaa gancctgatg gaaccct | 407 |

<210> SEQ ID NO 112
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 112

| | | |
|---|---|---|
| tcgcggccga ggtcggccga ggtctgacat ctgttgtctg tgataaccac ttctgtattg | 60 |
| cgtcttaacc acttctgtat tgtgtggttt taactgccta aggcggcaat gggcagtggg | 120 |
| cccctttccc ttaggatggg tatcaattca acaatattta taaggcattt actgtgtgct | 180 |
| aagcatttgg aagacccagg ctacaaaata agacatagtt cctgccctcc aggccagcag | 240 |
| agggaggcac aaatacccag gaatctctga tgggtgtgaa gtgcggtcgt gggccacaga | 300 |
| aaatgaccgt catggagacc ctgctaaagg tcggaccctg agcccaaagg ggtattcaga | 360 |
| agnggagatg attttggccc cactcataga tgggtggcaa a | 401 |

<210> SEQ ID NO 113
<211> LENGTH: 451
<212> TYPE: DNA
<213> ORGANISM: Homo sapien

<400> SEQUENCE: 113

| | | |
|---|---|---|
| gtcgcggccg aggtccatat taaaaagtcc atcataaaca aagactcctc ctcatggtat | 60 |
| gaatatgctc catatgccca taatggtgca taacggactt agaaattcca atgagtctta | 120 |
| gggttgaaat ttccaatgac ctgagcaagg cagctcccta tagcttctgg ataacatttt | 180 |
| acacccagag ttcaggctta aacagaccta tcaacacaat tattttcgga ttgtctgtct | 240 |
| agaaaacggc aatgctcaaa ggaatataaa taagggtggg gggacatatg cttccagcct | 300 |
| ggcctttctc catgtggtaa aaaacaatgg aatggctgtg ttaattttt tttaatcttt | 360 |
| tctgaccttt actatgtttg gtaatggaaa taagtcaggg aaaacaaaat gaacaggtct | 420 |
| catcacttaa ttaatactgg gttttcttct t | 451 |

<210> SEQ ID NO 114
<211> LENGTH: 441
<212> TYPE: DNA
<213> ORGANISM: Homo sapien

<400> SEQUENCE: 114

| | | |
|---|---|---|
| ggccgcccgg gcaggtccat cctgtcagag atgggagaag tcacagacgg aatgatggat | 60 |
| acaaagatgg ttcactttct tacacactat gctgacaaga ttgaatctgt tcatttttca | 120 |
| gaccagttct ctggtccaaa aattatgcaa gaggaaggtc agcctttaaa gctacctgac | 180 |
| actaagagga cactgttgtt tacatttaat gtgcctggct caggtaacac ttacccaaag | 240 |
| gatatggagg cactgctacc cctgatgaac atggtgattt attctattga taaagccaaa | 300 |

```
aagttccgac tcaacagaga aggcaaacaa aaagcagata agaaccgtgc ccgagtagaa      360
gagaacttct tgaaacttga cacatgtgca aagacaggaa gcagcacagt ctcggcggga      420
ggaagaaaaa aagaacagag a                                                441

<210> SEQ ID NO 115
<211> LENGTH: 431
<212> TYPE: DNA
<213> ORGANISM: Homo sapien
<220> FEATURE:
<221> NAME/KEY: misc_feature
<222> LOCATION: (1)...(431)
<223> OTHER INFORMATION: n = A,T,C or G

<400> SEQUENCE: 115
gccgcccggg caggtccatt ggcggtgaca aaaggaaaag aagcaaagag actcagtcca       60
taatgctgat tagttagaag aaagggctag gattgagaaa gtaccaggaa cttttaatta      120
tttaaaagag aatgctgact gttaatgttt taaatcttac tgttcaaatg tactaatatg      180
aatttttacc ctttgtgcat gaatattcta acaactaga agacctccac aatttagcag       240
ttatgaaagt taaactttt attataaaaa ttctaaacct tactgctcct ttaccaggaa       300
catgacacac tatttancat cagttgcata cctcgccaat agtataattc aactgtcttg      360
cccgaacaat catctccatc tggaagacgt aagcctttag aaacacattt ttctattaat      420
ttctctagaa c                                                           431

<210> SEQ ID NO 116
<211> LENGTH: 421
<212> TYPE: DNA
<213> ORGANISM: Homo sapien

<400> SEQUENCE: 116
gtcgcggccg aggtccagaa atgaagaaga agtttgcaga tgtatttgca aagaagacga       60
aggcagagtg gtgtcaaatc tttgacggca cagatgcctg tgtgactccg gttctgactt      120
ttgaggaggt tgttcatcat gatcacaaca aggaaccggg gctcgtttat caccagtgag      180
gagcaggacg tgagcccccg ccctgcacct ctgctgttaa acaccccagc catcccttct      240
ttcaaaaggg atcctttcat aggagaacac actgaggaga tacttgaaga atttggattc      300
agcccgcgaa gagatttatc aagcttaact cagataaaat cattgaaagt aataaggtaa      360
aagctaagtc tctaacttcc aggcccacgg ctcaagtgaa tttcgaatac tgcatttaca      420
g                                                                      421

<210> SEQ ID NO 117
<211> LENGTH: 489
<212> TYPE: DNA
<213> ORGANISM: Homo sapien

<400> SEQUENCE: 117
agcgtggtcg cggccgaggt aaggctgcga ggttgtggtg tctgggaaac tccgaggaca       60
gagggctaaa tccatgaagt ttgtggatgg cctgatgatc cacagcggag accctgttaa      120
ctactacgtt gacactgctg tgcgccacgt gttgctcaga cagggtgtgc tgggcatcaa      180
ggtgaagatc atgctgccct gggacccaac tggtaagatt ggccctaaga agcccctgcc      240
tgaccacgtg agcattgtgg aacccaaaga tgagatactg cccaccaccc ccatctcaga      300
acagaagggt gggaagccag agccgcctgc catgccccag ccagtcccca cagcataaca      360
```

```
gggtctcctt ggcagacctg cccgggcggc cgctcgaaag cccgaattcc agcacactgg    420
cggccgttac tagtggatcc cagctcggta ccaagcttgg cgtaatcatg gtcatagctg    480
gtttcctgt                                                            489
```

<210> SEQ ID NO 118
<211> LENGTH: 489
<212> TYPE: DNA
<213> ORGANISM: Homo sapien

<400> SEQUENCE: 118

```
tcgagcggcc gcccgggcag gtattgaata cagcaaaatt ctatatacaa agtgacctgg    60
acctgctgct tcaaaacatg atcctttctt actaatatct tgatagtcgg tccatagagc    120
attagaaagc aattgactct aaataaaca gaaaagtgcc taatgcacat taaatgaatg     180
gcctaactac tggaacttta gtagttctat aaggtgatta acataggtag gatccagttc    240
ctatgacagg ctgctgaaga acagatatga gcatcaagag gccattttgt gcactgccac    300
cgtgatgcca tcgtgtttct ggatcataat gttcccatta tctgattcta gacacaccac    360
aggaatatca gtggggtcag aggttagctt agctgcttgc tgggctagaa cagatatcac    420
tccagcatgc tcatctgaca gggtcccgcg gcaacccaga ttaagtcctt gtgaatctgt    480
gcacaggga                                                            489
```

<210> SEQ ID NO 119
<211> LENGTH: 181
<212> TYPE: DNA
<213> ORGANISM: Homo sapien

<400> SEQUENCE: 119

```
taggttccag agacttttgg cccaggagga atatttactt ttagctctgg acatcattac    60
aaaaaggaat atttcccaaa cctcttcaga ccgagaatac atgggtaaaa ttattaaata    120
gttgtataat aaaaataatt ttttccttaa aaaaaaaaa accctcggcc gcgaccacgc     180
t                                                                    181
```

<210> SEQ ID NO 120
<211> LENGTH: 489
<212> TYPE: DNA
<213> ORGANISM: Homo sapien
<220> FEATURE:
<221> NAME/KEY: misc_feature
<222> LOCATION: (1)...(489)
<223> OTHER INFORMATION: n = A,T,C or G

<400> SEQUENCE: 120

```
gcgtggtcgc ggccgaggtc catttaaaac aaagaaaaat actaaagcca ctagtaaaca    60
tctgatgtgc aaaatacaac atcctctagt tggctttatg ccattattac ataagctcca    120
aatagctcat cttaaattaa aaagaaaaag tggctgtccc atctctgctg cataaatcag    180
attttttttt aaaggtttag agtactttaa ggaagggaag ttcaaaactg ccagtgaaat    240
tcacagagaa tacaaattta gcaatttaat ttcccaaagc tctttgaaga agcaagagag    300
tctctcttct taatgcagtg ttctcccaag aggaactgta attttgcttg gtacttatgc    360
tgggagatat gcaaaatgtg ttttttcaatg tttgctagaa tataatggtt cctcttcagt    420
gnctggttca tcctggaact catgggttaa gaaggacttc ttggagccga actgcccggg    480 cgggccntt                                                            489
```

<210> SEQ ID NO 121
<211> LENGTH: 531
<212> TYPE: DNA
<213> ORGANISM: Homo sapien

<400> SEQUENCE: 121

| | | | | | |
|---|---|---|---|---|---|
| cgagcggccg | cccgggcagg | tggccagcgc | tggtcccgca | gacgccgaga | tggaggaaat | 60 |
| atttgatgat | gcgtcacctg | gaaagcaaaa | ggaaatccaa | gaaccagatc | ctacctatga | 120 |
| agaaaaaatg | caaactgacc | gggcaaatag | attcgagtat | ttattaaagc | agacagaact | 180 |
| ttttgcacat | ttcattcaac | ctgctgctca | gaagactcca | acttcacctt | tgaagatgaa | 240 |
| accagggcgc | ccacgaataa | aaaagatga | gaagcagaac | ttactatccg | ttggcgatta | 300 |
| ccgacaccgt | agaacagagc | aagaggagga | tgaagagcta | ttaacagaaa | gctccaaagc | 360 |
| aaccaatgtt | tgcactcgat | ttgaagactc | tccatcgtat | gtaaaatggg | gtaaactgag | 420 |
| agattatcag | gtcccgagga | ttaaactggc | tcatttcttt | gtatgagaat | ggcatcaatg | 480 |
| gtatccttgc | agatgaaatg | ggcctaggaa | agactcttca | acaatttctc | t | 531 |

<210> SEQ ID NO 122
<211> LENGTH: 174
<212> TYPE: DNA
<213> ORGANISM: Homo sapien

<400> SEQUENCE: 122

| | | | | | |
|---|---|---|---|---|---|
| tcgagcggcc | gcccgggcag | gtctgccaac | agcagaggcg | gggcctccgg | catcttcaaa | 60 |
| gcacctctga | gcaggctcca | gccctctggc | tgcgggaggg | gtctggggtc | tcctctgagc | 120 |
| tcggcagcaa | agcagatgtt | atttctctcc | cgcgacctcg | gccgcgacca | cgct | 174 |

<210> SEQ ID NO 123
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 123

| | | | | | |
|---|---|---|---|---|---|
| agcgtggtcg | cggccgaggt | cctcaaccaa | gagggttgat | ggcctccagt | caagaaactg | 60 |
| tggctcatgc | cagcagagct | ctctcctcgt | ccagcaggcg | ccatgcaagg | gcaggctaaa | 120 |
| agacctccag | tgcatcaaca | tccatctagc | anagagaaaa | ggggcactga | agcagctatg | 180 |
| tctgccaggg | gctaggggct | cccttgcaga | cagcaatgct | acaataaagg | acacagaaat | 240 |
| gggggaggtg | gggaagccc | tattttata | acaaagtcaa | acagatctgt | gccgttcatt | 300 |
| cccccagaca | cacaagtaga | aaaaaaccaa | tgcttgtggt | ttctgccaag | atggaatatt | 360 |
| cctccttcct | aanttccaca | catggccgtt | tgcaatgctc | gacagcattg | cactgggctg | 420 |
| cttgtctctg | tggtctgggc | accagtagct | tgggccccat | atacacttct | cagttcccac | 480 |
| anggcttatg | gccnangggc | angctccaat | tttcaagcac | cacgaaggaa | g | 531 |

<210> SEQ ID NO 124
<211> LENGTH: 416
<212> TYPE: DNA
<213> ORGANISM: Homo sapien

<400> SEQUENCE: 124

| | | | | | |
|---|---|---|---|---|---|
| tcgagcggcc | gcccgggcag | gtccatctat | actttctaga | gcagtaaatc | tcataaattc | 60 |

| acttaccaag cccaggaata atgactttta aagccttgaa tatcaactaa gacaaattat | 120 |
| gccaattctg atttctcaca tatacttaga ttacacaaag ataaagcttt agatgtgatc | 180 |
| attgtttaat gtagacttat ctttaaagtt tttaattaaa aactacagaa gggagtaaac | 240 |
| agcaagccaa atgatttaac caaatgattt aagagtaaaa ctcactcaga aagcattata | 300 |
| cgtaactaaa tatacatgag catgattata tacatacatg aaactgcaat tttatggcat | 360 |
| tctaagtaac tcatttaagt acatttttgg catttaaaca aagatcaaat caagct | 416 |

<210> SEQ ID NO 125
<211> LENGTH: 199
<212> TYPE: DNA
<213> ORGANISM: Homo sapien
<220> FEATURE:
<221> NAME/KEY: misc_feature
<222> LOCATION: (1)...(199)
<223> OTHER INFORMATION: n = A,T,C or G

<400> SEQUENCE: 125

| agcgtggtcg cggccgaggt gcttttttt ttttttttt tttttttttt gctattctaa | 60 |
| aggggaaggc ccctttttat taaacttgta cattttactt tccttctttc anaatgctaa | 120 |
| taaaaaactt ttgtttatac ttaaaaaaac cataaatcan acaaacaaaa gaaacgattc | 180 |
| caacatcact tctgngatg | 199 |

<210> SEQ ID NO 126
<211> LENGTH: 490
<212> TYPE: DNA
<213> ORGANISM: Homo sapien

<400> SEQUENCE: 126

| cgtggtcgcg gccgaggtcc agttgctcta agtggattgg atatggttgg agtggcacag | 60 |
| actggatctg ggaaaacatt gtcttatttg cttcctgcca ttgtccacat caatcatcag | 120 |
| ccattcctag agagaggcga tgggcctatt tgtttggtgc tggcaccaac tcgggaactg | 180 |
| gcccaacagg tgcagcaagt agctgctgaa tattgtagag catgtcgctt gaagtctact | 240 |
| tgtatctacg gtggtgctcc taagggacca caaatacgtg atttggagag aggtgtggaa | 300 |
| atctgtattg caacacctgg aagactgatt gactttttag agtgtggaaa aaccaatctg | 360 |
| agaagaacaa cctaccttgt ccttgatgaa gcagatagaa tgcttgatat gggctttgaa | 420 |
| ccccaaataa ggaagattgt ggatcaaata agacctgata ggcaaactct aatgtggagt | 480 |
| gcgacttggc | 490 |

<210> SEQ ID NO 127
<211> LENGTH: 490
<212> TYPE: DNA
<213> ORGANISM: Homo sapien

<400> SEQUENCE: 127

| cgtggtcgcg gccgaggtcg gccgaggtct ggagatctga gaacgggcag actgcctcct | 60 |
| caagtgggtc cctgacccct gaccccgag cagcctaact gggaggcacc cccagcagg | 120 |
| ggcacactga cacctcacac ggcagggtat ccaacagac ctgaagctga gggtcctgtc | 180 |
| tgttagaagg aaaactaaca agcagaaagg acagccacat caaaaaccca tctgtacatc | 240 |
| accatcatca aagaccaaaa gtaaataaaa ccacaaagat gggaaaaaaa cagaacagaa | 300 |
| aaactggaaa ctctaaaaag cagagcacct ctcctcttcc aaaggaacgc agttcctcac | 360 |
| cagcaatgga acaaagctgg atggagaatg actttgacga gctgagaaaa gaacgcttca | 420 |

```
gacgatcaaa ttactctgag ctacgggagg acattcaaac caaaggcaaa gaagttgaaa      480
actttgaaaa                                                             490
```

<210> SEQ ID NO 128
<211> LENGTH: 469
<212> TYPE: DNA
<213> ORGANISM: Homo sapien
<220> FEATURE:
<221> NAME/KEY: misc_feature
<222> LOCATION: (1)...(469)
<223> OTHER INFORMATION: n = A,T,C or G

<400> SEQUENCE: 128

```
cgtggtcgcg gccgaggtgc ttttttttt ttttttttt ttttttttt tgctgattta          60 tttttctnt  ttattgttac atacaatgta taaacacata aaacanaaaa cagtagggat      120
cctctaggat ctctagggan acagtaaagt anaaagaggg ctcanaaaca tttttttaaa     180
gtacaagaca ttcagngctc ggcccaaagg cgtaaaagt ttanagccag canatagctg     240
nactaaaggc tccgtctntn tccccanagc caggacaacc ccaggagct ntccattagc     300 agccagtcca cgcaggcagg atgctgcgga aaagctcta tgctganaac attccccttg     360
atggaaagaa gggcaacaca aaaggggtaa ctaanagctc cttcctctcg tgagggcgac    420
aactgaggaa cagaaaagga gtgtcccatg tcacttttga cccctccc                 469
```

<210> SEQ ID NO 129
<211> LENGTH: 419
<212> TYPE: DNA
<213> ORGANISM: Homo sapien

<400> SEQUENCE: 129

```
gcgtggtcgc ggccgaggtc tgattttcat ttaaatattt cagagctata gcatttgcct      60
ccatgctcaa atccacacca ttggggctta agccgctcat gccaacatta gcaaatgaca    120
tgcagtttaa tccagagatc actgcttctg ggctgatgca tgccaacaca ctggcgtgat    180
ccacgttatg tgcattttc ttcactttag tgggagaatc aatttttact ccaaggcttc     240
ttagttgctt aagagttgca ttaaggacac aatctttgtc caccagtctt gaatgatgtg    300
tttttttctt tgtatggtaa acgttttggg ttctggtgca ttcatgactg ataattactg    360
ctttggtaga cggctgctca agtttccttg gaggaactat ttaataggtg ggttacttg     419
```

<210> SEQ ID NO 130
<211> LENGTH: 354
<212> TYPE: DNA
<213> ORGANISM: Homo sapien

<400> SEQUENCE: 130

```
agcgtggtcg cggccgaggt ccatctgagg agataaccac atcactaaca aagtgggagt      60
gaccccgcag agcacgctgt ggaattccat agttggtctc atccctggtc agtttccaca    120
tgatgatggt cttatctcga gaggcggaga ggatcatgtc cgggaactgc ggggtagtag    180
cgatctgggt tacccagccg ttgtggccct tgagggtgcc acgaagggtc atctgctcag    240
tcatggcggc ggcgagagcg tgtgtcgctg cagcgacgag gatggcactg gatggcttag    300
agaaactagc accacaacct ctcctgccgc acctgcccgg gcggcccgct cgaa          354
```

<210> SEQ ID NO 131
<211> LENGTH: 474
<212> TYPE: DNA

<213> ORGANISM: Homo sapien
<220> FEATURE:
<221> NAME/KEY: misc_feature
<222> LOCATION: (1)...(474)
<223> OTHER INFORMATION: n = A,T,C or G

<400> SEQUENCE: 131

| | | | | | |
|---|---|---|---|---|---|
| cgagcggccg | cccgggcagg | tctggcagca | gcttcctctg | gaataattga | cagctttgtg | 60 |
| ctgcctgact | aaaatttgaa | atgacaaccg | ctgaatgtaa | aatgatgtac | ctacaatgag | 120 |
| agagatttag | gaatactatc | tgtcaatcca | tagatgtaga | aacaaaacaa | actacagaat | 180 |
| gaaaacaaac | ttattttaaa | ccaaagaaac | aaatgtatcc | aaaatatagt | ccatgatata | 240 |
| tttgattact | agtataacca | cagttgaaaa | cttaaaaaaa | aaaattgaca | ttttttgtaa | 300 |
| tgggtactaa | tggatttata | aaaggtttct | gtttccaaag | atgttattgg | ggtccacata | 360 |
| ttccttgaag | acttcagcat | cccaaagccc | gacatcagag | atactttcct | ttagccattg | 420 |
| nttcccgtaa | cttgcccact | ccatggtgat | gtgacaggct | tcccttcatt | agca | 474 |

<210> SEQ ID NO 132
<211> LENGTH: 474
<212> TYPE: DNA
<213> ORGANISM: Homo sapien
<220> FEATURE:
<221> NAME/KEY: misc_feature
<222> LOCATION: (1)...(474)
<223> OTHER INFORMATION: n = A,T,C or G

<400> SEQUENCE: 132

| | | | | | |
|---|---|---|---|---|---|
| ggccgaggtg | gggaattcat | gtggaggtca | gagtggaagc | aggtgtgaga | gggtccagca | 60 |
| gaaggaaaca | tggctgccaa | agtgtttgag | tccattggca | agtttggcct | ggccttagct | 120 |
| gttgcaggag | gcgtggtgaa | ctctgcctta | tataatgtgg | atgctgggca | cagagctgtc | 180 |
| atctttgacc | gattccgtgg | agtgcaggac | attgtggtag | gggaagggac | tcattttctc | 240 |
| atcccgtggg | tacagaaacc | aattatcttt | gactgccgtt | ctcgaccacg | taatgtgcca | 300 |
| gtcatcactg | gtagcaaaga | tttacagaat | gtcaacatca | cactgcgcat | cctcttccgg | 360 |
| cctgtcgcca | gccagcttcc | tcgcatcttc | accagcatcg | ganaggacta | tgatgaaccg | 420 |
| tgtgctgccg | tccatcacaa | ctgagatcct | caagtcagtg | gtggctcgct | ttga | 474 |

<210> SEQ ID NO 133
<211> LENGTH: 387
<212> TYPE: DNA
<213> ORGANISM: Homo sapien

<400> SEQUENCE: 133

| | | | | | |
|---|---|---|---|---|---|
| tgctcgagcg | gccgccagtg | tgatggatat | ctgcagaatt | cggcttagcg | tggtcgcggc | 60 |
| cgaggtctgc | gggcccctta | gcctgccctg | cttccaagcg | acggccatcc | cagtaggga | 120 |
| ctttcccaca | ctgtgccttt | acgatcagcg | tgacagagta | gaagctggag | tgcctcacca | 180 |
| cacggcccgg | aaacagcggg | aagtaactgg | aaagagcttt | aggacagctt | agatgccgag | 240 |
| tgggcgaatg | ccagaccaat | gatacccaga | gctacctgcc | gccaacttgt | tgagatgtgt | 300 |
| gtttgactgt | gagagagtgt | gtgtttgtgt | gtgtgttttg | ccatgaactg | tggccccagt | 360 |
| gtatagtgtt | tcagtggggg | agaactg | | | | 387 |

<210> SEQ ID NO 134
<211> LENGTH: 401
<212> TYPE: DNA
<213> ORGANISM: Homo sapien

<400> SEQUENCE: 134

```
ggccgcccgg gcaggtctga tgaagaacac gggtgtgatc cttgccaatg acgccaatgc    60
tgagcggctc aagagtgttg tgggcaactt gcatcggctg ggagtcacca acaccattat   120
cagccactat gatgggcgcc agttccccaa ggtggtgggg ggctttgacc gagtactgct   180
ggatgctccc tgcagtggca ctggggtcat ctccaaggat ccagccgtga agactaacaa   240
ggatgagaag gacatcctgc gcttgtgctc acctccagaa ggaagttgct cctgagtgct   300
attgactctt gtcaatgcga ccttcaagac aggaggctac ctggtttact gcacctgttc   360
tatcacagtg agacctctgc catggcagaa caggggaagc t                      401
```

<210> SEQ ID NO 135
<211> LENGTH: 451
<212> TYPE: DNA
<213> ORGANISM: Homo sapien

<400> SEQUENCE: 135

```
ggtcgcggcc gaggtctgtt cctgagaaca gcctgcattg aatctacag agaggacaac    60
taatgtgagt gaggaagtga ctgtatgtgg actgtggaga aagtaagtca cgtgggccct   120
tgaggacctg gactgggtta ggaacagttg tactttcaga ggtgaggtgt cgagaaggga   180
aagtgaatgt ggtctggagt gtgtccttgg ccttggctcc acagggtgtg ctttcctctg   240
gggccgtcag ggagctcatc ccttgtgttc tgccagggtg gggtaccggg gtttgacact   300
gaggagggta acctgctggc tggagcggca gaacagtggc cttgatttgt cttttggaag   360
atttttaaaaa ccaaaaagca taaacattct ggtccttcac aatgctttct ctgaagaaat   420
acttaacgga aggacttctc cattcaccat t                                  451
```

<210> SEQ ID NO 136
<211> LENGTH: 411
<212> TYPE: DNA
<213> ORGANISM: Homo sapien

<400> SEQUENCE: 136

```
ggccgcccgg gcaggtctga atcacgtaga atttgaagat caagatgatg aagccagagt    60
tcagtatgag ggttttcgac ctgggatgta tgtccgcgtt gagattgaaa atgttccctg   120
tgaatttgtg cagaactttg acccccttta ccccattatc ctgggtggct ggggcaacag   180
tgagggaaat gttggacatg tgcaggtggg tccctttgct gcgtatttgg tgcctgaggc   240
tctgtggatt tccctccat caatcatctt accctctcat cccctcaga tgcgtctgaa     300
gaaacatctc tggtataaga aaatcctcaa gtcccaagat ccaatcatat tttctgtagg   360
gtggaggaag tttcagacca tcctgctcta ttatatccga agaccacaat g             411
```

<210> SEQ ID NO 137
<211> LENGTH: 211
<212> TYPE: DNA
<213> ORGANISM: Homo sapien
<220> FEATURE:
<221> NAME/KEY: misc_feature
<222> LOCATION: (1)...(211)
<223> OTHER INFORMATION: n = A,T,C or G

<400> SEQUENCE: 137

```
cggccgcccg gcaggtcgg ttggtgcggc ctccattgtt cgtgttttaa ggcgccatga     60
ggggtgacag aggccgtggt cgtggtgggc gctttggttc cagaggaggc ccaggaggag   120
```

| | |
|---|---|
| ggttcaggcc ctttgcacca catatcccat ttgacttcta tttgtgtgaa atggcctttc | 180 |
| cccggntcaa gccagcacct cgatgaaact t | 211 |

<210> SEQ ID NO 138
<211> LENGTH: 471
<212> TYPE: DNA
<213> ORGANISM: Homo sapien

<400> SEQUENCE: 138

| | |
|---|---|
| gccgcccggg caggtctggg ctggcgactg gcatccaggc cgtaactgca aatctatgct | 60 |
| aggcgggtc tcccttctgt gtgttcaagt gttctcgact tggattctta actattttaa | 120 |
| aaaatgcact gagtttgggt taaaaaccaa ccaccaaaat ggatttcaac acagctctaa | 180 |
| agccaagggc gtggccggct ctcccaacac agcgactcct ggaggccagg tgcccatggg | 240 |
| cctacatccc ctctcagcac tgaacagtga gttgattttt cttttttacaa taaaaaaagc | 300 |
| tgagtaatat tgcataggag taccaagaaa ctgcctcatt ggaaacaaaa actatttaca | 360 |
| ttaaataaaa agcctggccg caggctgcgt ctgccacatt tacagcacgg tgcgatgcac | 420 |
| acggtgacca aaccacggag gcaagcttct ggcactcaca ccacgacccg c | 471 |

<210> SEQ ID NO 139
<211> LENGTH: 481
<212> TYPE: DNA
<213> ORGANISM: Homo sapien
<220> FEATURE:
<221> NAME/KEY: misc_feature
<222> LOCATION: (1)...(481)
<223> OTHER INFORMATION: n = A,T,C or G

<400> SEQUENCE: 139

| | |
|---|---|
| gtcgcggccg aggtctgttc tttagctcag atttaaacct gctgtctctt ctttatttgc | 60 |
| agaatgaatt cccagttcct gagcagttca agacccctatg gaacgggcag aagttggtca | 120 |
| ccacagtgac agaaattgct ggataagcga agtgccactg ggttctttgc cctcccttca | 180 |
| caccatggga taaatctgta tcaagacggt tcttttctag atttcctcta cctttttgct | 240 |
| cttaaaactg cttctctgct ctgagaagca cagctacctg ccttcactga aatatacctc | 300 |
| aggctgaaat ttggggtggg atagcaggtc agttgatctt ctgcaggaag gtgcagcttt | 360 |
| tccatatcag ctcaaccacg ccgncagtcc attcttaagg aactgccgac taggactgat | 420 |
| gatgcatttt agcttttgag cttttggggg gtattctacc aaccaacagt ccatttggaa | 480 |
| a | 481 |

<210> SEQ ID NO 140
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 140

| | |
|---|---|
| gtcgcggccg aggtttccca tttaagaaaa atagatcttg agattctgat tcttttccaa | 60 |
| acagtcccct gctttcatgt acagcttttt ctttaccttta cccaaaattc tggccttgaa | 120 |
| gcagttttcc tctatggctt tgccttttctg attttctcag aggctcgagt ctttaatata | 180 |
| acccaaatg aaagaaccaa ggggaggggt gggatggcac ttttttttgt tggtcttgtt | 240 |
| ttgttttgtt ttttggttgg ttgggttccg ttattttta agattagcca ttctctgctg | 300 |

```
ctatttccct acataatgtc aattttttaac cataattttg acatgattga gatgtacttg    360 aggcttttt gntttaattg agaaaagact ttgcaattt ttttttagga tgagcctctc     420
c                                                                     421
```

<210> SEQ ID NO 141
<211> LENGTH: 242
<212> TYPE: DNA
<213> ORGANISM: Homo sapien
<220> FEATURE:
<221> NAME/KEY: misc_feature
<222> LOCATION: (1)...(242)
<223> OTHER INFORMATION: n = A,T,C or G

<400> SEQUENCE: 141

```
cgantngccc gcccgggcan gtctgtctaa ntttntcang gaccacgaac agaaactcgt    60
gcttcaccga anaacaatat cttaaacatc gaanaattta aatattatga aaaaaaacat   120
tgcaaaatat aaaataaata nnaaaaggaa aggaaacttt gaaccttatg taccgagcaa   180
atccaggtct agcaaacagt gctagtccta nattacttga tntacaacaa cacatgaata   240
ca                                                                 242
```

<210> SEQ ID NO 142
<211> LENGTH: 551
<212> TYPE: DNA
<213> ORGANISM: Homo sapien
<220> FEATURE:
<221> NAME/KEY: misc_feature
<222> LOCATION: (1)...(551)
<223> OTHER INFORMATION: n = A,T,C or G

<400> SEQUENCE: 142

```
agcgtggtcg cggcncgang tccacagggc anatattctt ttagtgtctg gaattaaaat    60
gtttgaggtt tangtttgcc attgtctttc caaaaggcca aataattcan atgtaaccac   120
accaagtgca aacctgtgct ttctatttca cgtactgttg tccatacagt tctaaataca   180
tgtgcagggg attgtagcta atgcattaca cagtcgttca gtcttctctg cagacacact   240
aagtgatcat accaacgtgt tatacactca actagaanat aataagcttt aatctgaggg   300
caagtacagt cctgacaaaa gggcaagttt gcataataga tcttcgatca attctctctc   360
caagggcccc gcaactaggc tattattcat aaaacacaac tgaanagggg attggtttta   420
ctggtaaatc atgtgntgct aaatcatttt ctgaacagtg gggtctaaat cantcattga   480
tttagtggca gccacctgcc cggcggccgn tcgaagccca attctgcaga tatccatcac   540
actggcggcc g                                                       551
```

<210> SEQ ID NO 143
<211> LENGTH: 515
<212> TYPE: DNA
<213> ORGANISM: Homo sapien
<220> FEATURE:
<221> NAME/KEY: misc_feature
<222> LOCATION: (1)...(515)
<223> OTHER INFORMATION: n = A,T,C or G

<400> SEQUENCE: 143

```
cgagnggccc gcccgggcag gtatcttcac aaactcaaca aaggcactac atgagacttc    60
acattcccct agtccaatag ctgacaaatt tttgcaacgt tctgcaatgc gaattaactc   120
ttcatcaagt ggccgtaatc catttgcaca cactactagt tcaaccagtc tagggcatgt   180
```

```
cattcccaca cggccaagca catctttgct tactgatctc ccaaagtaca gatgggtggc    240
aggtatttca tagcgaaaga aggggtcaaa ttcttcttca tataanaaaa aatacatcac    300
taagttcact ttgggtgaat gtctgatgaa agcatcccag ctactcttct gaatagtatg    360
gaagtgtgtc tgtccaggat tctcactgac tacatcaatg cgcaaatgtt ctaatcgaac    420
atgtttttca gaagacaatg caagtaacaa ctcatcactc aataagtggt aagttcaggg    480
ctagttctct taagccgnga cactgatcag cacac                               515

<210> SEQ ID NO 144
<211> LENGTH: 247
<212> TYPE: DNA
<213> ORGANISM: Homo sapien
<220> FEATURE:
<221> NAME/KEY: misc_feature
<222> LOCATION: (1)...(247)
<223> OTHER INFORMATION: n = A,T,C or G

<400> SEQUENCE: 144
tgcattctct ntggatgcan acctgcccgt tggtagggac tntgctcaca cggaacatgg     60
acggttacac ctgtgccgtg ggtgacgtcc accagcttct ggatcatctc ggcgngggtg    120
ttgtggaagg gcagactatc cacctccatg cncacgatgc ccganacgcc actccggact    180
ntgtgctgca ccaanatgcc cagcattnta tcttcaagca nagcacttat cagggtcctt    240
ggcacac                                                              247

<210> SEQ ID NO 145
<211> LENGTH: 309
<212> TYPE: DNA
<213> ORGANISM: Homo sapien
<220> FEATURE:
<221> NAME/KEY: misc_feature
<222> LOCATION: (1)...(309)
<223> OTHER INFORMATION: n = A,T,C or G

<400> SEQUENCE: 145
cgtgggtcgc ggcccgangt ctgctgtaac aaaacaccat agtctgggca gctcatagac     60
aatggaattt tatttctcac gcttctggag gctggattcc aagatcaagg ttccaggaga    120
ctcagtgtct ggcaaggtct cggtttctgc ctcanagatg gtgccatctg gctgtgtcct    180
cacaagtagg aaggtgcaag aagctcccct caggctctgt ctgtaagaca ctgatcccat    240
tcatganggg gaaacgtaat gacctaatca gcccccagag accccacttc taacaccatc    300
accttgggg                                                            309

<210> SEQ ID NO 146
<211> LENGTH: 486
<212> TYPE: DNA
<213> ORGANISM: Homo sapien
<220> FEATURE:
<221> NAME/KEY: misc_feature
<222> LOCATION: (1)...(486)
<223> OTHER INFORMATION: n = A,T,C or G

<400> SEQUENCE: 146
agcgtgggtc gcggcncgac gtcctgtcca tatttcacag cccgagaact aatacaagat     60
gctgacatca tattttgtcc ctacaactat cttctanatg cacaaataag ggaaagtatg    120
gatttaaatc tgaaagaaca ggttgtcatt ttanatgaag ctcataacat cgaggactgt    180
gctcgggaat cagcaagtta cagtgtaaca gaagttcagc ttcggtttgc tcgggatgaa    240
ctanatagta tggtcaacaa taatataagg aaganagatc atgaacccct acgagctgtg    300
```

```
tgctgtagcc tcattaattg gntagaagca aacgctgaat atcttgnana angagantat      360
gaatcagctt gtaaaatatg gagtggaaat gaaatgctct taactttaca caaaatgggt     420
atcaccactg ctactttttcc cattttgcng gtaagatatn ttttctacct gngaaacgta    480
tttaag                                                                 486
```

<210> SEQ ID NO 147
<211> LENGTH: 430
<212> TYPE: DNA
<213> ORGANISM: Homo sapien
<220> FEATURE:
<221> NAME/KEY: misc_feature
<222> LOCATION: (1)...(430)
<223> OTHER INFORMATION: n = A,T,C or G

<400> SEQUENCE: 147

```
gccgcccggg cangttcgac attacntnga gttccatgat gtacaattct ttcacgaaaa     60
acaatgaatg caagaatttg aggatctcct tactcctccc ttttacagat ggtctctcaa    120
tcccttcttc ttcctcttca tcttcatctt cttctgaacg cgctgccggg taccacggct    180
ttctttgtct ttatcgtgag atgaaggtga tgcttctgtt tcttctacca taactgaaga   240
aatttcgctg caagtctctt gactggctgt ttctccgact tcgccttnt gtcaaacgng    300 agtcttttta cctcatgccc ctcagcttca cagcatcttc atctggatgt tnatttctca    360
aagggctcac tgaggaaact tctgattcan atgtcgaana gcactgtgaa gttttctctt   420
cattttgctg                                                           430
```

<210> SEQ ID NO 148
<211> LENGTH: 483
<212> TYPE: DNA
<213> ORGANISM: Homo sapien
<220> FEATURE:
<221> NAME/KEY: misc_feature
<222> LOCATION: (1)...(483)
<223> OTHER INFORMATION: n = A,T,C or G

<400> SEQUENCE: 148

```
cccgggcagg tctgtgttgn tttncaaccg gtgtcctccc cagcgtccag aananggaaa     60
tgtggagcgg gtgatgatga cccctcgctg tcctgtcacc tcctgcacag cttcgtatgt    120
gggtctggtc tgggaccacc cgtacaggtt gtgcacgttg tagtgctcca cgggggagct    180
gtccggcagg atctgctgac tctccatgca cagagtcttg ctgctcaggc ccttgtccct   240
agattccaaa tatggcatat agggtggggt tatttagcat ttcattgctg cagcccctga   300
cagatccatc cacaaaattt gatggctcat tcatatcaat ccacaatcca tcaaacttca   360
agctcttctc tggntctcga nggtttgcat agaactcttc tatctctttc ttccaccacg    420
canacctcgg ncgcgaccac gctaagccga attctgcana tatccatcac actggcggcc    480
gct                                                                   483
```

<210> SEQ ID NO 149
<211> LENGTH: 439
<212> TYPE: DNA
<213> ORGANISM: Homo sapien
<220> FEATURE:
<221> NAME/KEY: misc_feature
<222> LOCATION: (1)...(439)
<223> OTHER INFORMATION: n = A,T,C or G

<400> SEQUENCE: 149

| | |
|---|---|
| ctttcacgaa nacaatgaat gcaagaattt gaggatctcc ttactcctcc cttttacaga | 60 |
| tggtctctca atcccttctt cttcctcttc atcttcatct tcttctgaac gcgctgccgg | 120 |
| gtaccacggc tttctttgtc tttatcgtga gatgaaggtg atgcttctgt ttcttctacc | 180 |
| ataactgaag aaatttcgct gcaagtctct tgactggctg tttctccgac ttcgcctttt | 240 |
| tgcaaacgtg agtcttttta cctcatgccc ctcagcttcc acagcatctt catctggatg | 300 |
| ttcatttctc aaagggctca ctgaggaaac ttctgactca catgtcgaag aagcactgng | 360 |
| agtttctctt catttgctgc aaanttgctc tttgctggct gngctctcag accacccatt | 420 |
| tggctgcatg ggggctgac | 439 |

<210> SEQ ID NO 150
<211> LENGTH: 578
<212> TYPE: DNA
<213> ORGANISM: Homo sapien
<220> FEATURE:
<221> NAME/KEY: misc_feature
<222> LOCATION: (1)...(578)
<223> OTHER INFORMATION: n = A,T,C or G

<400> SEQUENCE: 150

| | |
|---|---|
| ggcncgcccg ggcangtcca ctccacttttt gagctctgag ggaataccttt caggagggac | 60 |
| agggtcaggg agtcctggca gctccgcagc agagattcac attcattcag agacttgttg | 120 |
| tccagtgcaa tgccattgat cgcaacgatc ctgtctccca cagcaaggga cccttctttta | 180 |
| gcggcagggc ttccaggcag cacagcggca gcatacactc cattctccag actgatgcca | 240 |
| ctgtctttct gtccactgan gttgatgtgc agcggcgtga ccaccttccc acccagggac | 300 |
| ttcctccgcc gcacgaccat gttgatgggc ccctncccca ttgaggagcg ccttgatggc | 360 |
| ctgcttcttg nccttggtga tgaagtccac atcggtgatt ctcacagcca gtcattgacc | 420 |
| cttaagcggn catcagcaat gcttcctttg gccactttag ngacaaatat gccacagtcc | 480 |
| ccgggaaaca agggtcattc acaccttctg gcatatcaaa cacctcggcc gggancacta | 540 |
| agccgaattc tgcagatatc catcacactg gngggccg | 578 |

<210> SEQ ID NO 151
<211> LENGTH: 503
<212> TYPE: DNA
<213> ORGANISM: Homo sapien
<220> FEATURE:
<221> NAME/KEY: misc_feature
<222> LOCATION: (1)...(503)
<223> OTHER INFORMATION: n = A,T,C or G

<400> SEQUENCE: 151

| | |
|---|---|
| cgagcggccc gcccgggcag gtctgggaga tcagcgactg ctgccacgtg cccagaaatg | 60 |
| gctcgtcctt tcactacagc ggaatgcaat gagggtgggt gagaagatga tgggtcggtt | 120 |
| atttcattcc tttttctttt acaacttcac tttcagagac ttcagcgttc catgtctgct | 180 |
| gtgctgtgga acccagagtg ctcttgcctg gatggctgag aatcccttgg accctggaag | 240 |
| cacctactcc atgatggccc ggtatagtgc aggctcaata taatcttccc ggtatcttga | 300 |
| gttgataact cgttgccgtt tcttttcttg cttaacctct ttctctgtga aaatctcatt | 360 |
| gaagcgcatg tctgaagcta ctgacagtct anatttgact ctcttgggaa gctcttcatc | 420 |
| cagtgtgtat acatcatctc tcttaaccac aagttggagc catncttaaa cttcacctgg | 480 |
| tacatttgga tagggtggga ggc | 503 |

<210> SEQ ID NO 152
<211> LENGTH: 553
<212> TYPE: DNA
<213> ORGANISM: Homo sapien
<220> FEATURE:
<221> NAME/KEY: misc_feature
<222> LOCATION: (1)...(553)
<223> OTHER INFORMATION: n = A,T,C or G

<400> SEQUENCE: 152

| | | | | |
|---|---|---|---|---|
| agcgtggtcg | cggcccgagg | tccactgagc | tccgccttcc | ccgggctccc tgaggaagca | 60 |
| gagtcctgac | ttccaggaag | gacaggacac | agaggcaaga | actcagcctg tgaggctctg | 120 |
| ggtggctcct | gaggccagag | gacgccttcc | gcgatccatg | gctcagcatc gtccttctgg | 180 |
| cttcccagcc | ccgggccgaa | cgttcgggtt | aataagcaga | gcagttattc ggctcctggc | 240 |
| aggagctccc | ccgttagttt | ccacgttgtg | agcacattca | tacttaagac tgnttctctt | 300 |
| tgtgttttaa | gcgtctgtct | ctgtagtaaa | ctgaaatgtt | aacagaaatg cagacctgcc | 360 |
| cgggcggccg | ctcgaaagcc | gaattctgca | gatatccatc | acactggcgg ccgctcgagc | 420 |
| atgcatctag | anggcccaat | tcgccctata | gtgagtcgna | ttacaattca ctgggccgcg | 480 |
| ntttacaacg | tcgtgactgg | gaaaaccctg | gcgtacccac | ttaatcgcct tgcagnacat | 540 |
| ccccctttcg | cca | | | | 553 |

<210> SEQ ID NO 153
<211> LENGTH: 454
<212> TYPE: DNA
<213> ORGANISM: Homo sapien
<220> FEATURE:
<221> NAME/KEY: misc_feature
<222> LOCATION: (1)...(454)
<223> OTHER INFORMATION: n = A,T,C or G

<400> SEQUENCE: 153

| | | | | |
|---|---|---|---|---|
| tcgagcggct | cgcccgggca | ggtccaccta | gcatggctcc | tctaaacacg caactcagcg | 60 |
| aggggacccc | cttcacctct | ggcaagagag | ctgggtagat | cagaaacttg gtgacacctg | 120 |
| gctagcacag | agcaggctca | cttgtcttgg | tcccactacc | cagattcctg cagacattgc | 180 |
| aaaccaaatg | aaggttgntg | aatgacccct | gtccccagcc | acttgttttg gtatcatctg | 240 |
| ctctgcagtg | gaatgcctgt | gtgtttgagt | tcactctgca | tctgtatatt tgagtataga | 300 |
| aaccgantca | agtgatctgt | gcatncagac | acactggggc | acctgancac agaacaaatc | 360 |
| accttaacga | tctggaatga | aactgnganc | antgcccgcc | tgggtgggtc tgganaaact | 420 |
| gccgncttct | tgttggacct | tggccgcacc | acct | | 454 |

<210> SEQ ID NO 154
<211> LENGTH: 596
<212> TYPE: DNA
<213> ORGANISM: Homo sapien
<220> FEATURE:
<221> NAME/KEY: misc_feature
<222> LOCATION: (1)...(596)
<223> OTHER INFORMATION: n = A,T,C or G

<400> SEQUENCE: 154

| | | | | |
|---|---|---|---|---|
| agcgtggtcg | cggcccgang | gcggcctcct | gantganggg | aagggacgtg ggggcggcca | 60 |
| cggcaggatt | aacctccatt | tcagctaatc | atgggagaga | ttaaagtctc tcctgattat | 120 |
| aactggttta | naggtacagt | tccccttaaa | aagattattg | tggatgatga tgacagtaag | 180 |
| atatggtcgc | tctatgacgc | gggcccccga | agtatcaggt | gtcctctcat attcctgccc | 240 |

```
cctgtcagtg gaactgcaga tgtcttttc cggcagattt tggctctgac tggatggggt      300
taccgggtta tcgctttgca gtatccagtt tattgggacc atctcgagtt cttgtgatgg      360
attcacaaaa cttttanacc atttacaatt ggataaagtt catcttttg gcgcttcttt       420 gggangcttt ttggcccana aatttgctga atacactcac aaatctccta gaagccattc      480
cctaatcctc tgcaattcct tcagngacac ctctatcttc aaccaacttg gactggaaac      540
agctttggct gatgcctgca tttatgctca aaaatagtt cttggaaatt ttcatc          596
```

<210> SEQ ID NO 155
<211> LENGTH: 343
<212> TYPE: DNA
<213> ORGANISM: Homo sapien
<220> FEATURE:
<221> NAME/KEY: misc_feature
<222> LOCATION: (1)...(343)
<223> OTHER INFORMATION: n = A,T,C or G

<400> SEQUENCE: 155

```
ctcganttgg cncgcccggg cangtctgcc tggttttga ccgngcgagc tatttagnct       60
ctggctctgt ttccggagct caaggnaaaa atcttgaana actcgagcag cttctgtgga      120
tagccttggg tacacatact gccgagcata gccaatgtac tttctcaata gctggtgggg      180
aatgggatct attgtttctc caggaaccac ctttagtctt tctgataatg gcttctcaga      240
aactacttca agtacggaag tatttgaatc ttgactatnc atacgagcta ctgtggcact      300
gctaatgggn tctctgctnt ccagctctta ttgcaatcac atg                      343
```

<210> SEQ ID NO 156
<211> LENGTH: 556
<212> TYPE: DNA
<213> ORGANISM: Homo sapien
<220> FEATURE:
<221> NAME/KEY: misc_feature
<222> LOCATION: (1)...(556)
<223> OTHER INFORMATION: n = A,T,C or G

<400> SEQUENCE: 156

```
tcgagcggcc cgcccgggca ggtctggcac cacncagatc gattaactgg ctcatctgat      60
ctcgtggccc ccaccctgga actgacttag cacaaaagga cacctcaatt ccttatgatt      120
tcatctccga cccaaccaat caacacccctt gactcactgg ccttcccct cccaccaaat      180 tatccttaaa aactctgatc cccgaatgct cagggagatc gatttgagta ctaataagac      240
tccagtctcc tgcacaagca gctctgtgta ctcttcctct attgcaattc ctgtcttgat      300
aaatcggctc tgtgtaggcg gcggaagaag tgaacctgtt gggcggttac cacctctgtc      360
gtgtgtgaca gttgntttga atctctaatt gctcagtaca gatccacatg caggttaagt      420
aagaagcttt tgaagaaaat ggaaagtctt aagtgatggc ttccaagaaa tcaaacctac      480
attaattagg gaacaacgga ctttacgtat cacaaatgaa gagactgacn aagtaaatca      540
acttggcctt ttctta                                                     556
```

<210> SEQ ID NO 157
<211> LENGTH: 333
<212> TYPE: DNA
<213> ORGANISM: Homo sapien
<220> FEATURE:
<221> NAME/KEY: misc_feature
<222> LOCATION: (1)...(333)
<223> OTHER INFORMATION: n = A,T,C or G

<400> SEQUENCE: 157

| | |
|---|---|
| ggtccacaaa aatatatnaa ataagctgga tatataaaan caaacactta acatngncan | 60 |
| cattccttca gttattcaaa ctcactgata nctaacnggg agnagttggn attctggaag | 120 |
| acttcctaag ctaaaagtat atttacatat ttacaacaca ngtaaatata acngaagaac | 180 |
| tacttcaaat aangnngaaa ttccagaatt ctanagattt atagctatag ntnacaanta | 240 |
| tcaccaattg gtttgcaatc aanngnccag cactacttat gannaangtt taactannaa | 300 |
| accaaaaggg gagaaaacct ggnagggaaa nat | 333 |

<210> SEQ ID NO 158
<211> LENGTH: 629
<212> TYPE: DNA
<213> ORGANISM: Homo sapien
<220> FEATURE:
<221> NAME/KEY: misc_feature
<222> LOCATION: (1)...(629)
<223> OTHER INFORMATION: n = A,T,C or G

<400> SEQUENCE: 158

| | |
|---|---|
| tcgagcggcc gcccgggcag gtctggtaca tttgtgcgag gtccggcact ctgttctcat | 60 |
| ccagtaagtg gtcgagccct ttctgcagaa ttgctgttaa atgttctcct aatagctgtt | 120 |
| tctccacaca agcaatcagt ggtttctgtg tgctgtggtc caagtaagtg attactctgt | 180 |
| ctccctcttc ttctaagcgt ttacttacat ggttaagata ttctggaacc tctcttcct | 240 |
| gcattaacct ttggccttcg gcagcatata agcaattagt ctcttccaaa aatttcagtt | 300 |
| caaatgaatc tttatacacc tgcaggtcag acagcatgcc caggnaggct ccgcaacagg | 360 |
| ctccggtcca cggcctcgcc gctcctctcg cgctcgatca gcagtaggat tccatcaatg | 420 |
| gttttactct gaaccatttt atcactaata atatgggttc taaacagttc taatcccata | 480 |
| tcccagatgg agggcagcgt ggagttctgc agcacatagg tgcggtccaa gaacaggaag | 540 |
| atgcttctga tcatgaatca tttgnctggc aatggtcctg ccagcacgtg gtaatctttc | 600 |
| ttttaaaaat aaacccttat ctaaacgtc | 629 |

<210> SEQ ID NO 159
<211> LENGTH: 629
<212> TYPE: DNA
<213> ORGANISM: Homo sapien
<220> FEATURE:
<221> NAME/KEY: misc_feature
<222> LOCATION: (1)...(629)
<223> OTHER INFORMATION: n = A,T,C or G

<400> SEQUENCE: 159

| | |
|---|---|
| tcgagcggcc gcccgggcag gttctagagg ganaatctgg ctgatttggg aataaaatat | 60 |
| aatcgaatat tcaacaccat gaagataaat cttattttgg aaatctactg accttaatac | 120 |
| cccaagcttg ccctgaatac tttgattgga attggaatat atcaaaaaag gttagtattt | 180 |
| ttgttgtagt taggatacta aaaggatatt agttacccaa gagatccaat ttgttttct | 240 |
| gatgaatagt gttcagtaaa atgaagcagt cttaagagtg actaataatt tcaaagtgat | 300 |
| ttttcgtcta ttcttaatat tttttaatta tttatttta agagttttat accttgagca | 360 |
| gatacaatga tccgctttag tgagaggaca atttctgatt gattgttttc tcttcaggcc | 420 |
| atctcacctc ttcattctct tgttacattt gaagcagttg atataatggg tttatacttt | 480 |
| aaaagataga catggtgcca tgaagtttgg ggaagttggg tgaattatcc cattctagtt | 540 |
| acagangagc tttccttaaa tgcccttac ttctangttt ggtcaagaag tcattttctg | 600 |

-continued

| agtaaaagtt attttcatat atgttgggg | 629 |

<210> SEQ ID NO 160
<211> LENGTH: 519
<212> TYPE: DNA
<213> ORGANISM: Homo sapien
<220> FEATURE:
<221> NAME/KEY: misc_feature
<222> LOCATION: (1)...(519)
<223> OTHER INFORMATION: n = A,T,C or G

<400> SEQUENCE: 160

| tcgagcggcg cgcccgggca ggtctgctgg gattaatgcc aagttnttca gccataaggt | 60 |
| agcgaaatct agcagaatcc agattacatc cacttccaat cacgcggtgt ttgggtaatc | 120 |
| cacttagttt ccagataaca tacgtaagaa tgtccactgg gttggaaacc acaattatga | 180 |
| tgcaatcagg actgtacttg acgatctgag gaataatgaa tttgaagaca ttaacatttc | 240 |
| tctgcaccag attgagccga ctctcccctt cttgctgacg gactcctgca gttaccacta | 300 |
| caatcttana attgggcggg tcacagaata atctttatct gccacaattt taggtgctga | 360 |
| agaaataagc tcccatgctg cagatccatc atttctnctt taagcttatc ttccaaaaca | 420 |
| tccacaagan caangttcat cagccagaga ctttcccaga atgctgatag nacacgccat | 480 |
| accaacttgt ccaacancca ctacagcgat cttattggt | 519 |

<210> SEQ ID NO 161
<211> LENGTH: 446
<212> TYPE: DNA
<213> ORGANISM: Homo sapien
<220> FEATURE:
<221> NAME/KEY: misc_feature
<222> LOCATION: (1)...(446)
<223> OTHER INFORMATION: n = A,T,C or G

<400> SEQUENCE: 161

| cgagnggccc gcccgggcag gtccagtaag cntttnacga tgatgggaaa ggttatgcaa | 60 |
| ggtcccagcg gtacaacgag ctgtttctac atcatttgta ttctgcatgg tacgtacaat | 120 |
| agcagacacc atctgaggag aacgcatgat agcgtgtctg gaagcttcct ttttagaaag | 180 |
| ctgatggacc ataactgcag ccttattaac caccacctgg tcctcgtcat ttagcagttt | 240 |
| tgtcagttca gggattgcac gtgtggcang ttctgcatca tcttgatagt taatcaagtt | 300 |
| tacaactggc atgtttcagc atctgcgatg ggctcagcaa acgctggaca ttantgggat | 360 |
| gagcagcatc aaactgtgta natgggatct gcatgccctc atctaatgtc tcagggaaca | 420 |
| tagcagctcg taccctctga gctcga | 446 |

<210> SEQ ID NO 162
<211> LENGTH: 354
<212> TYPE: DNA
<213> ORGANISM: Homo sapien
<220> FEATURE:
<221> NAME/KEY: misc_feature
<222> LOCATION: (1)...(354)
<223> OTHER INFORMATION: n = A,T,C or G

<400> SEQUENCE: 162

| agcgtngtcg cggcccgang tcctgggaag cctttnttgc tgagcctcac agcctctgtc | 60 |
| aggcggctgc ggatccagcg gtccaccagg ctctcatggc ctccgggctg ggaggnggtg | 120 |
| gagggcacaa aacccttccc aaggccacga anggcaaact tggtgcatt ccanagcttg | 180 |
| ttgcanaagt ggcggnaacc cagtatccgg ttcacatcca ggntgatgtc acgaccctgg | 240 |

```
gacatgtang cacataatcc aaaccggaga gcatcggtgc cacattcacg aatccccgct    300
gggaagtcag ctttctgccc ttctttggcc ttctccacct cgctgggatc cagg          354
g
```

<210> SEQ ID NO 163
<211> LENGTH: 258
<212> TYPE: DNA
<213> ORGANISM: Homo sapien
<220> FEATURE:
<221> NAME/KEY: misc_feature
<222> LOCATION: (1)...(258)
<223> OTHER INFORMATION: n = A,T,C or G

<400> SEQUENCE: 163

```
tttttcncca agtcctcttg ccgngggatc tngactgcaa tttaagacac ttctaattag     60
ttatacccag gccctgcaaa attgctgggt ttatataata tattcttgct gcacgaagat    120
ttattattct gttggatgat tctattttaa ttntatttat tctggccaaa aaagaacctt    180
ctccgctcgt caagagangc caatntgtct tgaaggacaa gagaaagatg ctaacacaca    240
ctttcttctt cttgagga                                                  258
```

<210> SEQ ID NO 164
<211> LENGTH: 282
<212> TYPE: DNA
<213> ORGANISM: Homo sapien
<220> FEATURE:
<221> NAME/KEY: misc_feature
<222> LOCATION: (1)...(282)
<223> OTHER INFORMATION: n = A,T,C or G

<400> SEQUENCE: 164

```
ggaacatatt acttttaaat tacttgggtc aatgaaacat ttaataaaaa catttgcttc     60
tctatataat acgtatgtat aaaataagcc ttttcanaaa ctctggttct cataatcctc    120
tataaatcan atgatctgac ttctaagagg aacaaattac agnaagaggt atacattnat    180
gaatactggt agtactagag ganngacgct aaaccactct actaccactt gcggaactct    240
cacagggtaa atgacaaagc caatgactga ctctaaaaac aa                       282
```

<210> SEQ ID NO 165
<211> LENGTH: 462
<212> TYPE: DNA
<213> ORGANISM: Homo sapien
<220> FEATURE:
<221> NAME/KEY: misc_feature
<222> LOCATION: (1)...(462)
<223> OTHER INFORMATION: n = A,T,C or G

<400> SEQUENCE: 165

```
gcccgggcan gtcctgtaat cccagctact cangangctg agtcatgana atcgcctgaa     60
tccgggaggt agaggccgca gcgagcaaag attaagccac tgcactccag tctgggtgac    120
agagtgagaa tctgtctgtt gctcctctgg cattggtctg aaatgggttt gtagaacatg    180
ccacagaagg accagcanca gcaacaaatg gatttgtgga angcgtagct ccaaatggag    240
cangcacact tgatgaagca cgctgtgtct gtgcagangc aaccactggc actgttccaa    300
aaacattgct gctagcatta cttgtggaag tatacgcatt actggaggtg gctgcanaac    360
tgaaaacgct gtctagttct gccanagctg catacttgnc tgaanatgca cttgactgac    420
tgggaactga accacanaac caacaggacc tttacctgtg ga                       462
```

<210> SEQ ID NO 166

```
<211> LENGTH: 365
<212> TYPE: DNA
<213> ORGANISM: Homo sapien
<220> FEATURE:
<221> NAME/KEY: misc_feature
<222> LOCATION: (1)...(365)
<223> OTHER INFORMATION: n = A,T,C or G

<400> SEQUENCE: 166
cgtgggtcgc ggcncgangt ctgaaaccaa tccagaacta acatcagca cacaaaaaat      60 accaggatag atggaatcaa aagactctga agccaaaagg aggctaggga gagcaactga    120
acttagcaag ctgaggactt cagtgtccat catccgatcc tgccctgtaa caacaggtct    180
atatgataga gatattccat ctgagctgga ggccattatc cttagcaaac taacacagaa    240
cagaaaacca aatacatgtt ctcatttaga agtaggagct aaatgatgag aactcaagga    300
cacaaagaaa ggaacaacag acactggggc ctacttgagg gtggagggtg ggaggaggga    360
gaaga                                                                365

<210> SEQ ID NO 167
<211> LENGTH: 364
<212> TYPE: DNA
<213> ORGANISM: Homo sapien
<220> FEATURE:
<221> NAME/KEY: misc_feature
<222> LOCATION: (1)...(364)
<223> OTHER INFORMATION: n = A,T,C or G

<400> SEQUENCE: 167
agcgtggtcg cggcgcgang tccagcccta gcttgcctgt gactccgcct tcactgggtg     60
ctctctctaa aagttgctga ctctttactg tatctcccaa ttcccactcc attggttcca    120
taaggggagg ggtgtctcac tcaacatggt gttcctggta ccaagaactg gctgacgaag    180
ctgggtgccg tggctcatgc ctgtaatccc agcactttg ggaggccaag aagggcggat    240
cacctgaggt ctggagttca agatcagcct gaccaacatg atgaaaccaa gtctccacta    300
aaaatataaa acaattagcc aggcatggtg gtgggtgcct gnaatcccag ctactgggga    360 ngct                                                                  364

<210> SEQ ID NO 168
<211> LENGTH: 447
<212> TYPE: DNA
<213> ORGANISM: Homo sapien
<220> FEATURE:
<221> NAME/KEY: misc_feature
<222> LOCATION: (1)...(447)
<223> OTHER INFORMATION: n = A,T,C or G

<400> SEQUENCE: 168
cccgggcagg tcaaaaccca aaacctttca ttttagccca aaccagctca tgattaggta     60
tacaaggata acagaaccag ttgtcaggac gagcatttga caagtaaaag caattcttgc    120
aaagctgcag ttcatccagc tcatggcatg tgtctttata tagcatcctc gcaatgtcag    180
cttgctcact gtctgctcca tagaaaatca cggtattgtg gagaagcaat tgggcatcag    240
ctttgaactc ttcataactt cggtatttcc cttcattcac tttctcttga atggtgggaa    300
cgtccacaga cctcggccgc gaccacgcta agcccgaatt ctgcagatat ccatcacact    360
ggcggccgtt cgagcatggc atctagaagg cccaattcgc ctatagngag tcgnattacc    420
aattcactgg ccgtcgnttt acaacgc                                        447
```

<210> SEQ ID NO 169
<211> LENGTH: 524
<212> TYPE: DNA
<213> ORGANISM: Homo sapien
<220> FEATURE:
<221> NAME/KEY: misc_feature
<222> LOCATION: (1)...(524)
<223> OTHER INFORMATION: n = A,T,C or G

<400> SEQUENCE: 169

| | | | | | |
|---|---|---|---|---|---|
| cgantngcgc | gcccgggcag | gtctgagcag | cctttctgnn | tgctggacta | ttgggattgg | 60 |
| gttcatccaa | cagagactgt | atggatgtta | aatggaaga | cacatcatag | gttggactcc | 120 |
| aacggttctg | aagtatgtcc | agacatatac | taccatctgc | atagactaag | aacaaagaag | 180 |
| taggtacatt | aaacgtaaca | agaccactaa | ggttttaaca | ttatagacaa | aacanaaata | 240 |
| gtcaaganta | ctttgctttt | gaagtttaaa | gattcctatg | ttgcttccca | gttaactgcc | 300 |
| taaaagata | agncataacc | accactagtg | aaataatcan | gatgatcaga | gaatgtcana | 360 |
| tgtgatcagt | ataaaactgg | angatattna | gtgtcatcct | ttggaaaagg | ctgccctatn | 420 |
| atccaggaaa | tcanaaacat | tnttgaacag | ggncccctagc | tatccacaga | catgtgggaa | 480 |
| attcattccc | caaatngtag | gctggatccc | ctatctgaaa | taac | | 524 |

<210> SEQ ID NO 170
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 170

| | | | | | |
|---|---|---|---|---|---|
| tcgancggcn | cgcccgggca | ggtgacaaac | ctgttattga | agatgttggt | tctgatgagg | 60 |
| aanaanatca | gaagggatgg | tgacaagaan | aanaanaaga | agattaagga | aaagtacatc | 120 |
| gatcaagaag | agctcaacaa | aacaaagccc | atctggacca | gaaatcccga | cgatattact | 180 |
| aatgangagt | acggagaatt | ctataanagc | ttgaccaatg | actgggaaga | tcacttggca | 240 |
| gtgaagcatt | tttcagttga | nggacagttg | gaattcagag | cccttctatn | tgtcccacga | 300 |
| cgtgctcctt | ttgatctgtt | tganancaga | aa | | | 332 |

<210> SEQ ID NO 171
<211> LENGTH: 334
<212> TYPE: DNA
<213> ORGANISM: Homo sapien
<220> FEATURE:
<221> NAME/KEY: misc_feature
<222> LOCATION: (1)...(334)
<223> OTHER INFORMATION: n = A,T,C or G

<400> SEQUENCE: 171

| | | | | | |
|---|---|---|---|---|---|
| cgagnggcnc | gcccgggcag | gtctgttgat | agcgacttaa | cagaaaagtc | tagacaaaca | 60 |
| taagcataaa | aaattacagt | ctttctaccc | ttgggaatgg | ggagaaaaag | gaatctctac | 120 |
| cccaagacca | gaaataataa | gtcctgtttc | tggtcctgaa | catccagaat | tatggaggct | 180 |
| ttggcctgac | accacattan | aatttggtct | ggaaatcaaa | ctttaganac | angagatcgt | 240 |
| aagccatttt | atactatcga | cctaaattcc | agtctaacgg | ttcctttaca | aagttgcgga | 300 |
| aagccctctt | atatgctagc | tgtaggaaat | atag | | | 334 |

<210> SEQ ID NO 172

```
<211> LENGTH: 439
<212> TYPE: DNA
<213> ORGANISM: Homo sapien
<220> FEATURE:
<221> NAME/KEY: misc_feature
<222> LOCATION: (1)...(439)
<223> OTHER INFORMATION: n = A,T,C or G

<400> SEQUENCE: 172
agcgtggtcg cggcccgang tctgcctata aaactagact tctgacgctg ggctccagct     60
tcattctcac aggtcatcat cctcatccgg gagagcagtt gtctgagcaa cctctaagtc    120
gtgctcatac tgtgctgcca aagctgggtc catgacaact tctggtgggg cgagagcagg    180
catggcaaca aattccaagt tagggtctcc aatgagcttc ctagcaagcc agaggaaggg    240
cttttcaaag ttgtagttac ttttggcaga aatgtcgtag tactgaagat tcttctttcg    300
gtggaagaca atggatttcg ccttcacttt ctgccttaat atccactttg gtgccacaca    360
acacaatggg gatgntttca cacacttngn accanatctc tatgccagnt aggccatttt    420
ggaagnactt cganggtac                                                 439

<210> SEQ ID NO 173
<211> LENGTH: 599
<212> TYPE: DNA
<213> ORGANISM: Homo sapien
<220> FEATURE:
<221> NAME/KEY: misc_feature
<222> LOCATION: (1)...(599)
<223> OTHER INFORMATION: n = A,T,C or G

<400> SEQUENCE: 173
cgatnggccg cccgggcagg tcctgtaaaa naggaaattc agacatcgta cgactcgtaa     60
ttgaatgtgg agctgactgc aatattttgt caaagcacca gaatagtgcc ctgcactttg    120
cgaagcagtc taacaatgtg cttgtgtacg acttgctgaa gaaccattta gagacacttt    180
caagagtagc agaagagaca ataaaggatt actttgaagc tcgccttgct ctgctagaac    240 cagttttttcc aatcgcatgt catcgactct gtgagggtcc agattttttca acagatttca    300 attaccaacc cccacagaac ataccagaag gctctggcat cctgctgttt atcttccatg    360 caaactttt gggtaaagaa gttattgctc ggctctgtgg accgtgtagt gtacaagctg     420
tagttctgaa tgataaattt cagcttcctg ttttttctggg tctcgctctg ttgtccaggc    480
tggagtgcag tggcgcggat tacagctcac tggagtcttg acttcccagg cacaagcaat    540
cctcccacct cagcctccta actacctggg actaaaaatg caccgccacc acattccgg     599

<210> SEQ ID NO 174
<211> LENGTH: 458
<212> TYPE: DNA
<213> ORGANISM: Homo sapien
<220> FEATURE:
<221> NAME/KEY: misc_feature
<222> LOCATION: (1)...(458)
<223> OTHER INFORMATION: n = A,T,C or G

<400> SEQUENCE: 174
tcgatttggc cgcccgggca ggtccatgcn gnttntgccc attcccatgg ngcccgacaa     60
ncccatcccc gaggccgaca tccccatgtt catgttcatg cccaccatgc cctggctcat    120
ccctgcgctg ttccccagag gggccattcc catggtgccc gtcattacac cgggcatgtt    180
cataggcatg ggtcccccca ggagagggtt agnttgaggc cggacaggaa gcatgtttga    240
tggagaactg aggttcacag nctccaaaac tttgagtcat cacattcata ggctgctgca    300
```

-continued

```
tattctgtct gctgaatcca ttgtatncag tgatggcctg ctggggnttt ggaaggctng      360
cataccaggt agtaagntcg tctaggctga tgtttacacc tggggtcaga ccaagtanga      420
gggcaaggtt ttgctgactg attttctgga cccatatc                              458
```

<210> SEQ ID NO 175
<211> LENGTH: 1206
<212> TYPE: DNA
<213> ORGANISM: Homo sapien

<400> SEQUENCE: 175

```
ggcacgagga agttttgtgt actgaaaaag aaactgtcag aagcaaaaga aataaaatca      60
cagttagaga accaaaaagt taaatgggaa caagagctct gcagtgtgag gtttctcaca     120
ctcatgaaaa tgaaaattat ctcttacatg aaaattgcat gttgaaaaag gaaattgcca     180
tgctaaaact ggaaatagcc acactgaaac accaatacca ggaaaaggaa ataaaatact     240
ttgaggacat taagatttta aagaaaaga atgctgaact tcagatgacc ctaaaactga     300
aagaggaatc attaactaaa agggcatctc aatatagtgg gcagcttaaa gttctgatag     360
ctgagaacac aatgctcact tctaaattga aggaaaaaca agacaaagaa atactagagg     420
cagaaattga atcacaccat cctagactgg cttctgctgt acaagaccat gatcaaattg     480
tgacatcaag aaaaagtcaa gaacctgctt tccacattgc aggagatgct tgtttgcaaa     540
gaaaaatgaa tgttgatgtg agtagtacga tatataacaa tgaggtgctc catcaaccac     600
tttctgaagc tcaaaggaaa tccaaaagcc taaaaattaa tctcaattat gccggagatg     660
ctctaagaga aaatacattg gtttcagaac atgcacaaag agaccaacgt gaaacacagt     720
gtcaaatgaa ggaagctgaa cacatgtatc aaaacgaaca agataatgtg aacaaacaca     780
ctgaacagca ggagtctcta gatcagaaat tatttcaact acaaagcaaa aatatgtggc     840
ttcaacagca attagttcat gcacataaga agctgacaa caaaagcaag ataacaattg     900
atattcattt tcttgagagg aaaatgcaac atcatctcct aaaagagaaa atgaggaga     960 tatttaatta caataaccat ttaaaaaacc gtatatatca atatgaaaaa gagaaagcag    1020
aaacagaagt tatataatag tataacactg ccaaggagcg gattatctca tcttcatcct    1080
gtaattccag tgtttgtcac gtggttgttg aataaatgaa taaagaatga gaaaccaga    1140 agctctgata cataatcata atgataatta tttcaatgca caactacggg tggtgctgct    1200
cgtgcc                                                              1206
```

<210> SEQ ID NO 176
<211> LENGTH: 317
<212> TYPE: PRT
<213> ORGANISM: Homo sapien

<400> SEQUENCE: 176

```
Met Gly Thr Arg Ala Leu Gln Cys Glu Val Ser His Thr His Glu Asn
  1               5                  10                  15

Glu Asn Tyr Leu Leu His Glu Asn Cys Met Leu Lys Lys Glu Ile Ala
             20                  25                  30

Met Leu Lys Leu Glu Ile Ala Thr Leu Lys His Gln Tyr Gln Glu Lys
         35                  40                  45

Glu Asn Lys Tyr Phe Glu Asp Ile Lys Ile Leu Lys Glu Lys Asn Ala
     50                  55                  60

Glu Leu Gln Met Thr Leu Lys Leu Lys Glu Glu Ser Leu Thr Lys Arg
 65                  70                  75                  80
```

Ala Ser Gln Tyr Ser Gly Gln Leu Lys Val Leu Ile Ala Glu Asn Thr
                 85                  90                  95
Met Leu Thr Ser Lys Leu Lys Glu Lys Gln Asp Lys Glu Ile Leu Glu
            100                 105                 110
Ala Glu Ile Glu Ser His His Pro Arg Leu Ala Ser Ala Val Gln Asp
        115                 120                 125
His Asp Gln Ile Val Thr Ser Arg Lys Ser Gln Glu Pro Ala Phe His
    130                 135                 140
Ile Ala Gly Asp Ala Cys Leu Gln Arg Lys Met Asn Val Asp Val Ser
145                 150                 155                 160
Ser Thr Ile Tyr Asn Asn Glu Val Leu His Gln Pro Leu Ser Glu Ala
                165                 170                 175
Gln Arg Lys Ser Lys Ser Leu Lys Ile Asn Leu Asn Tyr Ala Gly Asp
            180                 185                 190
Ala Leu Arg Glu Asn Thr Leu Val Ser Glu His Ala Gln Arg Asp Gln
        195                 200                 205
Arg Glu Thr Gln Cys Gln Met Lys Glu Ala Glu His Met Tyr Gln Asn
    210                 215                 220
Glu Gln Asp Asn Val Asn Lys His Thr Glu Gln Glu Ser Leu Asp
225                 230                 235                 240
Gln Lys Leu Phe Gln Leu Ser Lys Asn Met Trp Leu Gln Gln Gln
                245                 250                 255
Leu Val His Ala His Lys Lys Ala Asp Asn Lys Ser Lys Ile Thr Ile
            260                 265                 270
Asp Ile His Phe Leu Glu Arg Lys Met Gln His His Leu Leu Lys Glu
        275                 280                 285
Lys Asn Glu Glu Ile Phe Asn Tyr Asn Asn His Leu Lys Asn Arg Ile
    290                 295                 300
Tyr Gln Tyr Glu Lys Glu Lys Ala Glu Thr Glu Val Ile
305                 310                 315

<210> SEQ ID NO 177
<211> LENGTH: 20
<212> TYPE: DNA
<213> ORGANISM: Artificial Sequence
<220> FEATURE:
<223> OTHER INFORMATION: Made in the Lab

<400> SEQUENCE: 177
ccaatcatct ccacaggagc                                                 20

<210> SEQ ID NO 178
<211> LENGTH: 1665
<212> TYPE: DNA
<213> ORGANISM: Homo sapien

<400> SEQUENCE: 178
gcaaactttc aagcagagcc tcccgagaag ccatctgcct tcgagcctgc cattgaaatg    60
caaaagtctg ttccaaataa agccttggaa ttgaagaatg aacaaacatt gagagcagat   120
cagatgttcc cttcagaatc aaaacaaaag aaggttgaag aaaattcttg ggattctgag   180
agtctccgtg agactgtttc acagaaggat gtgtgtgtac ccaaggctac acatcaaaaa   240
gaaatggata aaataagtgg aaaattagaa gattcaacta gcctatcaaa aatcttggat   300
acagttcatt cttgtgaaag agcaagggaa cttcaaaaag atcactgtga acaacgtaca   360
ggaaaaatgg aacaaatgaa aaagaagttt tgtgtactga aaagaaact gtcagaagca   420

```
aaagaaataa aatcacagtt agagaaccaa aaagttaaat gggaacaaga gctctgcagt    480
gtgaggtttc tcacactcat gaaaatgaaa attatctctt acatgaaaat tgcatgttga    540
aaaaggaaat tgccatgcta aaactggaaa tagccacact gaaacaccaa taccaggaaa    600
aggaaaataa atactttgag gacattaaga ttttaaaaga aaagaatgct gaacttcaga    660
tgaccctaaa actgaaagag gaatcattaa ctaaaagggc atctcaatat agtgggcagc    720
ttaaagttct gatagctgag aacacaatgc tcacttctaa attgaaggaa aaacaagaca    780
aagaaatact agaggcagaa attgaatcac accatcctag actggcttct gctgtacaag    840
accatgatca aattgtgaca tcaagaaaaa gtcaagaacc tgctttccac attgcaggag    900
atgcttgttt gcaaagaaaa atgaatgttg atgtgagtag tacgatatat aacaatgagg    960
tgctccatca accactttct gaagctcaaa ggaaatccaa aagcctaaaa attaatctca   1020
attatgccgg agatgctcta agagaaaata cattggtttc agaacatgca caagagacc    1080
aacgtgaaac acagtgtcaa atgaaggaag ctgaacacat gtatcaaaac gaacaagata   1140
atgtgaacaa acacactgaa cagcaggagt ctctagatca gaaattattt caactacaaa   1200
gcaaaaatat gtggcttcaa cagcaattag ttcatgcaca taagaaagct gacaacaaaa   1260
gcaagataac aattgatatt cattttcttg agaggaaaat gcaacatcat ctcctaaaag   1320
agaaaaatga ggagatattt aattacaata accatttaaa aaaccgtata tatcaatatg   1380
aaaaagagaa agcagaaaca gaaaactcat gagagacaag cagtaagaaa cttcttttgg   1440
agaaacaaca gaccagatct ttactcacaa ctcatgctag gaggccagtc ctagcattac   1500
cttatgttga aaatcttacc aatagtctgt gtcaacagaa tacttatttt agaagaaaaa   1560
ttcatgattt cttcctgaag cctgggcgac agagcgagac tctgtctcaa aaaaaaaaa   1620
aaaaaagaa agaaagaaat gcctgtgctt acttcgcttc ccagg                    1665
```

<210> SEQ ID NO 179
<211> LENGTH: 179
<212> TYPE: PRT
<213> ORGANISM: Homo sapien

<400> SEQUENCE: 179

```
Ala Asn Phe Gln Ala Glu Pro Pro Glu Lys Pro Ser Ala Phe Glu Pro
 1               5                  10                  15

Ala Ile Glu Met Gln Lys Ser Val Pro Asn Lys Ala Leu Glu Leu Lys
            20                  25                  30

Asn Glu Gln Thr Leu Arg Ala Asp Gln Met Phe Pro Ser Glu Ser Lys
        35                  40                  45

Gln Lys Lys Val Glu Glu Asn Ser Trp Asp Ser Glu Ser Leu Arg Glu
    50                  55                  60

Thr Val Ser Gln Lys Asp Val Cys Val Pro Lys Ala Thr His Gln Lys
65                  70                  75                  80

Glu Met Asp Lys Ile Ser Gly Lys Leu Glu Asp Ser Thr Ser Leu Ser
                85                  90                  95

Lys Ile Leu Asp Thr Val His Ser Cys Glu Arg Ala Arg Glu Leu Gln
            100                 105                 110

Lys Asp His Cys Glu Gln Arg Thr Gly Lys Met Glu Gln Met Lys Lys
        115                 120                 125

Lys Phe Cys Val Leu Lys Lys Leu Ser Glu Ala Lys Glu Ile Lys
    130                 135                 140

Ser Gln Leu Glu Asn Gln Lys Val Lys Trp Glu Gln Glu Leu Cys Ser
```

| 145 | | | 150 | | | | 155 | | | | 160 |
|---|---|---|---|---|---|---|---|---|---|---|---|
| Val | Arg | Phe | Leu | Thr | Leu | Met | Lys | Met | Lys | Ile | Ile | Ser | Tyr | Met | Lys |
| | | | | 165 | | | | 170 | | | | 175 | | | |

Ile Ala Cys

<210> SEQ ID NO 180
<211> LENGTH: 1681
<212> TYPE: DNA
<213> ORGANISM: Homo sapien

<400> SEQUENCE: 180

```
gatacagtca ttcttgtgaa agagcaaggg aacttcaaaa agatcactgt gaacaacgta      60
caggaaaaat ggaacaaatg aaaaagaagt tttgtgtact gaaaaagaaa ctgtcagaag     120
caaaagaaat aaaatcacag ttagagaacc aaaaagttaa atgggaacaa gagctctgca     180
gtgtgagatt gactttaaac caagaagaag agaagagaag aaatgccgat atattaaatg     240
aaaaaattag ggaagaatta ggaagaatcg aagagcagca taggaaagag ttagaagtga     300
aacaacaact tgaacaggct ctcagaatac aagatataga attgaagagt gtagaaagta     360
atttgaatca ggtttctcac actcatgaaa atgaaaatta tctcttacat gaaaattgca     420
tgttgaaaaa ggaaattgcc atgctaaaac tggaaatagc cacactgaaa caccaatacc     480
aggaaaagga aataaaatac tttgaggaca ttaagatttt aaaagaaaag aatgctgaac     540
ttcagatgac cctaaaactg aaagaggaat cattaactaa aagggcatct caatatagtg     600
ggcagcttaa agttctgata gctgagaaca caatgctcac ttctaaattg aaggaaaaac     660
aagacaaaga aatactagag gcagaaattg aatcacacca tcctagactg gcttctgctg     720
tacaagacca tgatcaaatt gtgacatcaa gaaaagtcag agaacctgct ttccacattg     780
caggagatgc ttgtttgcaa agaaaaatga atgttgatgt gagtagtacg atatataaca     840
atgaggtgct ccatcaacca ctttctgaag ctcaaggaaa atccaaaagc ctaaaaatta     900
atctcaatta tgccggagat gctctaagag aaaatacatt ggtttcagaa catgcacaaa     960
gagaccaacg tgaaacacag tgtcaaatga aggaagctga acacatgtat caaaacgaac    1020
aagataatgt gaacaaacac actgaacagc aggagtctct agatcagaaa ttatttcaac    1080
tacaaagcaa aaatatgtgg cttcaacagc aattagttca tgcacataag aaagctgaca    1140
acaaaagcaa gataacaatt gatattcatt tccttgagag gaaatgcaa catcatctcc     1200
taaagagaa aaatgaggag atatttaatt acaataacca tttaaaaaac cgtatatatc     1260
aatatgaaaa agagaaagca gaaacagaaa actcatgaga gacaagcagt aagaaacttc     1320
ttttggagaa acaacagacc agatctttac tcacaactca tgctaggagg ccagtcctag     1380
cattacctta tgttgaaaaa tcttaccaat agtctgtgtc aacagaatac ttattttaga     1440
agaaaaattc atgatttctt cctgaagcct acagacataa aataacagtg tgaagaatta     1500
cttgttcacg aattgcataa aagctgccca ggatttccat ctaccctgga tgatgccgga     1560
gacatcattc aatccaacca gaatctcgct ctgtcactca ggctggagtg cagtgggcgc     1620
aatctcggct cactgcaact ctgcctccca ggttcacgcc attctctggc acagcctccc     1680
g                                                                    1681
```

<210> SEQ ID NO 181
<211> LENGTH: 432
<212> TYPE: PRT
<213> ORGANISM: Homo sapien -continued

```
<400> SEQUENCE: 181

Asp Thr Val His Ser Cys Glu Arg Ala Arg Glu Leu Gln Lys Asp His
1               5                   10                  15

Cys Glu Gln Arg Thr Gly Lys Met Glu Gln Met Lys Lys Lys Phe Cys
            20                  25                  30

Val Leu Lys Lys Lys Leu Ser Glu Ala Lys Glu Ile Lys Ser Gln Leu
        35                  40                  45

Glu Asn Gln Lys Val Lys Trp Glu Gln Glu Leu Cys Ser Val Arg Leu
    50                  55                  60

Thr Leu Asn Gln Glu Glu Lys Arg Arg Asn Ala Asp Ile Leu Asn
65                  70                  75                  80

Glu Lys Ile Arg Glu Glu Leu Gly Arg Ile Glu Glu Gln His Arg Lys
                85                  90                  95

Glu Leu Glu Val Lys Gln Gln Leu Glu Gln Ala Leu Arg Ile Gln Asp
            100                 105                 110

Ile Glu Leu Lys Ser Val Glu Ser Asn Leu Asn Gln Val Ser His Thr
        115                 120                 125

His Glu Asn Glu Asn Tyr Leu Leu His Glu Asn Cys Met Leu Lys Lys
    130                 135                 140

Glu Ile Ala Met Leu Lys Leu Glu Ile Ala Thr Leu Lys His Gln Tyr
145                 150                 155                 160

Gln Glu Lys Glu Asn Lys Tyr Phe Glu Asp Ile Lys Ile Leu Lys Glu
                165                 170                 175

Lys Asn Ala Glu Leu Gln Met Thr Leu Lys Leu Lys Glu Glu Ser Leu
            180                 185                 190

Thr Lys Arg Ala Ser Gln Tyr Ser Gly Gln Leu Lys Val Leu Ile Ala
        195                 200                 205

Glu Asn Thr Met Leu Thr Ser Lys Leu Lys Glu Lys Gln Asp Lys Glu
    210                 215                 220

Ile Leu Glu Ala Glu Ile Glu Ser His His Pro Arg Leu Ala Ser Ala
225                 230                 235                 240

Val Gln Asp His Asp Gln Ile Val Thr Ser Arg Lys Ser Gln Glu Pro
                245                 250                 255

Ala Phe His Ile Ala Gly Asp Ala Cys Leu Gln Arg Lys Met Asn Val
            260                 265                 270

Asp Val Ser Ser Thr Ile Tyr Asn Asn Glu Val Leu His Gln Pro Leu
        275                 280                 285

Ser Glu Ala Gln Arg Lys Ser Lys Ser Leu Lys Ile Asn Leu Asn Tyr
    290                 295                 300

Ala Gly Asp Ala Leu Arg Glu Asn Thr Leu Val Ser Glu His Ala Gln
305                 310                 315                 320

Arg Asp Gln Arg Glu Thr Gln Cys Gln Met Lys Glu Ala Glu His Met
                325                 330                 335

Tyr Gln Asn Glu Gln Asp Asn Val Asn Lys His Thr Glu Gln Gln Glu
            340                 345                 350

Ser Leu Asp Gln Lys Leu Phe Gln Leu Gln Ser Lys Asn Met Trp Leu
        355                 360                 365

Gln Gln Gln Leu Val His Ala His Lys Lys Ala Asp Asn Lys Ser Lys
    370                 375                 380

Ile Thr Ile Asp Ile His Phe Leu Glu Arg Lys Met Gln His Leu
385                 390                 395                 400

Leu Lys Glu Lys Asn Glu Glu Ile Phe Asn Tyr Asn Asn His Leu Lys
                405                 410                 415
```

Asn Arg Ile Tyr Gln Tyr Glu Lys Glu Lys Ala Glu Thr Glu Asn Ser
        420                 425                 430

<210> SEQ ID NO 182
<211> LENGTH: 511
<212> TYPE: DNA
<213> ORGANISM: Homo sapiens

<400> SEQUENCE: 182
gaagtttcat gaggtttagc ttttctgggc tggggagtgg agagaaagaa gttgcagggc      60
ttacaggaaa tcccagagcc tgaggttttc tcccagattt gagaactcta gattctgcat     120
cattatcttt gagtctatat tctcttgggc tgtaagaaga tgaggaatgt aataggtctg     180
ccccaagcct ttcatgcctt ctgtaccaag cttgtttcct tgtgcatcct tcccaggctc     240
tggctgcccc ttattggaga atgtgatttc caagacaatc aatccacaag tgtctaagac     300
tgaatacaaa gaacttcttc aagagttcat agacgacaat gccactacaa atgccataga     360
tgaattgaag gaatgttttc ttaaccaaac ggatgaaact ctgagcaatg ttgaggtgtt     420
tatgcaatta atatatgaca gcagtctttg tgatttatttt taactttctg caagacctttt    480 ggctcacaga actgcaggt atggtgagaa a                                       511

<210> SEQ ID NO 183
<211> LENGTH: 260
<212> TYPE: DNA
<213> ORGANISM: Homo sapiens

<400> SEQUENCE: 183
cacctcgcgg ttcagctcct ctgtcttggt gaagaaccat tcctcggcat ccttgcggtt       60
cttctctgcc atcttctcat actggtcacg catctcgttc agaatgcggc tcaggtccac      120
gccaggtgca gcgtccatct ccacattgac atctccaccc acctgcctc tcagggcatt      180 catctcctcc tcgtggttct tcttcaggta ggccagctcc tccttcaggc tctcaatctg      240
catctccagg tcagctctgg                                                   260

<210> SEQ ID NO 184
<211> LENGTH: 461
<212> TYPE: DNA
<213> ORGANISM: Homo sapiens

<400> SEQUENCE: 184
gtctgatggg agaccaaaga atttgcaagt ggatggtttg gtatcactgt aaataaaaag       60
agggcctttt ctagctgtat gactgttact tgaccttctt tgaaaagcat tcccaaaatg      120 ctctattta gatagattaa cattaaccaa cataattttt tttagatcga gtcagcataa      180
atttctaagt cagcctctag tcgtggttca tctctttcac ctgcatttta tttggtgttt      240
gtctgaagaa aggaaagagg aaagcaaata cgaattgtac tatttgtacc aaatctttgg      300
gattcattgg caaataattt cagtgtggtg tattattaaa tagaaaaaaa aaattttgtt      360
tcctaggttg aaggtctaat tgataccgtt tgacttatga tgaccattta tgcactttca      420
aatgaatttg ctttcaaaat aaatgaagag cagacctcgg c                          461

<210> SEQ ID NO 185
<211> LENGTH: 531
<212> TYPE: DNA
<213> ORGANISM: Homo sapiens

<400> SEQUENCE: 185

```
tctgatttta tttccttctc aaaaaaagtt atttacagaa ggtatatatc aacaatctga      60
caggcagtga acttgacatg attagctggc atgatttttt cttttttttc ccccaaacat     120
tgtttttgtg gccttgaatt ttaagacaaa tattctacac gcatattgc acaggatgga     180 tggcaaaaaa aagtttaaaa acaaaaaccc ttaacggaac tgccttaaaa aggcagacgt     240
cctagtgcct gtcatgttat attaaacata catacacaca atcttttttgc ttattataat     300 acagacttaa atgtacaaag atgttttcca cttttttcaa tttttaaaca caacagctat     360
aaacctgaac acatatgcta tcatcatgcc ataagactaa aacaattata tttagcgaca     420
agtagaaagg attaaatagt caaatacaag aatgaaaaac gcagtacata gtgtcgcgaa     480
ctcaaatcgg catttagata gatccagtgg tttaaacggc acgttttgc t              531

<210> SEQ ID NO 186
<211> LENGTH: 441
<212> TYPE: DNA
<213> ORGANISM: Homo sapiens

<400> SEQUENCE: 186
cattcctttc ctcgcgttgg ggtttctctg tgtcagcgag cctcggtaca ctgatttccg      60
atcaaaagaa tcatcatctt taccttgact tttcagggaa ttactgaact ttcttctcag     120
aagatagggc acagccattg ccttggcctc acttgaaggg tctgcatttg ggtcctctgg     180
tctcttgcca agtttcccaa ccactcgagg gagaaatatc gggaggtttg acttcctccg     240
gggctttccc gagggcttca ccgtgagccc tgcggccctc agggctgcaa tcctggattc     300
aatgtctgaa acctcgctct ctgcctgctg gacttctgag gccgtcactg ccactctgtc     360
ctccagctct gacagctcct catctgtggt cctgttgtac tggacggggt ccccagggtc     420
ctgggggctt ttttcctgtc t                                               441

<210> SEQ ID NO 187
<211> LENGTH: 371
<212> TYPE: DNA
<213> ORGANISM: Homo sapiens

<400> SEQUENCE: 187
aaaagtgaat gagtaactat tatattgttg gcaataataa gttgcaaaat catcaggctg      60
caggctgctg atggtgagag tgaactctgt cccagatcca ctgccgctga accttgatgg     120
gaccccagat tctaaactag acgccttatg gatcaggagc tttggggctt tccctggttt     180
ctgttgatac caggccaacc aactactaac actctgactg gcccggcaag tgatggtgac     240
tctgtctcct acagttgcag acagggtgga aggagactgg gtcatctgga tgtcacattt     300
ggcacctggg agccagagca gcaggagccc caggagctga gcgggaccc tcatgtccat     360 gctgagtcct g                                                          371

<210> SEQ ID NO 188
<211> LENGTH: 226
<212> TYPE: DNA
<213> ORGANISM: Homo sapiens

<400> SEQUENCE: 188
ggtatataaa ttgagatgcc cccccaggcc agcaaatgtt cctttttgtt caaagtctat      60
ttttattcct tgatatttttt cttttttttt ttttgtggaa tggggacttg tgaattttc     120 taaaggtgct atttaacatg ggaggagagc gtgtgcggct ccagcccagc ccgctgctca     180
```

-continued

| ctttccaccc tctctccacc tgcctctggc ttctcaggac ctgccc | 226 |

<210> SEQ ID NO 189
<211> LENGTH: 391
<212> TYPE: DNA
<213> ORGANISM: Homo sapiens
<220> FEATURE:
<221> NAME/KEY: misc_feature
<222> LOCATION: (1)...(391)
<223> OTHER INFORMATION: n=A,T,C or G

<400> SEQUENCE: 189

| tgggtgaagt ttattctgtt ttcacatcta ggttgttggg ganagtgata gacaaagttc | 60 |
| tggattctgg gcatcgtcgg cgcatgcttg taatcctact tgggaggttg anacaggaga | 120 |
| cctcggccgc naccacgcta agggcgaatt ctgcanatat ccatcacact ggcggccgct | 180 |
| cgagcatgca tctanagggc ccaattcncc ctatagtgag ncgtattaca attcactggc | 240 |
| cgtcgtttta caacgtcgtg actgggaaaa ccctggcgtt acccaactta atcgccttgc | 300 |
| agcacatccc cctttcncca gctggcttaa tancgaagag gcccgcaccg atcgcccttc | 360 |
| ccaacanttg cgcagcctga atggcgaatg g | 391 |

<210> SEQ ID NO 190
<211> LENGTH: 501
<212> TYPE: DNA
<213> ORGANISM: Homo sapiens

<400> SEQUENCE: 190

| catcttggcc tttttgagct gtttccgctt cttctcatcc cggtcactgt caccctcatt | 60 |
| actggaggag ctggcagagg cgttgctgtc aaactcctct gccacatctt cctcctcttc | 120 |
| acctgggttg aatgactcat cggtttcttc tcctgagtca tcgctgctgt cattggcatt | 180 |
| ctcctcccgg atcttgcctt cctccttcat cctctccaag taggcatcat gctggtcctc | 240 |
| atcagagtca gcatattcat cgtagcttgg gttcatgccc tctttcaatc ctcggttttt | 300 |
| gatgttgagc ttttttcgcgt tgacaaaatc aaacagtttc ccgtactcct ccctctcaat | 360 |
| gctgctgaag gtatactgag tgccctgctt ggtctcaatt tcaaagtcaa aggaacgagt | 420 |
| agtagtggta ccacgagcaa agttgacaaa ggagatctca tcgaagcgga tgtgcacagg | 480 |
| tggcttgtgg acgtagatga a | 501 |

<210> SEQ ID NO 191
<211> LENGTH: 241
<212> TYPE: DNA
<213> ORGANISM: Homo sapiens
<220> FEATURE:
<221> NAME/KEY: misc_feature
<222> LOCATION: (49)
<223> OTHER INFORMATION: n=A,T,C or G

<400> SEQUENCE: 191

| ggaaaaactg tgaaaatat atctgaattt attaagtaca gtataaaana gggttgtggc | 60 |
| aacagaaagt aaaaactaac atggattgct ataaatatgc tgaagcctag ttgttcaaat | 120 |
| gatacaattc tctcatgcta ctctaaagtt tataaagaaa aaggatttac actttacaca | 180 |
| ctgtacacaa aaggaatacc ttctgagagc cagggagtgg ggaaagggga aggagacttg | 240 |
| a | 241 |

<210> SEQ ID NO 192
<211> LENGTH: 271

```
<212> TYPE: DNA
<213> ORGANISM: Homo sapiens
<220> FEATURE:
<221> NAME/KEY: misc_feature
<222> LOCATION: (1)...(271)
<223> OTHER INFORMATION: n=A,T,C or G

<400> SEQUENCE: 192
tggtcntgga ttcacanata aantanatcg actaaaactg gcagaaattg tgaagcaggt    60
gatagaagan caaaccacgt cccacgaatc ccaataatga cagcttcaga ctttgctttt   120
ttaacaattt gaaaaattat tctttaatgt ataaagtaat tttatgtaaa ttaataaatc   180
ataatttcat ttccacattg attaaagctg ctgtatagat ttagggngca ggacttaata   240
atagnggaaa tgaaattatg atttattaat c                                   271

<210> SEQ ID NO 193
<211> LENGTH: 351
<212> TYPE: DNA
<213> ORGANISM: Homo sapiens

<400> SEQUENCE: 193
agtcgaggcg ctgatcccta aaatggcgaa catgtgtttt catcatttca gccaaagtcc    60
taacttcctg tgcctttcct atcacctcga gaagtaatta tcagttggtt tggattttg   120 gaccaccgtt cagtcatttt gggttgccgt gctcccaaaa cattttaaat gaaagtattg   180
gcattcaaaa agacagcaga caaatgaaa gaaaatgaga gcagaaagta agcatttcca   240
gcctatctaa tttctttagt tttctatttg cctccagtgc agtccatttc ctaatgtata   300
ccagcctact gtactattta aaatgctcaa tttcagcacc gatggacctg c             351

<210> SEQ ID NO 194
<211> LENGTH: 311
<212> TYPE: DNA
<213> ORGANISM: Homo sapiens

<400> SEQUENCE: 194
ctgagacaca gaggcccact gcgaggggga cagtggcggt gggactgacc tgctgacagt    60
caccctccct ctgctgggat gaggtccagg agccaactaa aacaatggca gaggagacat   120
ctctggtgtt cccaccaccc tagatgaaaa tccacagcac agacctctac cgtgtttctc   180
ttccatccct aaaccacttc cttaaaatgt ttggatttgc aaagccaatt tggggcctgt   240
ggagcctggg gttggatagg gccatggctg gtcccccacc atacctcccc tccacatcac   300
tgacacagac c                                                         311

<210> SEQ ID NO 195
<211> LENGTH: 381
<212> TYPE: DNA
<213> ORGANISM: Homo sapiens

<400> SEQUENCE: 195
tgtcagagtg gcactggtag aagttccagg aaccctgaac tgtaagggtt cttcatcagt    60
gccaacagga tgacatgaaa tgatgtactc agaagtgtcc tggaatgggg cccatgagat   120
ggttgtctga gagagagctt cttgtcctgt cttttccctt ccaatcaggg gctcgctctt   180
ctgattattc ttcagggcaa tgacataaat tgtatattcg gttcccggtt ccaggccagt   240
aatagtagcc tctgtgacac cagggcgggg ccgagggacc acttctctgg gaggagaccc   300
aggcttctca tacttgatga tgtagccggt aatcctggca cgtggcggct gccatgatac   360
```

```
cagcagggaa ttgggtgtgg t                                              381
```

```
<210> SEQ ID NO 196
<211> LENGTH: 401
<212> TYPE: DNA
<213> ORGANISM: Homo sapiens

<400> SEQUENCE: 196
cacaaacaag aggagcacca gacctcctct tggcttcgag atggcttcgc cacaccaaga     60
gcccaaacct ggagacctga ttgagatttt ccgccttggc tatgagcact gggccctgta   120
tataggagat ggctacgtga tccatctggc tcctccaagt gagtaccccg ggctggctc    180
ctccagtgtc ttctcagtcc tgagcaacag tgcagaggtg aaacgggagc gcctggaaga   240
tgtggtggga ggctgttgct atcgggtcaa caacagcttg gaccatgagt accaaccacg   300
gcccgtggag gtgatcacca gttctgcgaa ggagatggtt ggtcagaaga tgaagtacag   360
tattgtgagc aggaactgtg agcactttgt cacccagacc t                      401
```

```
<210> SEQ ID NO 197
<211> LENGTH: 471
<212> TYPE: DNA
<213> ORGANISM: Homo sapiens

<400> SEQUENCE: 197
ctgtaatgat gtgagcaggg agccttcctc cctgggccac ctgcagagag ctttcccacc     60
aactttgtac cttgattgcc ttacaaagtt atttgtttac aaacagcgac catataaaag   120
cctcctgccc caaagcttgt gggcacatgg gcacatacag actcacatac agacacacac   180
atatatgtac agacatgtac tctcacacac acaggcacca gcatacacac gttttttctag   240
gtacagctcc caggaacagc taggtgggaa agtcccatca ctgagggagc ctaaccatgt   300
ccctgaacaa aaattgggca ctcatctatt ccttttctct tgtgtcccta ctcattgaaa   360
ccaaactctg gaaaggaccc aatgtaccag tatttatacc tctagtgaag cacagagaga   420
ggaagagagc tgcttaaact cacacaacaa tgaactgcag acacagacct g            471
```

```
<210> SEQ ID NO 198
<211> LENGTH: 201
<212> TYPE: DNA
<213> ORGANISM: Homo sapiens

<400> SEQUENCE: 198
ggtccattga ggctctgtcg gccatgccca cagttcgaag ctttgccaac gaggagggcg     60
aagcccagaa gtttagggaa aagctgcaag aaataaagac actcaaccag aaggaggctg   120
tggcctatgc agtcaactcc tggaccacta gtatttcagg tatgctgctg aaagtgggaa   180
tcctctacat tggtgggcag a                                             201
```

```
<210> SEQ ID NO 199
<211> LENGTH: 551
<212> TYPE: DNA
<213> ORGANISM: Homo sapiens

<400> SEQUENCE: 199
tctggcacag atcttcaccc acacggcggt ccacgtgctg atcatcttcc gggtctcacc     60
gggcctggaa cacaccatct tcccatgagc ccggtgccc agtctggtga cttccatctt    120
ggcccctggc cttatgtccc agttatgacc cctgacttca actctggctc ttaccctgta   180
actccagtcc atctctgaca ttttttaacac ccggccttgt gaccgtggac atagctcctg   240
```

```
acctcgattc ccatcttgag cccagtgtta gtccatgaga tcatgacctg actcctggtc    300
tccaaccttg tgatcctaat tctgggacct caatcctagc ctctgaactt gggaccctgg    360
agctcctgac cttagtcctg accgctaccc ttgattctga cctttgatcc tgtaacttag    420
gggtggcccc tgaccttatt actgtcattt agctccttga ccttgccact tcaatcctgg    480
ctttatgacc tcctactctc aattttaact ttaaccaaat gaccaaattt gtgacactaa    540
atgaccacaa t                                                         551
```

```
<210> SEQ ID NO 200
<211> LENGTH: 211
<212> TYPE: DNA
<213> ORGANISM: Homo sapiens
<220> FEATURE:
<221> NAME/KEY: misc_feature
<222> LOCATION: (1)...(211)
<223> OTHER INFORMATION: n=A,T,C or G

<400> SEQUENCE: 200
cagctcancg ggcgacatgc ccctacaagt tggcanaagn ggctgccact gctgggtttg     60
tgtaagagag gctgctgnca ccattacctg cagaaacctt ctcataggggg ctacgatcgg   120 tactgctagg gggcacatag cgcccatggg tgtggtaggt ggggnactcn ntnataggat   180
ggtaggtatc ccgggctgga aanatgnnca g                                   211
```

```
<210> SEQ ID NO 201
<211> LENGTH: 111
<212> TYPE: DNA
<213> ORGANISM: Homo sapiens

<400> SEQUENCE: 201
ccagtgaaag gaaacaaaac tggcagtttg tccatttgaa tatcagacct agtttcttct     60
taatttccac actatttctc ccatattcct taaacttctt ggcatccacc t             111
```

```
<210> SEQ ID NO 202
<211> LENGTH: 331
<212> TYPE: DNA
<213> ORGANISM: Homo sapiens

<400> SEQUENCE: 202
tgaaaataca gaataccagg tggtcccaaa tgtttgaagt tctttgaaca gaaagagaga     60
ggagagagag agagaggaaa attccctaac ccttggttta aagacaatat tcatttattg   120
ctcaaatgat gcttttaagg gaggacagtg gaataaaata aactttttt ttctccctac    180 aatacataga agggttatca aaccactcaa gtttcaaaat ctttccaggg tccaatatca   240
ctttttttct ttcggttcaa tgaaaagcta aatgtaataa tactaattat agataaaatt   300 ttatttact ttttaaaaat ttgtccagac c                                    331
```

```
<210> SEQ ID NO 203
<211> LENGTH: 491
<212> TYPE: DNA
<213> ORGANISM: Homo sapiens

<400> SEQUENCE: 203
agtcacccag tctacttagt acctggttgc tgcctctgac cttttcagct tgatacctg      60 ggctttagtg taaccaataa atctgtagtg accttacctg tattccctgt gctatcctgt   120
gggaaggtag gaatgggcta agtatgatga atgtataggt tagggatctt ttggttttaa   180
```

-continued

| | |
|---|---|
| atcacagaaa acctaattca aactggctta aaataaaaag gatttattgg ttcatgtaac | 240 |
| tagaaagtcc ataggtagtg ctggctccag gtgaagactt gacccagtag ttcagtatgt | 300 |
| ctctaaatac cggactgact tttttctcac tgttgcatct tctgtaggac catttaagtc | 360 |
| tgggccactt aatggctgcc agcattccta agattacact tttccccatt tatgtccaat | 420 |
| cagaaaaaga aggcatcttt gtaccagaaa tctcagcaaa agccctaata ttcacactga | 480 |
| ttaggacctg c | 491 |

<210> SEQ ID NO 204
<211> LENGTH: 361
<212> TYPE: DNA
<213> ORGANISM: Homo sapiens

<400> SEQUENCE: 204

| | |
|---|---|
| tcccttcctc cccatgtga taaatgggtc cagggctgat caaagaactc tgactgcaga | 60 |
| actgccgctc tcagtggaca gggcatctgt tatcctgaga cctgtggcag acacgtcttg | 120 |
| ttttcatttg attttgtta agagtgcagt attgcagagt ctagaggaat ttttgtttcc | 180 |
| ttgattaaca tgattttcct ggttgttaca tccagggcat ggcagtggcc tcagccttaa | 240 |
| acttttgttc ctactcccac cctcagcgaa ctgggcagca cggggagggt ttggctaccc | 300 |
| ctgcccatcc ctgagccagg taccaccatt gtaaggaaac actttcagaa attcagacct | 360 |
| c | 361 |

<210> SEQ ID NO 205
<211> LENGTH: 471
<212> TYPE: DNA
<213> ORGANISM: Homo sapiens
<220> FEATURE:
<221> NAME/KEY: misc_feature
<222> LOCATION: (2)
<223> OTHER INFORMATION: n=A,T,C or G
<220> FEATURE:
<221> NAME/KEY: misc_feature
<222> LOCATION: (3)
<223> OTHER INFORMATION: n=A,T,C or G

<400> SEQUENCE: 205

| | |
|---|---|
| cnngtacagt tcttcctgga tggccgacac agatcctggg gaaaggcaat cctggcactg | 60 |
| ctctgaaacc agagctcctc ctccctcccc gggcagggtg gagctgagaa gggctgctct | 120 |
| agcgttggga ctccacctcc atacacctga tattttgata gggcaggtcc ctgctatggg | 180 |
| ccactgttct gggcagtata gtatgcttga cagcatcctt ggcatctatc caccagatcc | 240 |
| cagagcaccc gctactagct gtgacaacat cctccaaaca ttgcaaaatt tccctgggaa | 300 |
| ggcaagattg cctcagatgg gagaatcacg ctctagggaa atctgctggt atgagaaccc | 360 |
| caactcccca ctccactgag cctccagatg gcgagcaggc tgcagctcca gcacagacac | 420 |
| gaagctccct ccagccactg acggtccatg gctggggtta cccaggacct c | 471 |

<210> SEQ ID NO 206
<211> LENGTH: 261
<212> TYPE: DNA
<213> ORGANISM: Homo sapiens

<400> SEQUENCE: 206

| | |
|---|---|
| tagagtattt agagtcctga gataacaagg aatccaggca tcctttagac agtcttctgt | 60 |
| tgtcctttct tcccaatcag agatttgtgg atgtgtggaa tgacaccacc accagcaatt | 120 |
| gtagccttga tgagagaatc caattcttca tctccacgaa tagcaagttg caagtgacga | 180 |

```
gggtaatac gctttacctt taagtctttt gatgcatttc ctgccagttc aagtacctct    240
gcggtgaggt actccaggat g                                             261
```

<210> SEQ ID NO 207
<211> LENGTH: 361
<212> TYPE: DNA
<213> ORGANISM: Homo sapiens

<400> SEQUENCE: 207

```
gctctccggg agcttgaaga agaaactggc tacaaagggg acattgccga atgttctcca    60
gcggtctgta tggacccagg cttgtcaaac tgtactatac acatcgtgac agtcaccatt   120
aacggagatg atgccgaaaa cgcaaggccg aagccaaagc caggggatgg agagtttgtg   180
gaagtcattt ctttacccaa gaatgacctg ctgcagagac ttgatgctct ggtagctgaa   240
gaacatctca cagtggacgc cagggtctat tcctacgctc tagcactgaa acatgcaaat   300
gcaaagccat ttgaagtgcc cttcttgaaa ttttaagccc aaatatgaca ctggacctgc   360
c                                                                   361
```

<210> SEQ ID NO 208
<211> LENGTH: 381
<212> TYPE: DNA
<213> ORGANISM: Homo sapiens
<220> FEATURE:
<221> NAME/KEY: misc_feature
<222> LOCATION: (1)...(381)
<223> OTHER INFORMATION: n=A,T,C or G

<400> SEQUENCE: 208

```
agaggagatn tttgccatgc ctgaatnctt tcctatncca ccctancact taacatatta    60
cttagtctgc tttgntaaaa gcaagtatta ccttnaactt gnctcttact cttttgccctt  120 tagctaacta ataaagnttg atntaggcat tattatataa ttctgagtca ttcatggtat   180
ctctcatgtt tgatgtattt tncaaactaa gatctatgat agttttttt ccanagttcc    240 attaaatcat ttatttcctt tactttctca cctctgtnga aacatttaga aactggattt   300
gggaacccan ttttggaaaa ccagattcat agtcatgaaa atggaaactt ncatattctg   360 ttttgaaaa gatgtggacc t                                              381
```

<210> SEQ ID NO 209
<211> LENGTH: 231
<212> TYPE: DNA
<213> ORGANISM: Homo sapiens
<220> FEATURE:
<221> NAME/KEY: misc_feature
<222> LOCATION: (83)
<223> OTHER INFORMATION: n=A,T,C or G

<400> SEQUENCE: 209

```
gtggagagca agtgatttat taaagcaaga cgttgaaacc tttacattct gcagtgaaga    60
tcagggtgtc attgaaagac agnggaaacc aggatgaaag tttttacatg tcacacacta   120
catttcttca atattttcac caggacttcc gcaatgaggc ttcgtttctg aagggacatc   180
tgatccgtgc atctcttcac tcctaacttg gctgcaacag cttccacctg c             231
```

<210> SEQ ID NO 210
<211> LENGTH: 371
<212> TYPE: DNA
<213> ORGANISM: Homo sapiens

<400> SEQUENCE: 210

```
tccatcctgg ttttgcagag atcaggttgt tgacagttcc tggttgaccc acagctaccc      60
atgtcagtta tctccactaa catatccaag aatctttgta ggacaatttc tccacctgca     120
aggtttttta ggtagaactc ttcttttaag gcaattagcc cattgccaaa aggtttttact   180
gtcttaaagc tgtctttctg agatctaatt ccaaggactt ctccacagct aagtgagatg    240
cctcacacca ttaggtgatg ctttggacag aacagagtat tttcatcttg tgtttaaagc    300
aattccttgg cttcggctcc tcaccacttt ctatgccagt ctcccattta tgtccctagt    360
aatgcctatg c                                                         371
```

<210> SEQ ID NO 211
<211> LENGTH: 471
<212> TYPE: DNA
<213> ORGANISM: Homo sapiens

<400> SEQUENCE: 211

```
tttatttttaa aagaaaaaaa ttaaaataga gccaacaaat gcaattaaga aaaaaaaagt     60
attgagacac aagggggacct acatgttctg gtctaagaag catgcaagta ttacaaagca   120
ttccagatac agtatgacag aggaacagtg aacaagcatt ggaacgatgc tctttctttc    180
agaaacggga agtctaacag ttatgttttc acaatggtag tgattaaacc atctttattt   240
ttaaggaatt ttataggaag aatttttagca ccatcattaa aggaaaaata ataataaccctt   300
tttagccctg cctatctcca gtcttggaat aataacagaa gcatagcacc tttcagtatc    360
taaaatataa acaagaatag taagtccatc ccagcttcta gagatgaggt agctcatgct    420
aagaaatgtt gggtcatttt tcctatgaaa gttcaaaggc caaatggtca c             471
```

<210> SEQ ID NO 212
<211> LENGTH: 401
<212> TYPE: DNA
<213> ORGANISM: Homo sapiens

<400> SEQUENCE: 212

```
tggcctgtct ccttcacata gtccatatca ccacaaatca cacaacaaaa gggagaggat     60
atattttggg ttcaaaaaaa gtaaaaagat aatgtagctg catttctttg gttattttgg   120
gccccaaata tttcctcatc ttttttgttgt tgtcatggat ggtggtgaca tggacttgtt   180
tatagaggac aggtcagctc tctggctcgg tgatctacat tctgaagttg tctgaaaatg    240
tcttcatgat taaattcagc ctaaacgttt tgccgggaac actgcagaga caatgctgtg    300
agtttccaac ctcagcccat ctgcgggcag agaaggtcta gtttgtccat caccattatg    360
atatcaggac tggttacttg gttaaggagg ggtctacctc g                        401
```

<210> SEQ ID NO 213
<211> LENGTH: 461
<212> TYPE: DNA
<213> ORGANISM: Homo sapiens
<220> FEATURE:
<221> NAME/KEY: misc_feature
<222> LOCATION: (1)...(461)
<223> OTHER INFORMATION: n=A,T,C or G

<400> SEQUENCE: 213

```
tgtgaagcat acataaataa atgaagtaag ccatactgat ttaatttatt ggatgttatt     60
ttccctaaga cctgaaaatg aacatagtat gctagttatt tttcagtgtt agcctttac    120
tttcctcaca caatttggaa tcatataata taggtacttt gtccctgatt aaataatgtg    180
```

```
acggatagaa tgcatcaagt gtttattatg aaaagagtgg aaaagtatat agcttttanc      240
aaaaggtgtt tgcccattct aagaaatgag cgaatatata gaaatagtgn gggcatttct      300
tcctgttagg tggagtgtat gtgttgacat ttctccccat ctcttccac tctgttttnnt      360 ccccattatt tgaataaagt gactgctgaa nangactttg aatccttatc cacttaattt      420
aatgtttaaa gaaaaaccta taatggaaag tgagactcct t                         461

<210> SEQ ID NO 214
<211> LENGTH: 181
<212> TYPE: DNA
<213> ORGANISM: Homo sapiens

<400> SEQUENCE: 214
cctgagcttc tactcctttc ccttaagatt cctccaaagc accagctcca taaaatcctt      60
cagctcccca gacccacacc aagaacccca catgttaatt ggatcagcca aatctacaag      120
cagataagtc ctaaggagaa tgccgaagcg ttttcttct tcctcaagcc tagcatgaga      180
c                                                                     181

<210> SEQ ID NO 215
<211> LENGTH: 581
<212> TYPE: DNA
<213> ORGANISM: Homo sapiens

<400> SEQUENCE: 215
ctgctttaag aatggttttc cacctttcc ccctaatctc taccaatcag acacatttta       60
ttatttaaat ctgcacctct ctctatttta tttgccaggg gcacgatgtg acatatctgc      120
agtcccagca cagtgggaca aaaagaattt agaccccaaa agtgtcctcg gcatggatct     180
tgaacagaac cagtatctgt catggaactg aacattcatc gatggtctcc atgtattcat     240
ttattcactt gttcattcaa gtatttattg aatacctgcc tcaagctaga gagaaaagag      300
agtgcgcttt ggaaatttat tccagtttc agcctacagc agattatcag ctcggtgact       360
tttctttctg ccaccattta ggtgatggtg tttgattcag agatggctga atttctattc      420
ttagcttatt gtgactgttt cagatctagt ttgggaacag attagaggcc attgtcctct     480
gtcctgatca ggtggcctgg ctgttttcttt ggatccctct gtcccagagc cacccagaac    540
cctgactctt gagaatcaag aaaacaccca gaaaggacct c                        581

<210> SEQ ID NO 216
<211> LENGTH: 281
<212> TYPE: DNA
<213> ORGANISM: Homo sapiens
<220> FEATURE:
<221> NAME/KEY: misc_feature
<222> LOCATION: (1)...(281)
<223> OTHER INFORMATION: n=A,T,C or G

<400> SEQUENCE: 216
ccgatgtcct gcttctgtgg accagggggct cctctgnngg tggcctcaac cacggctgag     60
atccctagaa gtccaggagc tgtggggaag agaagcactt agggccagcc agccgggcac     120
ccccacttgc gccccgaccc acgctcacgc accagacctg cccnggcggt cgctcnaaag     180
ggcgaattct gcagatatcc atcacactgg cggacgctcg agcatgcatc tagagggccc     240
aattcaccct atantgagtc gtattacaat tcactggccg t                        281

<210> SEQ ID NO 217
```

<210> SEQ ID NO 217
<211> LENGTH: 356
<212> TYPE: DNA
<213> ORGANISM: Homo sapiens
<220> FEATURE:
<221> NAME/KEY: misc_feature
<222> LOCATION: (1)...(356)
<223> OTHER INFORMATION: n=A,T,C or G

<400> SEQUENCE: 217

```
atagcaggtt tcaacaattg tcttgtagtt tgnagtaaaa agacataaga aagagaaggt      60
gtggtttgca gcaatccgta gttggtttct caccataccc tgcagttctg tgagccaaag    120
gtcttgcaga aagttaaaat aaatcacaaa gactgctgtc atatattaat tgcataaaca    180
cctcaacatt gctcagagtt tcatccgttt ggttaagaaa acattccttc aattcatcta    240
tggcatttgt agtggcattg tcgtctatga actcttgaag aagttctttg tattcagtct    300
tagacacttg tggattgatt gncttggaaa tcacattctc caataaggga cctcgg        356
```

<210> SEQ ID NO 218
<211> LENGTH: 321
<212> TYPE: DNA
<213> ORGANISM: Homo sapiens

<400> SEQUENCE: 218

```
ttgtccatcg ggagaaaggt gtttgtcagt tgtttcataa accagattga ggaggacaaa     60
ctgctctgcc aatttctgga tttctttatt ttcagcaaac actttcttta aagcttgact   120
gtgtgggcac tcatccaagt gatgaataat catcaagggt tgttgcttg tcttggattt    180
atatagagct tcttcatatg tctgagtcca gatgagttgg tcaccccaac ctctggagag   240
ggtctggggc agtttgggtc gagagtcctt tgtgtccttt ttggctccag gtttgactgt   300
ggtatctctg gacctgcctg g                                             321
```

<210> SEQ ID NO 219
<211> LENGTH: 271
<212> TYPE: DNA
<213> ORGANISM: Homo sapiens
<220> FEATURE:
<221> NAME/KEY: misc_feature
<222> LOCATION: (41)
<223> OTHER INFORMATION: n=A,T,C or G

<400> SEQUENCE: 219

```
ccggttaggt ccacgcgggg gcagtggagg cacaggctca nggtggccgg gctacctggc     60
accctatggc ttacaaagta gagttggccc agtttccttc cacctgaggg gagcactctg   120
actcctaaca gtcttccttg ccctgccatc atctggggtg gctggctgtc aagaaaggcc   180
gggcatgctt tctaaacaca gccacaggag gcttgtaggg catcttccag gtggggaaac   240
agtcttagat aagtaaggtg acttgtctaa g                                  271
```

<210> SEQ ID NO 220
<211> LENGTH: 351
<212> TYPE: DNA
<213> ORGANISM: Homo sapiens
<220> FEATURE:
<221> NAME/KEY: misc_feature
<222> LOCATION: (1)...(351)
<223> OTHER INFORMATION: n=A,T,C or G

<400> SEQUENCE: 220

```
gtcctacgac gaggaccagc ttttcttctt cnacttttcc canaacactc gggtgcctcg     60
cctgcccgaa tttgctgact gggctcagga acagggagat gctcctgcca ttttatttga   120
```

```
caaagagttc tgcgagtgga tgatccagca aatagggcca aaacttgatg ggaaaatccc      180
ggtgtccaga gggttttccta tcgctgaagt gttcacgctg aagccctgg agtttggcaa      240 gcccaacact ttggtctgtt ttgtcagtaa tctcttccca cccatgctga cagtgaactg      300
gtagcatcat tccgtccctg tggaaggatt tgggcctact tttgtctcag a              351
```

<210> SEQ ID NO 221
<211> LENGTH: 371
<212> TYPE: DNA
<213> ORGANISM: Homo sapiens

<400> SEQUENCE: 221

```
gtctgcagaa gcgtgtctga ggtgtccggt ggaggtggca gccgagctct gggactaatc      60
accgtgctgg ggacggcacc gcgtcaggat gcaggcagat ccctgcagaa gtgtctaaaa     120
ttcacactcc tcttctggag ggacgtcgat ggtattagga tagaagcacc aggggacccc     180
acgaacggtg tcgtcgaaac agcagccctt atttgcacac tgggagggcg tgacaccagg     240
aaaaccacaa ttctgtcttt cacgggggc cactgtacac gtctctgtct gggcctcggc      300
cagggtgccg agggccagca tggacaccag gaccagggcg cagatcacct tgttctccat     360
ggtggacctc g                                                          371
```

<210> SEQ ID NO 222
<211> LENGTH: 471
<212> TYPE: DNA
<213> ORGANISM: Homo sapiens

<400> SEQUENCE: 222

```
gtccatgttc catcattaat gttccaacat caccagggac acaaagctgc aaaaatgaga      60
agggaaataa ggttagagaa aggatccggg caatcttaag gactgaggaa gacatgttcc     120 ccaaccttg aactcacaaa ccctgaagct caaggattgc atccttcctc caaatctcac      180
tcaacataat aagtgcagaa caacatgcca agcactgta tgaagcacta gggacaaaga     240
caaggtcaaa atccttgtaa ccaaatttaa tggtattgta atgcagtgtt aacacaggac     300
agtaacagaa cacccaagaa ccaaacagaa gagggtaggg ataagcataa atgaagtaac     360
atgaaataaa cttccaaatg gaaaacttgt ccatacccc agggcaagtc aactacagtc      420
tcccaaagga cataaattcc acttagggca cactagacag aaaacaatat t              471
```

<210> SEQ ID NO 223
<211> LENGTH: 411
<212> TYPE: DNA
<213> ORGANISM: Homo sapiens

<400> SEQUENCE: 223

```
agttgctcta caatgacaca caatcccgt taaataaatt ataaacaagg gtcaattcaa       60
atttgaagta atgttttagt aaggagagat tagaagacaa caggcatagc aaatgacata     120
agctaccgat taactaatcg gaacatgtaa aacagttaca aaaataaacg aactctcctc     180
ttgtcctaca atgaaagccc tcatgtgcag tagagatgca gtttcatcaa agaacaaaca     240
tccttgcaaa tgggtgtgac gcggttccag atgtggattt ggcaaaacct catttaagta     300
aaaggttagc agagcaaagt gcggtgcttt agctgctgct tgtgccgctg tggcgtcggg     360
gaggctcctg cctgagcttc cttccccagc tttgctgcct gagaggaacc a              411
```

<210> SEQ ID NO 224

```
<211> LENGTH: 321
<212> TYPE: DNA
<213> ORGANISM: Homo sapiens
<220> FEATURE:
<221> NAME/KEY: misc_feature
<222> LOCATION: (31)
<223> OTHER INFORMATION: n=A,T,C or G

<400> SEQUENCE: 224
ggtctgaagt tgataacaa agaaatatat ntaagacaaa aatagacaag agttaacaat      60
aaaaacacaa ctatctgttg acataacata tggaaacttt ttgtcagaaa gctacatctt    120
cttaatctga ttgtccaaat cattaaaata tggatgattc agtgccattt tgccagaaat    180
tcgtttggct ggatcataga ttaacatttt cgagagcaaa tccaagccat tttcatccaa    240
gttttttgaca tgggatgcta ggcttcctgg tttccatttg ggaaatgtat tcttatagtc    300
ctgtaaagat tccacttctg g                                               321

<210> SEQ ID NO 225
<211> LENGTH: 251
<212> TYPE: DNA
<213> ORGANISM: Homo sapiens
<220> FEATURE:
<221> NAME/KEY: misc_feature
<222> LOCATION: (34)
<223> OTHER INFORMATION: n=A,T,C or G

<400> SEQUENCE: 225
atgtctgggg aaagagttca ttggcaaaag tgtnctccca agaatggttt acaccaagca      60
gagaggacat gtcactgaat ggggaaaggg aaccccgta tccacagtca ctgtaagcat     120
ccagtaggca ggaagatggc tttgggcagt ggctggatga agcagattt gagataccca    180
gctccggaac gaggtcatct tctacaggtt cttccttcac tgagacaatg aattcagggt    240
gatcattctc t                                                          251

<210> SEQ ID NO 226
<211> LENGTH: 331
<212> TYPE: DNA
<213> ORGANISM: Homo sapiens
<220> FEATURE:
<221> NAME/KEY: unsure
<222> LOCATION: (1)...(331)
<223> OTHER INFORMATION: n=A,T,C or G

<400> SEQUENCE: 226
gttaggtccc aggccccccg ccaagnggtt accnnnntna ccactcctga cccaaaaatc      60
aggcatggca ttaaaacgtt gcaaattcct ttactgttat ccccccacc accaggacca    120
tgtagggtgc agtctttact ccctaacccg tttcccgaaa aaggtgctac ctcctttcca    180
gacagatgag agagggcagg acttcaggct ggatcccaca ctgggctctc cctccccag    240
cctggagcac gggaggggag gtgacggctg gtgactgatg gatgggtagt gggctgagaa    300
gagggggacta ggaagggcta ttccaggctc a                                    331

<210> SEQ ID NO 227
<211> LENGTH: 391
<212> TYPE: DNA
<213> ORGANISM: Homo sapiens

<400> SEQUENCE: 227
aggtctgccc ttgaagtata ggaaggaatc atagttggag gacttctgca ttatttgttg      60
gctgaagcta gaagtgcaac cccctcctga tttctgcagc aagatgaact gccttatccc    120
```

| | |
|---|---|
| cagcccgcag gaatgttcat atctgagcaa tcaatgggca ctgtgttcaa ccacgccatt | 180 |
| ttcaagattg gctccttaaa ccacccacaa ggcaccagct ctgggagaag ctgcagggag | 240 |
| aagagaacaa agccctcgct gtgatcagga tgggtgtctc atacctttc tctgggtca | 300 |
| ttccaggtat gagacagagt tgaacctgcg catgagcgtg gaggccgaca tcaacggcct | 360 |
| gcgcagggtg ctggatgagc tgaccctgga c | 391 |

<210> SEQ ID NO 228
<211> LENGTH: 391
<212> TYPE: DNA
<213> ORGANISM: Homo sapiens
<220> FEATURE:
<221> NAME/KEY: misc_feature
<222> LOCATION: (35)
<223> OTHER INFORMATION: n=A,T,C or G

<400> SEQUENCE: 228

| | |
|---|---|
| gttgtccata gccacctcct gggatagaag ctttntagtt catagttcga ttagtgtgtc | 60 |
| cttaggacat aggtccagcc ctacagatta gctgggtgaa aaggcaagt gtctcgacag | 120 |
| ggcttagtct ccaccctcag gcatggaacc attcagggtg aagcctggga tgtgggcaca | 180 |
| ggagactcag gctgatataa aaataacaaa atcagtaata aaaaaattat aaaacctgtt | 240 |
| gcttgtctga atagatttga gcaacagtct tgcttttgtt aaaatcctgg agccgttaag | 300 |
| tcctgaatat tcttctggac atcattgctg gctggagaaa ggagcccag gcccggctcg | 360 |
| gctgacatct gtcaggtttg gaagtctcat c | 391 |

<210> SEQ ID NO 229
<211> LENGTH: 341
<212> TYPE: DNA
<213> ORGANISM: Homo sapiens
<220> FEATURE:
<221> NAME/KEY: misc_feature
<222> LOCATION: (202)
<223> OTHER INFORMATION: n=A,T,C or G

<400> SEQUENCE: 229

| | |
|---|---|
| gtccatggct tctcacccag acagtctttc tgggcaactt ggggaagccc ctgttctgct | 60 |
| caagtctcac cccatggaag aggtgggga aggggccctt ggttttcag gaagacgggt | 120 |
| tggagagcac gagtcactac aaagcagtaa aagtgaatgg tgtctccagg ggctgggtcc | 180 |
| agaacaccgc ggagagcccc anccataaag gtgtgttccg cctctggcct gcaggaatct | 240 |
| ctttgaatct ctttgattgg tggctccaag agcaatggga agtcaacagc caggaggctg | 300 |
| gactgggttc cctgggaccc cgaggtccca gaggctgctg g | 341 |

<210> SEQ ID NO 230
<211> LENGTH: 511
<212> TYPE: DNA
<213> ORGANISM: Homo sapiens

<400> SEQUENCE: 230

| | |
|---|---|
| gtccaagcca aggaaaccat tcccttacag gagacctccc tgtacacaca ggaccgcctg | 60 |
| gggctaaagg aaatggacaa tgcaggacag ctagtgtttc tggctacaga aggggaccat | 120 |
| cttcagttgt ctgaagaatg gttttatgcc cacatcatac cattccttgg atgaaacccg | 180 |
| tatagttcac aatagagctc agggagcccc taactcttcc aaaccacatg ggagacagtt | 240 |
| tccttcatgc ccaagcctga gctcagatcc agcttgcaac taatccttct atcatctaac | 300 |

-continued

```
atgccctact tggaaagatc taagatctga atcttatcct ttgccatctt ctgttaccat    360
atggtgttga atgcaagttt aattaccatg gagattgttt tacaaacttt tgatgtggtc    420
aagttcagtt ttagaaaagg gagtctgttc cagatcagtg ccagaactgt gcccaggccc    480
aaaggagaca actaactaaa gtagtgagat a                                   511
```

<210> SEQ ID NO 231
<211> LENGTH: 311
<212> TYPE: DNA
<213> ORGANISM: Homo sapiens

<400> SEQUENCE: 231

```
ggtccaagta agctgtgggc aggcaagccc ttcggtcacc tgttggctac acagacccct     60
cccctcgtgt cagctcaggc agctcgaggc ccccgaccaa cacttgcagg ggtccctgct    120
agttagcgcc ccaccgccgt ggagttcgta ccgcttcctt agaacttcta cagaagccaa    180
gctccctgga gccctgttgg cagctctagc tttgcagtcg tgtaattggc ccaagtcatt    240 gttttttctcg cctcactttc caccaagtgt ctagagtcat gtgagcctcg tgtcatctcc    300
ggggtggacc t                                                         311
```

<210> SEQ ID NO 232
<211> LENGTH: 351
<212> TYPE: DNA
<213> ORGANISM: Homo sapiens

<400> SEQUENCE: 232

```
tcgtttagct aataatccct tccttgatga tacactccaa cttcttgttt ttctttattt     60
ctaaaaagcg gttctgtaac tctcaatcca gagatgttaa aaatgtttct aggcacggta    120
ttagtaaatc aagtaaattt catgtcctct taaaggacaa acttccagag atttgaatat    180 aaattttat atgtgttatt gattgtcgtg taacaaatgg cccccacaaa ttagtagctt     240
aaaatagcat ttatgatgtc actgttttct ttgccttttc attaatgttc tgtacagacc    300
tatgtaaaca acttttgtat atgcatatag atagcttttt tgagggtat a              351
```

<210> SEQ ID NO 233
<211> LENGTH: 511
<212> TYPE: DNA
<213> ORGANISM: Homo sapiens

<400> SEQUENCE: 233

```
aggtctggat gtaaggatgg atgctctcta tacatgctgg gttggggatg ctgggactgc     60
acagccaccc ccagtatgcc gctccaggac tctgggacta gggcgccaaa gtgtgcaaat    120
gaaaatacag gatacccagg gaactttgaa tttcagattg tgaaagaaa acaaatcttg     180 agactccaca atcaccaagc taaggaaaa agtcaagctg ggaactgctt agggcaaagc     240
tgcctcccat tctattcaca gtcatccccc tgaggctcac ctgcatagct gattgcttcc    300
tttcccctat cgcttctgta aaaatgcaga ctcactgagc cagactaaat tgtgtgttca    360
gtggaaggct gatcaagaac tcaaaagaat gcaaccttt gtctcttatc tactacaacc     420
aggaagcccc cacttaaggg ttgtcccacc ttactggact gaaccaaggt acatcttaca    480
cctactgatt gatgtctcat gtcccctaa g                                    511
```

<210> SEQ ID NO 234
<211> LENGTH: 221
<212> TYPE: DNA
<213> ORGANISM: Homo sapiens

<400> SEQUENCE: 234

| caggtccagc gaagggcctt cataggctac accaagcatg tccacataac cgaggaagct | 60 |
| ctctccatca gcatagcctc cgatgaccat ggtgttccac aaagggttca tcttcgagcg | 120 |
| ccggctgtac atggccctgg tcagccatga atgaatagct ctaggactat agctgtgtcc | 180 |
| atctcccaga agctcctcat caatcaccat ctggccgaga c | 221 |

<210> SEQ ID NO 235
<211> LENGTH: 381
<212> TYPE: DNA
<213> ORGANISM: Homo sapiens
<220> FEATURE:
<221> NAME/KEY: misc_feature
<222> LOCATION: (33)
<223> OTHER INFORMATION: n=A,T,C or G

<400> SEQUENCE: 235

| ggtccaagaa agggacatct atgtgaaagt ganactgaga cagtgctggt cacaggtcat | 60 |
| gctgcagaat aatacattcc caggcactgt cacgtgggg acccaagagg ccccaggagt | 120 |
| gacctataac ctctccagaa agaccactct gtgtggcatc acagtccaca cagtttaagg | 180 |
| aaatatttag acttaacaat cagacaccag ctcttactca cacttacact cacagcccac | 240 |
| acacaagtgt gcaaacatac acacacatat atatttcctg atacattcat ggaatatcag | 300 |
| agccctgccc tgaagtcgtt agtgtctctg ctccccaaac cgctgctccc acattggcta | 360 |
| agctcccctca agagacctca g | 381 |

<210> SEQ ID NO 236
<211> LENGTH: 441
<212> TYPE: DNA
<213> ORGANISM: Homo sapiens

<400> SEQUENCE: 236

| aggtcctgtt gcccctttct tttgcccaac ttcgccattt gggaattgga atatttaccc | 60 |
| aacacctgta ctgcattgaa tattggaagc aaataacttg gctttgatct tataggctca | 120 |
| cagatggagg aacgtacctt gaagttcaga tgagatttcg gacttttgag ttgatgctga | 180 |
| aacagcttga gattttttggg gactactgag agatgataat tgtattgtgc aatatgagaa | 240 |
| ggacatgaga tttggtgggc ataggtgtga atgacattg tttggatgtg tttaccctcc | 300 |
| aaatctcttg ttgaatgtga tcttaaacgt tggtggtggg cctagtggaa ggtgttgaat | 360 |
| catgggggtg gactcttcat aatttgctta gctccatccc cttggtgatg agcaagtcct | 420 |
| tgctctgttg tgtcacatga g | 441 |

<210> SEQ ID NO 237
<211> LENGTH: 281
<212> TYPE: DNA
<213> ORGANISM: Homo sapiens
<220> FEATURE:
<221> NAME/KEY: misc_feature
<222> LOCATION: (1)...(281)
<223> OTHER INFORMATION: n=A,T,C or G

<400> SEQUENCE: 237

| tcctaaaaaa ttagctgacc ttgttaaaaa tgttggcgtg agcagtatat tattacctat | 60 |
| cttttttttat tgtgtgtgtg ngtgtgtgtn ttaaactaat tggctgaaat atctgcctgt | 120 |
| ttccctcttt acatttttct tgtttctttc cttatttatc tttgtccatc ttgagatcta | 180 |

```
ctgtaaagtg aatnttttaa tgaaaacann nccaagttnt actctcactg ggnttgggac    240
atcagatgta attgagaggc aacaggtaa gtcttcatgt c                        281
```

<210> SEQ ID NO 238
<211> LENGTH: 141
<212> TYPE: DNA
<213> ORGANISM: Homo sapiens
<220> FEATURE:
<221> NAME/KEY: misc_feature
<222> LOCATION: (1)...(141)
<223> OTHER INFORMATION: n=A,T,C or G

<400> SEQUENCE: 238

```
gtctgcctcc tcctactgtt tccctctatn aaaaagcctc cttggcgcag gttccctgag    60
ctgtgggatt ctgcactggt gcttnggatt ccctgatatg ttccttcaaa tccactgaga   120
attaaataaa catcgctaaa g                                             141
```

<210> SEQ ID NO 239
<211> LENGTH: 501
<212> TYPE: DNA
<213> ORGANISM: Homo sapiens
<220> FEATURE:
<221> NAME/KEY: misc_feature
<222> LOCATION: (1)...(501)
<223> OTHER INFORMATION: n=A,T,C or G

<400> SEQUENCE: 239

```
aacaatctaa acaaatccct cggttctann atacaatgga ttccccatat tggaaggact    60
ctgangcttt attcccccac tatgcntatc ttatcatttt attattatac acacatccat   120
cctaaactat actaaagccc ttttcccatg catggatgga aatggaagat ttttttttaa   180
cttgttctag aagtcttaat atgggctgtt gccatgaagg cttgcagaat tgagtccatt   240
ttctagctgc ctttattcac atagtgatgg ggtactaaaa gtactgggtt gactcagaga   300
gtcgctgtca ttctgtcatt gctgctactc taacactgag caacactctc ccagtggcag   360
atcccctgta tcattccaag aggagcattc atcccttttgc tctaatgatc aggaatgatg   420
cttattagaa acaaactgc ttgacccagg aacaagtggc ttagcttaag naaacttggc    480
tttgctcana tccctgatcc t                                             501
```

<210> SEQ ID NO 240
<211> LENGTH: 451
<212> TYPE: DNA
<213> ORGANISM: Homo sapiens

<400> SEQUENCE: 240

```
tgtcctgaaa ggccattact aatagaaaca cagcctttcc aatcctctgg aacatattct    60
gtctgggttt ttaatgtctg tggaaaaaaa ctaaacaagt ctctgtctca gttaagagaa   120
atctattggt ctgaaggttt ctgaacctct ttctggttct cagcagaagt aactgaagta   180
gatcaggaag gggctgcctc aggaaaattc ctagatccta ggaattcagt gagaccctgg   240
gaaggaccag catgctaatc agtgtcagtg aatccacagt ctttacttcc tgcctcataa   300
agggccaggt ctccccagta ccaagtcctt tcctcatgaa gttgtgttgc ctcaggctgt   360
ttagggacca ttgcctgtct tggtcacatg agtctgtctc cttactttag tccctgggca   420
atccttgctt aatgcttttg ttgactcaac g                                  451
```

<210> SEQ ID NO 241
<211> LENGTH: 411

```
<212> TYPE: DNA
<213> ORGANISM: Homo sapiens
<220> FEATURE:
<221> NAME/KEY: misc_feature
<222> LOCATION: (1)...(411)
<223> OTHER INFORMATION: n=A,T,C or G

<400> SEQUENCE: 241
aatctccagt gtgatggtat cggggttaga gcttcaatct ccagtgtgat ggtactgcag      60
cnagagcttc aatctccagt gngatggtat tagggttaga tcttcaatct ccagtgtgat     120
ggtatcaggg ttagagcttc agcctccagt gtgatggtat cagggttaga gcttcagcct     180
ccagtgtgat ggtatcgggg ttagatcttc aatccccagt ggtggtggtt agagcttcaa     240
tctccagtgt gatggtattg gggttagagc ttcaatctcc agtctgatgg tgtttcggga     300
tggggctttt aagatgtaat tagggtttaa gatcataagg gacctggtct gatggggatt     360
agtncgcttn tatgaagaga cacangaggg cttgctctat ctctgactct c              411

<210> SEQ ID NO 242
<211> LENGTH: 351
<212> TYPE: DNA
<213> ORGANISM: Homo sapiens

<400> SEQUENCE: 242
ttccccttca caacagtaga gacctacaca gtgaactttg gggacttctg agatcagcgt      60
cctaccaaga ccccagccca actcaagcta cagcagcagc acttcccaag cctgctgacc     120
acagtcacat cacccatcag cacatggaag gcccctggta tggacactga aggaagggc      180 tggtcctgcc cctttgaggg ggtgcaaaca tgactgggac ctaagagcca gaggctgtgt     240
agaggctcct gctccacctg ccagtctcgt aagaaatggg gttgctgcag tgttggagta     300
ggggcagagg gagggagcca aggtcactcc aataaaacaa gctcatggca c              351

<210> SEQ ID NO 243
<211> LENGTH: 241
<212> TYPE: DNA
<213> ORGANISM: Homo sapiens

<400> SEQUENCE: 243
gtctgtgctt tatcaggaaa agcacaagaa tatgttttc tacctaaaac cctcttctac       60
tttaaaaatg gtttgctgaa ttttttctatg tttttaaaat gtttttatgc ttttttttaa    120
acacgtaaag gatggaacct aatcctctcc cgagacgcct cctttgtgtt aatgcctatt     180
cttacaacag agaaacaagt acattaatat aaaaacgagt tgattattgg ggtataaaat     240
a                                                                     241

<210> SEQ ID NO 244
<211> LENGTH: 301
<212> TYPE: DNA
<213> ORGANISM: Homo sapiens

<400> SEQUENCE: 244
ggtccagagc aatagcgtct gtggtgaagc gcctgcactc ctcgggagac atgcctggct      60
tatatgctgc atccacataa ccatagataa aggtgctgcc ggagccacca atggcaaaag     120
gctgtcgagt cagcattcct cccagggttc catatacctg acctccttca cgttggtccc     180
agccagctac catgagatgt gcagacaagt cctctcgata tttatagctg atatttctca     240
ccacatttgc agcagccaaa acaagtggag gttcctccag ttctatccca tggagctcca     300
```

-continued g                                                                301

<210> SEQ ID NO 245
<211> LENGTH: 391
<212> TYPE: DNA
<213> ORGANISM: Homo sapiens

<400> SEQUENCE: 245
ctgacactgc tgatgtgggc cgggggcgc cgaggcacaa ctggtggccg gaccattgag     60
gcacctggag ggtaggcagc ttgtggtgca gacaccacag agagagaaaa gttggatgga    120
gtggtgggaa taatcagggt ggcacactgt gcctagaagc ttccagggcc accaagagaa    180
tgggaaggga aactacaaca ttcacaacag aaataggagt caattcactt agacccagaa    240
ctccagaaag ggggagtgta ggaatctaca atttcaaagc cagctcgtgt ctacctagag    300
ccccaaactg cataagcacc aggattgtac accttagtcc ctcaagatag tttcaagtga    360
gcgtgcaatt cactcttaca gaggagggcc t                                   391

<210> SEQ ID NO 246
<211> LENGTH: 291
<212> TYPE: DNA
<213> ORGANISM: Homo sapiens
<220> FEATURE:
<221> NAME/KEY: misc_feature
<222> LOCATION: (1)...(291)
<223> OTHER INFORMATION: n=A,T,C or G

<400> SEQUENCE: 246
tcctccacag gggaagcagg aagttngacc agcttcaggc tggaacgtgc ccagggcaca     60
gagctggcaa ggtgcaaagn cntctgcaga atattcacca ggttgacaca gacctccaca    120
ttcagacata ttccaagctt ctggggtctt cagggcccca gaatttcctg gtcttgggca    180
tggtncacaa gtcatttgtc cttcctcatt ttggaaggtt ccatttggac ataaaatgca    240
agcgttctcg tgctncatna taataggtcc cagcctgcac tgacacattt g             291

<210> SEQ ID NO 247
<211> LENGTH: 471
<212> TYPE: DNA
<213> ORGANISM: Homo sapiens
<220> FEATURE:
<221> NAME/KEY: misc_feature
<222> LOCATION: (1)...(471)
<223> OTHER INFORMATION: n=A,T,C or G

<400> SEQUENCE: 247
cactgagtga atgagtatat aatttatgaa aacagaaaag tgctttggaa aaaaaaaag      60 acaacaggag tacatacagn gaaccaaaaa gagtgtacca ggaggagcan accctgaaca    120
gttanaacta tggaaatcgc tatgctttgt gttgtcacag gagttaaaat aggaataccc    180
tgcatacaat aaatatttat tggataaata actaagcctg atacccttt caatgcgtta     240 tacanactnt atcatcacac cactaatcta agttctcana agttaaacat tacaagactt    300
cagaacaaca taggcgtntt tggctccatt taacanaana aggaccatag tgatcattta    360
atctctatga gtctgtctta tcttctggaa aaggggccta acaccatttc cttttgcaaa    420
aaggtagctg ccttgcttcc agttctacca tcctntagca acccatcttt n             471

<210> SEQ ID NO 248
<211> LENGTH: 551
<212> TYPE: DNA
<213> ORGANISM: Homo sapiens

<400> SEQUENCE: 248

```
ccatgggatc aggaatgggg tcaggtcagt tgacctgagc atacccatta aacatgttca      60
aatgtcccca tcccacccac tcacatgaca tggctcccga gccctgagat ctgtatccca     120
agaacctcag ttgagaaata tttatggcag cttcactgtt gctcaagagc ctgggtattg     180
tagcagcctg ggggcaggtt gtccctaatg ttctccaagt tcttcacatc agccagaatc     240
ccatctatgc ttgtctccag caaatggagg tggcccctct gctgacgtgc cctctcttcc     300
agctctgaca tcatgggccg cagttggctg ttgatctggg tcttggctcg ggaaagcttc     360
tgctccagta agaccagccc ctcttcatct acactgagag gctggtccat cagatgcagg     420
aggccgtcta atgtgttgag tgtgtcttgg attgtaaccc cagcgttctt ggctctggta     480
tcaaccttct gggcttctgt aatcaccatc tgtactgcat ccatattcgt gtcgaactcc     540
agctccttcc t                                                          551
```

<210> SEQ ID NO 249
<211> LENGTH: 181
<212> TYPE: DNA
<213> ORGANISM: Homo sapiens
<220> FEATURE:
<221> NAME/KEY: misc_feature
<222> LOCATION: (1)...(181)
<223> OTHER INFORMATION: n=A,T,C or G

<400> SEQUENCE: 249

```
atntccagag ggaccgtaag actggtacaa gtttacacca taagaggcga cgtggtcagc      60
cacaatgtct tcacctccac aggggctcat cacggnggtc agggcaaggg cccccagcat     120
cagagctttg tttaggatca tcctcttccc aaggcagcct tagcagttgc tgacctgccc     180
g                                                                     181
```

<210> SEQ ID NO 250
<211> LENGTH: 551
<212> TYPE: DNA
<213> ORGANISM: Homo sapiens

<400> SEQUENCE: 250

```
tctgtagcta ggatgagctg gctctcaagc aaaagtttgt cttcctgggt ccatttgtgg      60
ttatcacttg ttattgaatg tacatcacaa attaaagtct gcattgttgg acgtaagaga     120
atgtgccgac tttggtaacc aggagatttc atgttactgg actgcctgta gtcacgtatt     180
tctgctatga cacatccgca atgaaaaata ttaacctgag atttttctag gagatcaacc     240
aaaataggag gtaattcttc tgcatccaaa tattcaagca actctccttc ttcatagggc     300
agtcgaatgg tctcggaatc tgatccgttt ttccccctga gcatcagaga atatccctca     360
tttcctgggt atagattgac cactaaacat gacaaagtct cttgcataac aagcttctct     420
aacaagttca catttcttct taatttctta acttcaggtt cttttcaca ttcttcaata      480
tacaagtcat aaagttttg aaatacagat tttcttccac ttgataggta tttcctttta     540
ggaggtctct g                                                          551
```

<210> SEQ ID NO 251
<211> LENGTH: 441
<212> TYPE: DNA
<213> ORGANISM: Homo sapiens

<400> SEQUENCE: 251

-continued

| | |
|---|---|
| tgtctgctct cccatcctgg ttactatgag tcgctcttgg cagaaaggac cacagatgga | 60 |
| gagcttggca ctcgctccaa ctttgccgaa aagaggacaa ccaccaaagt agtaggtaaa | 120 |
| aacacaattt tagcagcagt gaaataaaaa gaggaagtga ggatggggcc aggccgcaac | 180 |
| tataattaaa ctgtctgttt aggagaagct gaatccagaa gaaacacaag ctgtaaagtg | 240 |
| agagaggaca gggagcaggg cctttggaga gcaggagagg acaggctgtc accaagcgct | 300 |
| gctcggactc tgccctgaaa gatttgaatt ggacactgtc cagtcacgtg tgtggcaaac | 360 |
| cgtactccaa gcactttct cacggcagag gaaggagctg ccatggctgt accctgaac | 420 |
| gtttgtgggg ccagcgatgt g | 441 |

<210> SEQ ID NO 252
<211> LENGTH: 406
<212> TYPE: DNA
<213> ORGANISM: Homo sapiens

<400> SEQUENCE: 252

| | |
|---|---|
| ttttttttg aacaagtaaa aatttcttta tttgctgaca ataagataac ctacagggaa | 60 |
| aacctgatga aatctattaa aaagttacta aaactaataa aagaatttag gaaggttata | 120 |
| gaatgtaaga ccaagacaca aaaatcaatt acatttctat ataatagcaa tgaacagata | 180 |
| ctgaaatttt aaaaactaaa tcattttaca aaagtatcac aatatgaaac actccgggat | 240 |
| aaattggata aaagatgtgc aagactgtac aaaagctaca aaacatttat gaaggaaatt | 300 |
| ggaagataga aacaagatag aaaatgaaaa tattgtcaag agtttcagat agaaaatgaa | 360 |
| aaacaagcta agacaagtat tggagaagta tagaagatag aaaaat | 406 |

<210> SEQ ID NO 253
<211> LENGTH: 544
<212> TYPE: DNA
<213> ORGANISM: Homo sapiens
<220> FEATURE:
<221> NAME/KEY: misc_feature
<222> LOCATION: (224)
<223> OTHER INFORMATION: n=A,T,C or G

<400> SEQUENCE: 253

| | |
|---|---|
| gaaggagttc agtagcaaag tcacacctgt ccaattccct gagctttgct cactcagcta | 60 |
| atgggatggc aaaggtggtg gtgctttcat cttcaggcag aagcctctgc ccatccccct | 120 |
| caagggctgc aggcccagtt tcatgctgc ccttgggtgg gcatctgtta acagaggaga | 180 |
| acgtctgggt ggcggcagca gctttgctct gagtgcctac aaanctaatg cttggtgcta | 240 |
| gaaacatcat cattattaaa cttcagaaaa gcagcagcca tgttcagtca ggctcatgct | 300 |
| gcctcactgc ttaagtgcct gcaggagccg cctgccaagc tcccttcct acacctggca | 360 |
| cactggggtc tgcacaaggc tttgtcaacc aaagacagct tcccccttt gattgcctgt | 420 |
| agactttgga gccaagaaac actctgtgtg actctacaca cacttcaggt ggtttgtgct | 480 |
| tcaaagtcat tgatgcaact tgaaaggaaa cagtttaatg gtggaaatga actaccattt | 540 |
| ataa | 544 |

<210> SEQ ID NO 254
<211> LENGTH: 339
<212> TYPE: DNA
<213> ORGANISM: Homo sapiens

<400> SEQUENCE: 254

| | |
|---|---|
| tggcattcag ggcagtgtct tctgcatctc ctaggaacct cgggagcggc agctccggcg | 60 |

```
cctggtagcg agaggcgggt tccggagatc ccggcctcac ttcgtcccac tgtggttagg      120
ggtgagtcct gcaaatgtta agtgatttgc tcaaggtgcc catttcgcag gaattggagc      180
ccaggccagt tctctgagcc tatcattagg gctaaaggag tgcgtgatca gaatggtgtc      240
tggacggttc tacttgtcct gcctgctgct ggggtccctg gctctatgt gcatcctctt       300 cactatctac tggatgcagt actggcgtgg tggctttgc                             339
```

```
<210> SEQ ID NO 255
<211> LENGTH: 405
<212> TYPE: DNA
<213> ORGANISM: Homo sapiens
<220> FEATURE:
<221> NAME/KEY: misc_feature
<222> LOCATION: (1)...(405)
<223> OTHER INFORMATION: n=A,T,C or G

<400> SEQUENCE: 255 gaggttttt nttttttttt tttttttttt caattaaana tttgatttat tcaagtatgt       60
gaaaacattn tacaatggaa acttttntta aatgctgcat gtnctgtgct atggaccacn      120
cacatacagc catgctgttt caaaaaactt gaaatgccat tgatagttta aaaactntac     180
ncccgatgga aaatcgagga aaacaattta atgtttcatn tgaatccana ggngcatcaa     240
attaaatgac agctccactt ggcaaataat agctgttact tgatggtatc caaaaaaaaa    300
tggttgggga tggataaatt caaaaatgct tccccaaagg ngggnggttt ttaaaaagtt    360
tcaggncaca acccttgcan aaaacactga tgcccaacac antga                    405
```

```
<210> SEQ ID NO 256
<211> LENGTH: 209
<212> TYPE: DNA
<213> ORGANISM: Homo sapiens
<220> FEATURE:
<221> NAME/KEY: misc_feature
<222> LOCATION: (6)
<223> OTHER INFORMATION: n=A,T,C or G

<400> SEQUENCE: 256
gggcangtct ggtcctctcc ccacatgtca cactctcctc agcctctccc ccaaccctgc      60
tctccctcct cccctgccct agcccaggga cagagtctag gaggagcctg gggcagagct    120
ggaggcagga agagagcact ggacagacag ctatggtttg gattggggaa gaggttagga    180
agtaggttct taaagacct ttttagta                                         209
```

```
<210> SEQ ID NO 257
<211> LENGTH: 343
<212> TYPE: DNA
<213> ORGANISM: Homo sapiens
<220> FEATURE:
<221> NAME/KEY: misc_feature
<222> LOCATION: (1)...(343)
<223> OTHER INFORMATION: n=A,T,C or G

<400> SEQUENCE: 257
tctggacacc ataatccctt ttaagtggct ggatggtcac acctctccca ttgacaagct      60
gggttaagtc aataggttga ctaggatcaa cacgacccaa atcaataaga tactgcagtc    120
tattgagact caaaggctta tactggcgtc tgaaactatg tccttcgtta aacccgtatt    180
ttgggattcg gatgtaaaat ggagtctggc ctccctcaaa gcccaagcgg ggccgggttc    240
ctctttgcct ttctccttta tggcctctgc cacatttct acctcttctc cgacctcttg      300
```

```
gtcttntctc nggtttcttg gagccgggat tcggctttaa gtn          343
```

<210> SEQ ID NO 258
<211> LENGTH: 519
<212> TYPE: DNA
<213> ORGANISM: Homo sapiens

<400> SEQUENCE: 258

```
gcggcttctg acttctagaa gactaaggct ggtctgtgtt tgcttgtttg cccacctttg     60
gctgataccc agagaacctg ggcacttgct gcctgatgcc caccsctgcc agtcattcct   120
ccattcaccc agcgggaggt gggatgtgag acagcccaca ttggaaaatc cagaaaaccg   180
ggaacaggga tttgcccttc acaattctac tccccagatc ctctcccctg acacaggag    240
acccacaggg caggacccta agatctgggg aaaggaggtc ctgagaacct tgaggtaccc   300
ttagatcctt ttctacccac tttcctatgg aggattccaa gtcaccactt ctctcaccgg   360
cttctaccag ggtccaggac taaggcgttt tctccatagc ctcaacattt tgggaatctt   420
cccttaatca cccttgctcc tcctgggtgc ctggaagatg gactggcaga gacctctttg   480
ttgcgttttg tgctttgatg ccaggaatgc cgcctagtt                           519
```

<210> SEQ ID NO 259
<211> LENGTH: 371
<212> TYPE: DNA
<213> ORGANISM: Homo sapiens

<400> SEQUENCE: 259

```
attgtcaact atatacacag tagtgaggaa taaaatgcac acaaaacaat ggatagaata     60
tgaaaatgtc ttctaaatat gaccagtcta gcatagaacc ttcttctctt ccttctcagg   120
tcttccagct ccatgtcatc taacccactt aacaaacgtg gacgtatcgc ttccagaggc   180
cgtcttaaca actccatttc caaagtcat ctccagaaga catgtatttt ctatgatttc    240
ttttaaacaa atgagaattt acaagatgtg taactttcta actctatttt atcatacgtc   300
ggcaacctct ttccatctag aagggctaga tgtgacaaat gttttctatt aaaaggttgg   360
ggtggagttg a                                                         371
```

<210> SEQ ID NO 260
<211> LENGTH: 430
<212> TYPE: DNA
<213> ORGANISM: Homo sapiens
<220> FEATURE:
<221> NAME/KEY: misc_feature
<222> LOCATION: (1)...(430)
<223> OTHER INFORMATION: n=A,T,C or G

<400> SEQUENCE: 260

```
ttggattttt tgacttgcga tttcagttttt tttactttttt tttttttttt ttttganaaa    60
tactatattt attgtcaaag agtggtacat aggtgagtgt tcatcttccc tctcatgccg   120
gtatactctg cttcgctgtt tcagtaaaag ttttccgtag ttctgaacgt cccttgacca   180
caccataana caagcgcaag tcactcanaa ttgccactgg aaaactggct caactatcat   240
ttgaggaaag actganaaag cctatcccaa agtaatggac atgcaccaac atcgcggtac   300
ctacatgttc ccgttttttct gccaatctac ctgtgtttcc aagataaatt accacccagg   360
gagtcacttc ctgctatgtg aacaaaaacc cggtttcttt ctggaggtgc ttgactactc   420
tctcgngagc                                                           430
```

<210> SEQ ID NO 261
<211> LENGTH: 365
<212> TYPE: DNA
<213> ORGANISM: Homo sapiens
<220> FEATURE:
<221> NAME/KEY: misc_feature
<222> LOCATION: (178)
<223> OTHER INFORMATION: n=A,T,C or G

<400> SEQUENCE: 261

| | | | | | |
|---|---|---|---|---|---|
| tcctgacgat | agccatggct | gtaccactta | actatgattc | tattccaact | gttcagaatc | 60 |
| atatcacaaa | atgacttgta | cacagtagtt | tacaacgact | cccaagagag | gaaaaaaaaa | 120 |
| aaaaaagacg | cctcaaaatt | cactcaactt | ttgagacagc | aatggcaata | ggcagcanag | 180 |
| aagctatgct | gcaactgagg | gcacatatca | ttgaagatgt | cacaggagtt | taagagacag | 240 |
| gctggaaaaa | atctcatact | aagcaaacag | tagtatctca | taccaagcaa | aaccaagtag | 300 |
| tatctgctca | gcctgccgct | aacagatctc | acaatcacca | actgtgcttt | aggactgtca | 360 |
| ccaaa | | | | | | 365 |

<210> SEQ ID NO 262
<211> LENGTH: 500
<212> TYPE: DNA
<213> ORGANISM: Homo sapiens

<400> SEQUENCE: 262

| | | | | | |
|---|---|---|---|---|---|
| cctagatgtc | atttgggacc | cttcacaacc | attttgaagc | cctgtttgag | tccctgggat | 60 |
| atgtgagctg | tttctatgca | taatggatat | tcggggttaa | caacagtccc | ctgcttggct | 120 |
| tctattctga | atcctttttct | ttcaccatgg | ggtgcctgaa | gggtggctga | tgcatatggt | 180 |
| acaatggcac | ccagtgtaaa | gcagctacaa | ttaggagtgg | atgtgttctg | tagcatccta | 240 |
| tttaaataag | cctattttat | cctttggccc | gtcaactctg | ttatctgctg | cttgtactgg | 300 |
| tgcctgtact | tttctgactc | tcattgacca | tattccacga | ccatggttgt | catccattac | 360 |
| ttgatcctac | tttacatgtc | tagtctgtgt | ggttggtggt | gaataggctt | cttttttacat | 420 |
| ggtgctgcca | gcccagctaa | ttaatggtgc | acgtggactt | ttagcaagcg | ggctcactgg | 480 |
| aagagactga | acctggcatg | | | | | 500 |

<210> SEQ ID NO 263
<211> LENGTH: 413
<212> TYPE: DNA
<213> ORGANISM: Homo sapiens

<400> SEQUENCE: 263

| | | | | | |
|---|---|---|---|---|---|
| ctcagagagg | ttgaaagatt | tgcctacgaa | agggacagtg | atgaagctaa | gctctagatc | 60 |
| caggatgtct | gacttcaaat | tgaaactccc | aaagtaatga | gtttggaagg | gtggggtgtg | 120 |
| gcctttccag | gatgggggtc | ttttctgctc | ccagcggata | gtgaaacccc | tgtctgcacc | 180 |
| tggttgggcg | tgttgctttc | ccaaaggttt | ttttttttagg | tccgtcgctg | tcttgtggat | 240 |
| taggcattat | tatctttact | ttgtctccaa | ataacctgga | gaatgagag | agtagtgacc | 300 |
| agctcagggc | cacagtgcga | tgaggaccat | cttctcacct | ctctaaatgc | aggaagaaac | 360 |
| gcagagtaac | gtggaagtgg | tccacaccta | ccgccagcac | attgtgaatg | aca | 413 |

<210> SEQ ID NO 264
<211> LENGTH: 524
<212> TYPE: DNA
<213> ORGANISM: Homo sapiens

<400> SEQUENCE: 264

```
tccaatgggg ccctgagagc tgtgacagga actcacactc tggcactggc agcaaaacac      60
cattccaccc cactcatcgt ctgtgcacct atgttcaaac tttctccaca gttccccaat     120
gaagaagact catttcataa gtttgtggct cctgaagaag tcctgccatt cacagaaggg     180
gacattctgg agaaggtcag cgtgcattgc cctgtgtttg actacgttcc cccagagctc     240
attaccctct ttatctccaa cattggtggg aatgcacctt cctacatcta ccgcctgatg     300
agtgaactct accatcctga tgatcatgtt ttatgaccga ccacacgtgt cctaagcaga     360
ttgcttaggc agatacagaa tgaagaggag acttgagtgt tgctgctgaa gcacatcctt     420
gcaatgtggg agtgcacagg agtccaccta aaaaaaaaaa tccttgatac tgttgcctgc     480
cttttttagtc accccgtaac aagggcacac atccaggact gtgt                     524
```

<210> SEQ ID NO 265
<211> LENGTH: 344
<212> TYPE: DNA
<213> ORGANISM: Homo sapiens

<400> SEQUENCE: 265

```
tcctttcttc tacttcagga gatgattcaa agttacttgt ggacatttct ttaagttctg      60
aagacaaatg agacaggatt tggcctgcgg gttcttcaga cttctctacc acctccatta     120
actcttcatc ttggcttgac gtaggcaatg cactattttg ctcttttgtt tctggagatg     180
acccagcacc acttctttct cttggcgggg ttctaagtgt gtctttgaat accagtgaag     240
actcaggcct atcctgtact ggaaagggac taaatttgtc tttctgtcta ggaggtgatg     300
cagtagcatc ctcctgaggg ggtaaggcca ttttctcttt ttga                      344
```

<210> SEQ ID NO 266
<211> LENGTH: 210
<212> TYPE: DNA
<213> ORGANISM: Homo sapiens
<220> FEATURE:
<221> NAME/KEY: misc_feature
<222> LOCATION: (78)
<223> OTHER INFORMATION: n=A,T,C or G

<400> SEQUENCE: 266

```
ccacaatgtc cataacttga gcaggctttg gcatcccacc accccttca gaccaataca      60
cactatgttg gaggaacnac tttaaaatgt aaaatgagaa atgggcactg aacactccat     120
cctcactccc aacagcccac ccacacacct cttcaactgc tatccaaaca tggaggagct     180
cttgtggaag agaggctcaa caccaaataa                                      210
```

<210> SEQ ID NO 267
<211> LENGTH: 238
<212> TYPE: DNA
<213> ORGANISM: Homo sapiens
<220> FEATURE:
<221> NAME/KEY: misc_feature
<222> LOCATION: (1)...(238)
<223> OTHER INFORMATION: n=A,T,C or G

<400> SEQUENCE: 267

```
tcggncctcc caccctctna ctgaaattct ntgaaattct cccctttggg atgaggatgg      60
caacccagg catgtaccct cccaacctgg gaccgacct aatacccta catcctgctg       120
acagtggctg ttctcgctgg gcaggcgtcc caaagcacat cgagccagat tcaggcagag     180
tggaactggc ccctcagcca tcagtggagg tggcctggga ggctctaccc tgaacggg      238
```

<210> SEQ ID NO 268
<211> LENGTH: 461
<212> TYPE: DNA
<213> ORGANISM: Homo sapiens
<220> FEATURE:
<221> NAME/KEY: misc_feature
<222> LOCATION: (459)
<223> OTHER INFORMATION: n=A,T,C or G

<400> SEQUENCE: 268

```
tcctcaagga catgcccctt gatagaaact cagttcctgt ctccagttcc ctcctggacc      60
tgatccccca aatgcagggc ctgggactat atccagttcc ttattttcag aggcccatgc     120
acaagatgca cagcaaataa gtgctgaata agacccagc tactgctagc ttaccctgct      180
ccaaacattc accaagtcct cagcaaagag ggccatccat tcacctcttc taaaaacaca     240
ctgagctccc cagtctatac cccaagatat gcttggctcc caactatccc tcctctctca     300
tctccaagcc agtttcccct ttctaagtat actgatatta ccaaagacac tgacaatctt     360
cttttcctac ctctccccag tgactaggtt tgcagcagga gctctataag tcctagtata     420
cagcagaagc tccataaatg tgtgctgacc taacattang c                          461
```

<210> SEQ ID NO 269
<211> LENGTH: 434
<212> TYPE: DNA
<213> ORGANISM: Homo sapiens

<400> SEQUENCE: 269

```
ctgtgttggt gagcaccgat tcccactcaa tatggcgtgg cttacagtct tcattaggtt      60
cccgctccca accagaatga ggaatgatca cttcatctgt caaggcatgc agtgcatggt     120
ccacaatctc cattttgatt gagtcatggg atgaaagatt ccacagggtt ccggtaataa     180
cttcagtaag gtccatatca cgagcctttc gaagcaatcg cacaagggca ggcacaccat     240
cacagttttt tatggcaatc ttgttatcct ggtcacgtcc aaaagagata ttcttgagag     300
ctccacaggc tccaaggtgc acttcctttt tgggatggtc taacaatccc accagtactg     360
ggatgccctt gagcttccgc acgtcagtct tcaccttgtc attgcggtag cataagtgtt     420
gcaggtatgc aaga                                                        434
```

<210> SEQ ID NO 270
<211> LENGTH: 156
<212> TYPE: DNA
<213> ORGANISM: Homo sapiens

<400> SEQUENCE: 270

```
ctgcaccagc gattaccagt ggcattcaaa tactgtgtga ctaaggattt tgtatgctcc      60
ccagtagaac cagaatcaga caggtatgag ctagtcaaca gcaagtcttt gttggattcg     120
agtaggctca ggatctgctg aaggtcggag gagtta                                156
```

<210> SEQ ID NO 271
<211> LENGTH: 533
<212> TYPE: DNA
<213> ORGANISM: Homo sapiens
<220> FEATURE:
<221> NAME/KEY: misc_feature
<222> LOCATION: (1)...(533)
<223> OTHER INFORMATION: n=A,T,C or G

<400> SEQUENCE: 271

-continued

```
ccactgtcac ggtctgtctg acacttactg ccaaacgcat ggcaaggaaa aactgcttag      60
tgaagaactt agaagctgtg gagaccttgg ggtccacgtn caccatctgc tctgataaaa     120
ctggaactct gactcanaac cggatgacag tgcccacat gtggtttgac aatcaaatcc      180
atgaagctga tacgacagag aatcagagtg gtgtctcttt tgacaagact tcagctacct    240
ggcttgctct gtccagaatt gcaggtcttt gtaacagggc agtgtttcag gctaaccagg    300
aaaacctacc tattcttaag cgggcagttg caggagatgc ctctgagtca gcactcttaa    360
agtgcataga gctgtgctgt ggntncgtga aggagatgag agaaagatac nccaaaatcg    420
tcgagatacc cttcaactcc accaacaagt accagttgtc tattcataag aaccccaaca    480
catcggagcc ccaacacctg ttggtgatga agggcgcccc agaaaggatc cta           533
```

<210> SEQ ID NO 272
<211> LENGTH: 630
<212> TYPE: DNA
<213> ORGANISM: Homo sapiens

<400> SEQUENCE: 272

```
tggtattttt cttttctttt tggatgtttt atactttttt ttcttttttc ttctctattc     60
ttttcttcgc cttcccgtac ttctgtcttc cagttttcca cttcaaactt ctatcttctc    120
caaattgttt catcctacca ctcccaatta atctttccat tttcgtctgc gtttagtaaa    180
tgcgttaact aggctttaaa tgacgcaatt ctccctgcgt catggatttc aaggtctttt    240
aatcaccttc ggtttaatct cttttaaaa gatcgccttc aaattatttt aatcacctac    300 aactttaaa ctaaacttta agctgtttaa gtcaccttca ttttaatcta aaagcattgc    360
ccttctattg gtattaattc ggggctctgt agtcctttct ctcaattttc ttttaaatac    420
attttttact ccatgaagaa gcttcatctc aacctccgtc atgttttaga aaccttttat   480
cttttccttc ctcatgctac tcttctaagt cttcatattt tctcttaaaa tcttaagcta   540
ttaaaattac gttaaaaact taacgctaag caatatctta gtaacctatt gactatattt   600
tttaagtagt tgtattaatc tctatctttc                                     630
```

<210> SEQ ID NO 273
<211> LENGTH: 400
<212> TYPE: DNA
<213> ORGANISM: Homo sapiens

<400> SEQUENCE: 273

```
tctggtttgc cctccagttc attctgaatc tagacttgct cagcctaatc aagttcctgt     60
acaaccagaa gcgacacagg ttcctttggt atcatccaca agtgaggggt acacagcatc    120
tcaacccttg taccagcctt ctcatgctac agagcaacga ccacagaagg aaccaattga    180
tcagattcag gcaacaatct ctttaaatac agaccagact acagcatcat catcccttcc    240
tgctgcgtct cagcctcaag tatttcaggc tgggacaagc aaacctttac atagcagtgg    300
aatcaatgta aatgcagctc cattccaatc catgcaaacg tgttcaata tgaatgcccc     360 agttcctcct gttaatgaac cagaaacttt aaaacagcaa                          400
```

<210> SEQ ID NO 274
<211> LENGTH: 351
<212> TYPE: DNA
<213> ORGANISM: Homo sapiens
<220> FEATURE:
<221> NAME/KEY: misc_feature
<222> LOCATION: (2)
<223> OTHER INFORMATION: n=A,T,C or G

```
<400> SEQUENCE: 274
tntgagtatg tcccagagaa ggtgaagaaa gcggaaaaga aattagaaga gaatccatat      60
gaccttgatg cttggagcat tctcattcga gaggcacaga atcaacctat agacaaagca     120
cggaagactt atgaacgcct tgttgcccag ttccccagtt ctggcagatt ctggaaactg     180
tacattgaag cagaggttac tattttattt tattttttct tatatcagta ttgcagcatt     240
cactgtagtg atagaaaaca agttaggaac atagccaatt aggacaagga ggatttaaat     300
gtgtcttacc tttattttgt aaaataggta taaaggagta attaaaatga a              351

<210> SEQ ID NO 275
<211> LENGTH: 381
<212> TYPE: DNA
<213> ORGANISM: Homo sapiens
<220> FEATURE:
<221> NAME/KEY: misc_feature
<222> LOCATION: (1)...(381)
<223> OTHER INFORMATION: n=A,T,C or G

<400> SEQUENCE: 275
gcgnggtcgc nnncgaggtc tgagaagccc ataccactat ttgttgagaa atgtgtggaa      60
tttattgaag atacagggtt atgtaccgaa ggactctacc gtgtcagcgg gaataaaact     120
gaccaagaca atattcaaaa gcagtttgat caagatcata atatcaatct agtgtcaatg     180
gaagtaacag taaatgctgt agctggagcc cttaaagctt ctttgcaga tctgccagat     240 cctttaattc catattctct tcatccagaa ctattggaag cagcaaaaat cccggataaa     300
acagaacgtc ttcatgcctt gaaagaaatt gttaagaaat tcatcctgt aaactatgat     360 gtattcagat acgtgataac a                                               381

<210> SEQ ID NO 276
<211> LENGTH: 390
<212> TYPE: DNA
<213> ORGANISM: Homo sapiens
<220> FEATURE:
<221> NAME/KEY: misc_feature
<222> LOCATION: (5)
<223> OTHER INFORMATION: n=A,T,C or G

<400> SEQUENCE: 276
gctcngactc cggcgggacc tgctcggagg aatggcgccg ccgggttcaa gcactgtctt      60
cctgttggcc ctgacaatca tagccagcac ctgggctctg acgccactc actacctcac     120 caagcatgac gtggagagac taaaagcctc gctggatcgc cctttcacaa atttggaatc     180
tgccttctac tccatcgtgg gactcagcag ccttggtgct caggtgccag atgcaaagaa     240
agcatgtacc tacatcagat ctaaccttga tcccagcaat gtggattccc tcttctacgc     300
tgcccaggcc agccaggccc tctcaggatg tgagatctct atttcaaatg agaccaaaga     360
tctgcttctg gcagacctcg gccgcgacca                                      390

<210> SEQ ID NO 277
<211> LENGTH: 378
<212> TYPE: DNA
<213> ORGANISM: Homo sapiens

<400> SEQUENCE: 277
tgggaacttc tggggtagga cgttgtctgc tatctccagt tccacagacc caaccagtta      60
cgatggtttt ggaccattta tgccgggatt cgacatcatt ccctataatg atctgcccgc     120
```

```
actggagcgt gctcttcagg atccaaatgt ggctgcgttc atggtagaac caattcaggg      180
tgaagcaggc gttgttgttc cggatccagg ttacctaatg ggagtgcgag agctctgcac      240
caggcaccag gttctcttta ttgctgatga aatacagaca ggattggcca gaactggtag      300
atggctggct gttgattatg aaaatgtcag acctgatata gtcctccttg gaaaggccct      360
ttctgggggc ttataccc                                                    378
```

<210> SEQ ID NO 278
<211> LENGTH: 366
<212> TYPE: DNA
<213> ORGANISM: Homo sapiens

<400> SEQUENCE: 278

```
ggagggcaca ttccttttca cctcagagtc ggtcgggaa ggccacccag ataagatttg       60
tgaccaaacc agtgatgctg tccttgatgc ccaccttcag caggatcctg atgccaaagt      120
agcttgtgaa actgttgcta aaactggaat gatccttctt gctggggaaa ttacatccag      180
agctgctgtt gactaccaga agtggttcg tgaagctgtt aaacacattg gatatgatga      240
ttcttccaaa ggttttgact acaagacttg taacgtgctg gtagccttgg agcaacagtc      300
accagatatt gctcaaggtg ttcatcttga cagaaatgaa gaagacattg gtgctggaga      360
ccaggg                                                                 366
```

<210> SEQ ID NO 279
<211> LENGTH: 435
<212> TYPE: DNA
<213> ORGANISM: Homo sapiens

<400> SEQUENCE: 279

```
cctaagaact gagacttgtg acacaaggcc aacgacctaa gattagccca gggttgtagc       60
tggaagacct acaacccaag gatggaaggc ccctgtcaca agcctacct agatggatag       120 aggacccaag cgaaaaagat atctcaagac taacggccgg aatctggagg cccatgaccc      180
agaacccagg aaggatagaa gcttgaagac ctggggaaat cccaagatga gaaccctaaa      240
ccctacctct tttctattgt ttacacttct tactcttaga tatttccagt tctcctgttt      300
atctttaagc ctgattcttt tgagatgtac ttttgatgt tgccggttac ctttagattg      360
acaagtatta tgcctggcca gtcttgagcc agctttaaat cacagctttt acctatttgt      420
taggctatag tgttt                                                       435
```

<210> SEQ ID NO 280
<211> LENGTH: 435
<212> TYPE: DNA
<213> ORGANISM: Homo sapiens

<400> SEQUENCE: 280

```
tctggatgag ctgctaactg agcacaggat gacctgggac ccagcccagc caccccgaga       60
cctgactgag gccttcctgg caaagaagga aaggccaag gggagccctg agagcagctt      120
caatgatgag aacctgcgca tagtggtggg taacctgttc cttgccggga tggtgaccac      180
ctcgaccacg ctggcctggg gcctcctgct catgatccta cacctggatg tgcagcgtga      240
gcccagacct gtccgggcgg ccgctcgaaa ttccagcaca ctggcggccg ttactagtgg      300
atccgagctc ggtaccaagc ttggcgtaat catggtcata gctgtttcct gtgtgaaatt      360
gttatccgct cacaattcca cacaacatac gagccggaag cataaagtgt aaagcctggg      420
gtgcctaatg agtga                                                       435
```

<210> SEQ ID NO 281
<211> LENGTH: 440
<212> TYPE: DNA
<213> ORGANISM: Homo sapiens

<400> SEQUENCE: 281

```
catctgatct ataaatgcgg tggcatcgac aaaagaacca ttgaaaaatt tgagaaggag      60
gctgctgaga tgggaaaggg ctccttcaag tatgcctggg tcttggataa actgaaagct     120
gagcgtgaac gtggtatcac cattgatatc tccttgtgga aatttgagac cagcaagtac     180
tatgtgacta tcattgatgc cccaggacac agagacttta tcaaaaacat gattacaggg     240
acatctcagg ctgactgtgc tgtcctgatt gttgctgctg tgttggtga atttgaagct      300
ggtatctcca agaatgggca gacccgagag catgcccttc tggcttacac actgggtgtg     360
aaacaactaa ttgtcggtgt taacaaaatg gattccactg agccccctac agccagaaga     420
gatatgagga aattgttaag                                                  440
```

<210> SEQ ID NO 282
<211> LENGTH: 502
<212> TYPE: DNA
<213> ORGANISM: Homo sapiens

<400> SEQUENCE: 282

```
tctgtggcgc aggagccccc tcccccggca gctctgacgt ctccaccgca gggactggtg      60
cttctcggag ctcccactcc tcagactccg gtggaagtga cgtggacctg gatcccactg     120
atggcaagct cttccccagc gatggttttc gtgactgcaa gaaggggat cccaagcacg      180
ggaagcggaa acgaggccgg ccccgaaagc tgagcaaaga gtactgggac tgtctcgagg     240
gcaagaagag caagcacgcg cccagaggca cccacctgtg ggagttcatc cgggacatcc     300
tcatccaccc ggagctcaac gagggcctca tgaagtggga gaatcggcat gaaggcgtct     360
tcaagttcct gcgctccgag gctgtggccc aactatgggg ccaaaagaaa agaacagca      420
acatgaccta cgagaagctg agccgggcca tgaggtacta ctacaaacgg agatcctgg     480
aacgggtgga tggccggcga ct                                              502
```

<210> SEQ ID NO 283
<211> LENGTH: 433
<212> TYPE: DNA
<213> ORGANISM: Homo sapiens
<220> FEATURE:
<221> NAME/KEY: misc_feature
<222> LOCATION: (1)...(433)
<223> OTHER INFORMATION: n=A,T,C or G

<400> SEQUENCE: 283

```
ccatattaga ttactggaac atctaagcat cagtgtgtga ccatgcgaac aaaagacttc      60
ggggagtgtc tatttttaaa aaggtttatg tgtgtcgagg cagttgtaaa agatttactg     120
cagaatcaan cccacttta ggcttangac caggttctaa ctatctaaaa atattgactg      180
ataacaaaaa gtgttctaaa tgtggctatt ctgatccata nttgnttttt aaagaaaaaa     240
antgtntata cagaaagagt ntaaaagttc tgtgaattna atgcaaatta gncnccantc     300
ttgacttccc aaanacttga ttnatacctt tnactcctnt cnnttcctgn ncttcnttaa     360
nntcaatnat tnggnagtnn anggccntcn gnanaacacc nttncncgnt ccncgcaatc     420
canccgcctt nan                                                        433
```

<210> SEQ ID NO 284
<211> LENGTH: 479
<212> TYPE: DNA
<213> ORGANISM: Homo sapiens

<400> SEQUENCE: 284

| | | | | | |
|---|---|---|---|---|---|
| tctggaagga | tcagggatct | gagcaaagcc | aagtttactt | aagctaagcc | acttgttcct | 60 |
| gggtcaagca | gtttgttttc | taataagcat | cattcctgat | cattagagca | aagggatgaa | 120 |
| tgctcctctt | ggaatgatac | agggatctg | ccactgggag | agtgttgctc | agtgttagag | 180 |
| tagcagcaat | gacagaatga | cagcgactct | ctgagtcaac | ccagtacttt | tagtaccccg | 240 |
| tcactatgtg | aataaaggca | gctagaaaat | ggactcaatt | ctgcaagcct | tcatggcaac | 300 |
| agcccatatt | aagacttcta | gaacaagtta | aaaaaaaatc | ttccatttcc | atccatgcat | 360 |
| gggaaaaggg | ctttagtata | gtttaggatg | gatgtgtgta | taataataaa | atgataagat | 420 |
| atgcatagtg | ggggaataaa | gcctcagagt | ccttccagta | tggggaatcc | attgtatct | 479 |

<210> SEQ ID NO 285
<211> LENGTH: 435
<212> TYPE: DNA
<213> ORGANISM: Homo sapiens
<220> FEATURE:
<221> NAME/KEY: misc_feature
<222> LOCATION: (1)...(435)
<223> OTHER INFORMATION: n=A,T,C or G

<400> SEQUENCE: 285

| | | | | | |
|---|---|---|---|---|---|
| tttttttttt | tttttttttt | tcaatanaaa | tgccataatt | tattccattg | tataaaaaag | 60 |
| tcatccttat | gtaacaaaat | gtnttcttan | aanaanaaat | atattatttc | aggtcataaa | 120 |
| taatcagcaa | acatacaact | gttggcaact | aaaaaaaaac | ccaacactgg | tattttccat | 180 |
| cagngctgaa | aacaaacctg | cttaaaanata | tatttacagg | gatagtncag | tnctcaaaaa | 240 |
| caaaaattga | ggtattttgg | ttcttctagg | agtagacaat | gacattttgg | gangggcaga | 300 |
| cccctnnccc | aaaaaataaa | ataagggnat | nttcttcant | atngaanann | ggggcgccc | 360 |
| cggggaaaan | naaaccttgg | gnnggggggtt | tggcccaagc | ccttgaaaaa | aaantttntt | 420 |
| tcccaaaaaa | aacng | | | | | 435 |

<210> SEQ ID NO 286
<211> LENGTH: 301
<212> TYPE: DNA
<213> ORGANISM: Homo sapiens

<400> SEQUENCE: 286

| | | | | | |
|---|---|---|---|---|---|
| cctggtttct | ggtggcctct | atgaatccca | tgtagggtgc | agaccgtact | ccatccctcc | 60 |
| ctgtgagcac | cacgtcaacg | gctcccggcc | cccatgcacg | ggggagggag | ataccccaa | 120 |
| gtgtagcaag | atctgtgagc | ctggctacag | cccgacctac | aaacaggaca | agcactacgg | 180 |
| atacaattcc | tacagcgtct | ccaatagcga | gaaggacatc | atggccgaga | tctacaaaaa | 240 |
| cggccccgtg | gagggagctt | tctctgtgta | ttcggacttc | ctgctctaca | agtcaggagt | 300 |
| g | | | | | | 301 |

<210> SEQ ID NO 287
<211> LENGTH: 432
<212> TYPE: DNA
<213> ORGANISM: Homo sapiens

<400> SEQUENCE: 287

```
tccagcttgt tgccagcatg agaaccgcca ttgatgacat tgaacgccgg gactggcagg      60
atgacttcag agttgccagc caagtcagcg atgtggcggt acaggggac ccccttctca       120 acggcaccag ctttgcagac ggcaagggac accccagaa tggcgttcgc accaaactta      180
gatttatttt ctgttccatc catctcgatc atcagtttgt caatcttctc ttgttctgtg     240
acgttcagtt tcttgctaac cagggcaggc gcaatagttt tattgatgtg ctcaacagcc     300
tttgagacac ccttccccat atagcgagtc ttatcattgt cccggagctc tagggcctca     360
tagataccag ttgaagcacc actgggcaca gcagctctga agagaccttt tgaggtgaag     420
agatcaacct ca                                                         432
```

<210> SEQ ID NO 288
<211> LENGTH: 326
<212> TYPE: DNA
<213> ORGANISM: Homo sapiens
<220> FEATURE:
<221> NAME/KEY: misc_feature
<222> LOCATION: (254)
<223> OTHER INFORMATION: n=A,T,C or G

<400> SEQUENCE: 288

```
tctggctcaa gtcaaagtcc tggtcctctt ctccgcctcc ttcttcatca tagtaataaa      60
cgttgtcccg ggtgtcatcc tctggggca gtaagggctc tttgaccacc gctctcctcc     120
gaagaaacag caagagcagc agaatcagaa ttagcaaagc aagaattcct ccaagaatcc    180
ccagaatggc aggaatttgc aatcctgctt cgacaggctg tgccttccta cagacgccgg    240
cggccccttc acantcacac acgctgacct ctaaggtggt cacttggtct ttattctggt    300
tatccatgag cttgagattg attttg                                         326
```

<210> SEQ ID NO 289
<211> LENGTH: 451
<212> TYPE: DNA
<213> ORGANISM: Homo sapiens

<400> SEQUENCE: 289

```
gtcccggtgt ggctgtgccg ttggtcctgt gcggtcactt agccaagatg cctgaggaaa      60
cccagaccca agaccaaccg atggaggagg aggaggttga gacgttcgcc tttcaggcag     120
aaattgccca gttgatgtca ttgatcatca atactttcta ctcgaacaaa gagatctttc    180
tgagagagct catttcaaat tcatcagatg cattggacaa aatccggtat gaaagcttga    240
cagatcccag taaattagac tctgggaaag agctgcatat taaccttata ccgaacaaac    300
aagatcgaac tctcactatt gtggatactg gaattggaat gaccaaggct gacttgatca    360
ataaccttgg tactatcgcc aagtctggga ccaaagcgtt catggaagct tgcaggctg     420 gtgcagatat ctctatgatt ggacctcggc c                                    451
```

<210> SEQ ID NO 290
<211> LENGTH: 494
<212> TYPE: DNA
<213> ORGANISM: Homo sapiens
<220> FEATURE:
<221> NAME/KEY: misc_feature
<222> LOCATION: (421)
<223> OTHER INFORMATION: n=A,T,C or G

<400> SEQUENCE: 290

```
tttttttttt tcaaaacagt atattttatt ttacaatagc aaccaactcc ccagtttgtt      60
```

| | |
|---|---|
| tcaattgtga catctagatg gcttaagatt actttctggt ggtcacccat gctgaacaat | 120 |
| attttccaat cttccaaaca gcaaagactc aaaagagatt ctgcatttca catcagttca | 180 |
| caagttcaag agtcttccat ttatcttagc ttttggaata aattatcttt gaggtagaag | 240 |
| gacaatgacg aagccactta attccttgtg tctgcataaa agcagattta ttcatcacaa | 300 |
| cttcatttat gtgaataaag cagatgatga taaaatgttc tcttattctt gtttaatcag | 360 |
| tagtggtagt gatgccagaa acttgtaaat gcacttcaaa ccaattgtgg ctcaagtgta | 420 |
| ngtggttccc caaggctggt accaatgaga ctggggtttg ggaattagtt ggtcatcatc | 480 |
| cctcctgctg ccca | 494 |

<210> SEQ ID NO 291
<211> LENGTH: 535
<212> TYPE: DNA
<213> ORGANISM: Homo sapiens

<400> SEQUENCE: 291

| | |
|---|---|
| tcgcgtgctt aacatgaaaa caaactttgt gctgtttggt tcattgtatg cattgatgga | 60 |
| gtcttgtctc tcatcatggg gtgtctgacc atccaacctg cagtactcat aatttctcca | 120 |
| catgcaataa tcttccaaaa tgtccaatac ccttgtcatt tgactgaaga ttagtactcg | 180 |
| tgaaccttgt tcttttaact tagggagcag cttgtctaaa accaccattt tgccactgtt | 240 |
| ggttactaga tgcatatctg ttgtataagg tggaccaggt tctgctccat caaagagata | 300 |
| tggatgatta caacattttc tcaactgcat taggatgttc ataaccttca ttttgtccat | 360 |
| cttgcctgct gagttgagta tatctatatc cttcattaat atccgagtat accattccct | 420 |
| ttgcattttg ctgaggccca catagatttt tacttccttc tttggaggca aactcttttc | 480 |
| aacatcagcc ttaattcgac gaaggaggaa tggacgcaaa accatatgaa gcctc | 535 |

<210> SEQ ID NO 292
<211> LENGTH: 376
<212> TYPE: DNA
<213> ORGANISM: Homo sapiens
<220> FEATURE:
<221> NAME/KEY: misc_feature
<222> LOCATION: (1)...(376)
<223> OTHER INFORMATION: n=A,T,C or G

<400> SEQUENCE: 292

| | |
|---|---|
| tacnagcccg tgctgatcga gatcctggtg gaggtgatgg atccttcctt cgtgtgcttg | 60 |
| aaaattggag cctgcccctc ggcccataag cccttgttgg gaactgagaa gtgtatatgg | 120 |
| ggcccaagct actggtgcca gaacacagag acagcagccc agtgcaatgc tgtcgagcat | 180 |
| tgcaaacgcc atgtgtggaa ctaggaggag gaatattcca tcttggcaga aaccacagca | 240 |
| ttggtttttt tctacttgtg tgtctggggg aatgaacgca cagatctgtt tgactttgtt | 300 |
| ataaaaatag ggctccccca cctcccccat ttttgtgtcc tttattgnag cattgctgtc | 360 |
| tgcaagggag cccta | 376 |

<210> SEQ ID NO 293
<211> LENGTH: 320
<212> TYPE: DNA
<213> ORGANISM: Homo sapiens

<400> SEQUENCE: 293

| | |
|---|---|
| tcggctgctt cctggtctgg cggggatggg tttgctttgg aaatcctcta ggaggctcct | 60 |
| cctcgcatgg cctgcagtct ggcagcagcc ccgagttgtt cctcgctga tcgatttctt | 120 |

```
tcctccaggt agagttttct tgcttatgt tgaattccat tgcctctttt ctcatcacag      180
aagtgatgtt ggaatcgttt cttttgtttg tctgatttat ggttttttta agtataaaca      240 aaagttttt attagcattc tgaaagaagg aaagtaaaat gtacaagttt aataaaaagg       300
ggccttcccc tttagaatag                                                  320
```

<210> SEQ ID NO 294
<211> LENGTH: 359
<212> TYPE: DNA
<213> ORGANISM: Homo sapiens

<400> SEQUENCE: 294

```
ctgtcataaa ctggtctgga gtttctgacg actccttgtt caccaaatgc accatttcct      60
gagacttgct ggcctctccg ttgagtccac ttggctttct gtcctccaca gctccattgc      120
cactgttgat cactagcttt ttcttctgcc cacaccttct tcgactgttg actgcaatgc      180
aaactgcaag aatcaaagcc aaggccaaga gggatgccaa gatgatcagc cattctggaa      240
tttggggtgt cctatagga ccagaggttg tgtttgctcc accttcttga ctcccatgtg       300
agtgtccatc tgattcagat ccatgagtgg tatgggaccc cccactgggg tggaatgtg       359
```

<210> SEQ ID NO 295
<211> LENGTH: 584
<212> TYPE: DNA
<213> ORGANISM: Homo sapiens
<220> FEATURE:
<221> NAME/KEY: misc_feature
<222> LOCATION: (558)
<223> OTHER INFORMATION: n=A,T,C or G

<400> SEQUENCE: 295

```
cctgagttgg gctgactgcc agagacagac ccctctgggt ctcggtgaac cagccaggca      60
tttacctcag tggttggcac ctggaacctg tccagggccc tcacctgact gaggagccgc      120
cgggcagtga agtaattgtc caggtctatg ctcttgggt ggataccata gccatccaag       180
gtattcctca ggttgtggaa ctgggtctga gtataggcag aactgggccc caggatgatc      240
tcccggagtg ggggaagctg tgaggtcagg taagtatcca cgtccacccg taccccaatc      300
aaactcagca gaatggtgaa ctggagaagt ccttccgtta agtatttctt cagagaaagc      360
attgctgaag gaccagaatg tttatgcttt ttggtttta aaatcttcca aaagacaaat       420
caaggccact gctctgccgc tccagccagc aggttaccct cctcagtgtc aaacccgta      480 ccccaccctg gcagaacaca agggatgagc tccctgacgg ccccagagga agcacaccc      540 tgtggagcca aggccaanga cacactccag accacattca cttt                      584
```

<210> SEQ ID NO 296
<211> LENGTH: 287
<212> TYPE: DNA
<213> ORGANISM: Homo sapiens

<400> SEQUENCE: 296

```
ccttatcatt cattcttagc tcttaattgt tcattttgag ctgaaatgct gcattttaat      60
tttaaccaaa acatgtctcc tatcctggtt tttgtagcct tcctccacat cctttctaaa      120
caagatttta aagacatgta ggtgtttgtt catctgtaac tctaaaagat ccttttta aa    180 ttcagtccta agaagagga gtgcttgtcc cctaagagtg tttaatggca aggcagccct      240
gtctgaagga cacttcctgc ctaagggaga gtggtatttg cagacta                   287
```

<210> SEQ ID NO 297
<211> LENGTH: 457
<212> TYPE: DNA
<213> ORGANISM: Homo sapiens

<400> SEQUENCE: 297

```
ccaattgaaa caaacagttc tgagaccgtt cttccaccac tgattaagag tggggtggca      60
ggtattaggg ataatattca tttagccttc tgagctttct gggcagactt ggtgaccttg     120
ccagctccag cagccttctt gtccactgct ttgatgacac ccaccgcaac tgtctgtctc     180
atatcacgaa cagcaaagcg acccaaaggt ggatagtctg agaagctctc aacacacatg     240
ggcttgccag gaaccatatc aacaatggca gcatcaccag acttcaagaa tttagggcca     300
tcttccagct ttttaccaga acggcgatca atctttcct tcagctcagc aaacttgcat     360
gcaatgtgag ccgtgtggca atccaataca ggggcatagc cggcgcttat ttggcctgga     420
tggttcagga taatcacctg agcagtgaag ccagacc                              457
```

<210> SEQ ID NO 298
<211> LENGTH: 469
<212> TYPE: DNA
<213> ORGANISM: Homo sapiens

<400> SEQUENCE: 298

```
tctttgactt tccttgtcta cctcctctgg agatctcaaa ttctccaggt tccatgctcc      60
cagagatctc aatgattcct gattctcctc ttccaggagt ctgaatgtct cttggttcac     120
ttccacagac tccagtggtt cttgaatttc cttttctaga ggattcattg cccctgatt      180
tatttcttct ggagtccaca gtggtgcttg agttctggaa gatttcagtg tttccaggtt     240
ctcttgtccc gcagacttca gtgattctag gatctctgtt tctaaagatt ttactgcctc     300
tatgctctct tctttgagtg actttaagaa ctcttgattc tcattttcaa gaggtctagc     360
tatctcctgg tcaagagact tcagtggttc tagatccact ttttctgggg gtcttaatgt     420
catctgatcc tgttccccta gagacctccg tcgctgttga gtctcttt                  469
```

<210> SEQ ID NO 299
<211> LENGTH: 165
<212> TYPE: DNA
<213> ORGANISM: Homo sapiens
<220> FEATURE:
<221> NAME/KEY: misc_feature
<222> LOCATION: (1)...(165)
<223> OTHER INFORMATION: n=A,T,C or G

<400> SEQUENCE: 299

```
tctgtggaga ggatgaggtt gagggaggtg gggtatntcg ctgctctgac cttaggtaga      60
gtcctccaca gaagcatcaa antggactgg cacatatgga ctcccttcac aggccacaat     120
gatgtgtctc tccttcgggc tggnccggta tgcacagttg gggta                     165
```

<210> SEQ ID NO 300
<211> LENGTH: 506
<212> TYPE: DNA
<213> ORGANISM: Homo sapiens

<400> SEQUENCE: 300

```
tctgaggaaa gtttgggctt attagtattt gctccagcga acctccaagt tttctccatt      60
gcggacaacg taactaccag ctccttggct cagtggttcg cctccactca gaagttccca     120
gtaggttctg tcattattgt tggcacatag gccctgaata caggtgatat agggccccca     180
```

```
tgagcgctcc tccattgtga aaccaaatat agtatcattc attttctggg ctttctccat    240
cacactgagg aagacagaac catttagcac agtgacattg gtgaaatatg tttcattgat    300
tctcacagag taattgacgg agatatatga ttgtgagtca ggaggtgtca cagttatagg    360
ctcatcagcg gagatgttga agttacctga agcagagacg caagaagagt ctttgttaat    420
atccaagaag gtctttccca tcagggcagg taagacctgg gctgcagcgt ttggattgct    480
gaatgctcct tgagaaattt ccgtga                                         506
```

<210> SEQ ID NO 301
<211> LENGTH: 304
<212> TYPE: DNA
<213> ORGANISM: Homo sapiens
<220> FEATURE:
<221> NAME/KEY: misc_feature
<222> LOCATION: (1)...(304)
<223> OTHER INFORMATION: n=A,T,C or G

<400> SEQUENCE: 301

```
tcctaaggca gagcccccat cacctcaggc ttctcagttc ccttagccgt cttactcaac     60 tgccccttc ctctccctca gaatttgtgt ttgctgcctc tatcttgttt tttgtttttt    120
cttctggggg gggtctagaa cagtgcctgg cacatagtag gcgctcaata aatacttgtt    180
tgttgaatgt ctcctctctc tttccactct gggaaaccta ngnttctgcc attctgggtg    240
accctgtatt tntttctggt gcccattcca tttgnccagn taatacttcc tcttaaaaat    300
ctcc                                                                 304
```

<210> SEQ ID NO 302
<211> LENGTH: 492
<212> TYPE: DNA
<213> ORGANISM: Homo sapiens

<400> SEQUENCE: 302

```
ttttcagtaa gcaacttttc catgctctta atgtattcct ttttagtagg aatccggaag     60
tattagattg aatggaaaag cacttgccat ctctgtctag gggtcacaaa ttgaaatggc    120
tcctgtatca catacggagg tcttgtgtat ctgtggcaac agggagtttc cttattcact    180
ctttatttgc tgctgtttaa gttgccaacc tcccctccca ataaaaattc acttacacct    240
cctgcctttg tagttctggt attcacttta ctatgtgata gaagtagcat gttgctgcca    300
gaatacaagc attgcttttg gcaaattaaa gtgcatgtca tttcttaata cactagaaag    360
gggaaataaa ttaaagtaca caagtccaag tctaaaactt tagtactttt ccatgcagat    420
ttgtgcacat gtgagagggt gtccagtttg tctagtgatt gttatttaga gagttggacc    480
actattgtgt gt                                                        492
```

<210> SEQ ID NO 303
<211> LENGTH: 470
<212> TYPE: DNA
<213> ORGANISM: Homo sapiens

<400> SEQUENCE: 303

```
tctggggcag caggtactcc ctacggcact agtctacagg gggaaggacg ctctgtgctg     60
gcagcggtgg ctcacatggc ctgtctgcac tgtaaccaca ggctgggatg tagccaggac    120
ttggtctcct tggaagacag gtctgatgtt tggccaatcc agtccttcag accctgcctg    180
aaacttgtat cttacgtgaa cttaaagaat aaaatgcatt tctaccccga tctcgccccc    240
```

| | |
|---|---|
| aggactggca cgacaggccc acggcagatt agatctttc ccagtactga tcggtgcgtg | 300 |
| gaattccagc caccacttct gattcgattc cacagtgatc ctgtcctctg agtatttaa | 360 |
| agaagccatt gtcaccccag tcagtgttcc aggagttggc aaccagccag tagggtgtgc | 420 |
| cattctccac tccccagccc aggatgcgga tggcatggac ctcggccgcg | 470 |

<210> SEQ ID NO 304
<211> LENGTH: 79
<212> TYPE: DNA
<213> ORGANISM: Homo sapiens

<400> SEQUENCE: 304

| | |
|---|---|
| tgtcccattg ttaactcagc ctcaaatctc aactgtcagg ccctacaaag aaaatggaga | 60 |
| gcctcttctg gtggatgcg | 79 |

<210> SEQ ID NO 305
<211> LENGTH: 476
<212> TYPE: DNA
<213> ORGANISM: Homo sapiens

<400> SEQUENCE: 305

| | |
|---|---|
| tcactgagcc accctacagc cagaagagat atgaggaaat tgttaaggaa gtcagcactt | 60 |
| acattaagaa aattggctac aacccgaca cagtagcatt tgtgccaatt tctggttgga | 120 |
| atggtgacaa catgctggag ccaagtgcta acgtaagtgg ctttcaagac cattgttaaa | 180 |
| aagctctggg aatggcgatt tcatgcttac acaaattggc atgcttgtgt ttcagatgcc | 240 |
| ttggttcaag ggatggaaag tcacccgtaa ggatggcaat gccagtggaa ccacgctgct | 300 |
| tgaggctctg gactgcatcc taccaccaac tcgtccaact gacaagccct gcgcctgcc | 360 |
| tctccaggat gtctacaaaa ttggtggtaa gttggctgta aacaaagttg aatttgagtt | 420 |
| gatagagtac tgtctgcctt cataggtatt tagtatgctg taaatatttt taggta | 476 |

<210> SEQ ID NO 306
<211> LENGTH: 404
<212> TYPE: DNA
<213> ORGANISM: Homo sapiens

<400> SEQUENCE: 306

| | |
|---|---|
| tctgtctcgg agctcagggc gcagccagca cacacaggag cccacaggac agccacgtct | 60 |
| tcacagaaac tacagaagtc aggacccagg cgaggacctc aggaacaagt gcccctgca | 120 |
| gacagagaga cgcagtagca acagcttctg aacaactaca taataatgcg gggagaatcc | 180 |
| tgaagaccac tgcatcccac aagcactgac aaccacttca ggatttatt tcctccactc | 240 |
| taacccccag atccatttat gagaagtgag tgaggatggc aggggcatgg agggtgaagg | 300 |
| gacagcaagg atggtctgag ggcctggaaa caatagaaaa tcttcgtcct ttagcatatc | 360 |
| ctggactaga aaacaagagt tggagaagag gggggttgat acta | 404 |

<210> SEQ ID NO 307
<211> LENGTH: 260
<212> TYPE: DNA
<213> ORGANISM: Homo sapiens
<220> FEATURE:
<221> NAME/KEY: misc_feature
<222> LOCATION: (1)...(260)
<223> OTHER INFORMATION: n=A,T,C or G

<400> SEQUENCE: 307

| | |
|---|---|
| tcctgcctan acatctgtga gggcctcaag ggctgctgcc tcgactttct ccctagctaa | 60 |

```
gtccacccgt ccagggacac agccagggca ctgctctgtg ctgacttcca ctgcagccaa    120
gggtcaaaat gaagcatctg cggaggccag gactccttgg catcggacac agtcagggga    180
aaagccaccc tgactctgca ggacagaggg tctagggtca tttggcagga gaacactggt    240
gtgccaaggg aagcnancat                                                260

<210> SEQ ID NO 308
<211> LENGTH: 449
<212> TYPE: DNA
<213> ORGANISM: Homo sapiens

<400> SEQUENCE: 308
tctgtgctcc cgactcctcc atctcaggta ccaccgactg cactgggcgg ggccctctgg     60
ggggaaaggc tccacggggc agggatacat ctcgaggcca gtcatcctct ggaggcagcc    120
caatcaggtc aaagattttg cccaactggt cggcttcaga gtttccacag aagagaggct    180
ttcgacgaaa catctctgca agatacagc caacactcca catgtccaca ggtgttgcat     240
atgtggactg cagaagaact tcgggagctc ggtaccagag tgtaacaacc ttgatcgttt    300
cggctggcaa gcctggtggg ggtgccttgt ccagatatgt ccttaggtcc tggtctacat    360
gctcaaacac cagggttacc ttgatctccc ggtcagttcg ggatgtggca cagacgtcca    420
tcagccggac aacattggga tgctcaaaa                                      449

<210> SEQ ID NO 309
<211> LENGTH: 411
<212> TYPE: DNA
<213> ORGANISM: Homo sapiens
<220> FEATURE:
<221> NAME/KEY: misc_feature
<222> LOCATION: (384)
<223> OTHER INFORMATION: n=A,T,C or G

<400> SEQUENCE: 309
ctgtggaaac ctggggtgcc gggtaaatgg agaactccag cttggatttc ttgccataat     60
caactgagag acgttccatg agcagggagg tgaacccaga accagttccc ccaccaaagc    120
tgtggaaaac caagaagccc tgaagaccgg tgcactggtc agccagcttg cgaattcggt    180
ccaacacaag gtcaatgatc tccttgccaa tggtgtagtg ccctcgggca tagttattgg    240
cagcatcttc cttgcctgtg atgagctgct cagggtggaa gagctggcgg taggtgccag    300
tgcgaacttc atcaatgact gtgggttcca agtctacaaa cacagcccgg ggcacgtgct    360
tgccagcgcc cgtctcactt gaanaagggt gtttgaagga agtcatctcc t             411

<210> SEQ ID NO 310
<211> LENGTH: 320
<212> TYPE: DNA
<213> ORGANISM: Homo sapiens
<220> FEATURE:
<221> NAME/KEY: misc_feature
<222> LOCATION: (250)
<223> OTHER INFORMATION: n=A,T,C or G

<400> SEQUENCE: 310
tcctcgtcca gcttgactcg attagtcctc ataaggtaag caaggcagat ggtggctgac     60
cgggaaatgc ctgcctggca gtggacaaac acccttcctc cagcattctt gatggagtct    120
atgaagtcaa tggcctcgtt gaaccaggag ctgatgtctg ccttgtggtt gtcctccaca    180
gggatgctct tgtactggta gtgaccctca aaatggttgg gacaattggc tgagacgttg    240
```

```
atcaaggcan ttatgcccaa ggcatccagc atgtccttgc gggaagcgtg atacgcactg    300
cccaggtaca gaaagggcag                                                320

<210> SEQ ID NO 311
<211> LENGTH: 539
<212> TYPE: DNA
<213> ORGANISM: Homo sapiens

<400> SEQUENCE: 311
tctggcccat gaagctgaag ttgggagaga tgatgcttcg cctctgcttc acaaactcaa     60
aggcctcgtc cagcttgact cgattagtcc tcataaggta agcaaggcag atggtggctg    120
accgggaaat gcctgcctgg cagtggacaa acacccttcc tccagcattc ttgatggagt    180
ctatgaagtc aatggcctcg ttgaaccagg agctgatgtc tgccttgtgg ttgtcctcca    240
cagggatgct cttgtactgg tagtgaccct caaaatggtt gggacaattg gctgagacgt    300
tgatcaaggc agttatgccc aaggcatcca gcatgtcctt gcgggaagcg tgatacgcac    360
tgcccaggta cagaaagggc aggatttcca ccgggccacc ctgaaatcca gaaatatcca    420
acattcatca gcttgctca aagccaaggc cagtgcccat acccacaaaa actttctgct    480
ggaaaagtca atttcagata ccgagtgaac tcagttctgt tgctggagga taaataaat    539

<210> SEQ ID NO 312
<211> LENGTH: 475
<212> TYPE: DNA
<213> ORGANISM: Homo sapiens

<400> SEQUENCE: 312
tcaaggatct tcctaaagcc accatgtgag aggattcgga cgagagtctg agctgtatgg     60
cagaccatgt cctgctgttc tagggtcatg actgtgtgta ctctaaagtt gccactctca    120 cagggtcag tgatacccac tgaacctggc aggaacagtc ctgcagccag aatctgcaag    180
cagcgcctgt atgcaacgtt tagggccaaa ggctgtctgg tggggttgtt catcacagca    240
taatggccta gtaggtcaag gatccagggt gtgaggggct caaagccagg aaaacgaatc    300
ctcaagtcct tcagtagtct gatgagaact ttaactgtgg actgagaagc attttcctcg    360
aaccagcggg catgtcggat ggctgctaag gcactctgca atactttgat atccaaatgg    420
agttctggat ccagttttcg aagattgggt ggcactgttg taatgagaat cttca        475

<210> SEQ ID NO 313
<211> LENGTH: 456
<212> TYPE: DNA
<213> ORGANISM: Homo sapiens

<400> SEQUENCE: 313
tccacttaaa gggtgcctct gccaactggt ggaatcatcg ccacttccag caccacgcca     60
agcctaacat cttccacaag gatcccgatg tgaacatgct gcacgtgttt gttctgggcg    120
aatggcagcc catcgagtac ggcaagaaga agctgaaata cctgccctac aatcaccagc    180
acgaatactt cttcctgatt gggccgccgc tgctcatccc catgtatttc cagtaccaga    240
tcatcatgac catgatcgtc cataagaact gggtggacct ggcctgggcc gtcagctact    300
acatccggtt cttcatcacc tacatccctt tctacggcat cctgggagcc tcccttttcc    360
tcaacttcat caggttcctg gagagccact ggtttgtgtg ggtcacacag atgaatcaca    420
tcgtcatgga gattgaccag gaggacctcg gcccgc                              456
```

-continued

```
<210> SEQ ID NO 314
<211> LENGTH: 477
<212> TYPE: DNA
<213> ORGANISM: Homo sapiens

<400> SEQUENCE: 314
tgcgtgggct tctggaagcc tggatctgga atcattcacc agattattct ggaaaactat      60
gcgtaccctg gtgttcttct gattggcact gactcccaca cccccaatgg tggcggcctt     120
gggggcatct gcattggagt tgggggtgcc gatgctgtgg atgtcatggc tgggatcccc     180
tgggagctga agtgccccaa ggtgattggc gtgaagctga cgggctctct ctccggttgg     240
tcctcaccca aagatgtgat cctgaaggtg gcaggcatcc tcacggtgaa aggtggcaca     300
ggtgcaatcg tggaatacca cgggcctggt gtagactcca tctcctgcac tggcatggcg     360
acaatctgca acatgggtgc agaaattggg gccaccactt ccgtgttccc ttacaaccac     420
aggatgaaga agtatctgag caagaccggc cgggaagaca ttgccaatct agctgat       477

<210> SEQ ID NO 315
<211> LENGTH: 221
<212> TYPE: DNA
<213> ORGANISM: Homo sapiens
<220> FEATURE:
<221> NAME/KEY: misc_feature
<222> LOCATION: (1)...(221)
<223> OTHER INFORMATION: n = A,T,C or G

<400> SEQUENCE: 315
ggtccattcc tttcctcgcg tngggtttc tctgtgtcag cgagcctcgg tacactgatt       60
tccgatcaaa agaatcatca tctttacctt gacttttcag ggaattactg aactttcttc     120
tcagaagata gggcacagcc attgccttgg cctcacttga agggtctgca tttgggtcct     180
ctggtctctt gccaagtttc ccagccactc gagggagaaa t                         221
```

COMPOSITIONS FOR THE TREATMENT AND DIAGNOSIS OF BREAST CANCER AND METHODS FOR THEIR USE

CROSS-REFERENCE TO RELATED APPLICATIONS

This application is a continuation-in-part of U.S. Application No. Ser. 09/285,480, filed on Apr. 2, 1999, which is a continuation-in-part of U.S. application Ser. No. 09/222,575, filed Dec. 28, 1998 now U.S. Pat. No. 6,387,697.

TECHNICAL FIELD

The present invention relates generally to compositions and methods for the treatment of breast cancer. The invention is more particularly related to polypeptides comprising at least a portion of a protein that is p referentially expressed in breast tumor tissue and to polynucleotides encoding such polypeptides. Such polypeptides and polynucleotides may be used in vaccines and pharmaceutical compositions for treatment of breast cancer.

BACKGROUND OF THE INVENTION

Breast cancer is a significant health problem for women in the United States and throughout the world. Although advances have been made in detection and treatment of the disease, breast cancer remains the second leading cause of cancer-related deaths in women, affecting more than 180,000 women in the United States each year. For women in North America, the life-time odds of getting breast cancer are one in eight.

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. See, e.g., Porter-Jordan and Lippman, *Breast Cancer* 8:73–100 (1994). However, the use of established markers often leads to a result that is difficult to interpret, and the high mortality observed in breast cancer patients indicates that improvements are needed in the treatment, diagnosis and prevention of the disease.

Accordingly, there is a need in the art for improved methods for the treatment and diagnosis of breast cancer. The present invention fulfills these needs and further provides other related advantages.

SUMMARY OF THE INVENTION

The present invention provides compounds and methods for the treatment and diagnosis of breast cancer. In one aspect, isolated polypeptides are provided comprising at least an immunogenic portion of a breast tumor antigen or a variant thereof, wherein the antigen comprises an amino acid sequence encoded by a polynucleotide having a sequence selected from the group consisting of: (a) nucleotide sequences recited in SEQ ID NO: 1–61, 63–175, 178, 180 and 182–313; (b) complements of said nucleotide sequences; and (c) sequences that hybridize to a sequence of (a) or (b) under moderately stringent conditions. In specific embodiments, the inventive polypeptides comprise an amino acid sequence selected from the group consisting of SEQ ID NO: 62, 176, 179 and 181.

In related aspects, isolated polynucleotides encoding the above polypeptides are provided. In specific embodiments, such polynucleotides comprise a sequence selected from the group consisting of sequences provided in SEQ ID NO: 1–61, 63–175, 178, 180 and 182–313. The present invention further provides expression vectors comprising the above polynucleotides, together with host cells transformed or transfected with such expression vectors. In preferred embodiments, the host cells are selected from the group consisting of *E. coli*, yeast and mammalian cells.

In another aspect, the present invention provides fusion proteins comprising a first and a second inventive polypeptide or, alternatively, an inventive polypeptide and a known breast tumor antigen.

The present invention also provides pharmaceutical compositions comprising at least one of the above polypeptides, or a polynucleotide encoding such a polypeptide, and a physiologically acceptable carrier, together with vaccines comprising at least one such polypeptide or polynucleotide in combination with a non-specific immune response enhancer. Pharmaceutical compositions and vaccines comprising one or more of the above fusion proteins are also provided.

In yet another aspect, methods are provided for inhibiting the development of breast cancer in a patient, comprising administering an effective amount of at least one of the above pharmaceutical compositions and/or vaccines.

The polypeptides disclosed herein may be usefully employed in the diagnosis and monitoring of breast cancer. In one aspect of the present invention, methods are provided for detecting breast cancer in a patient, comprising: (a) contacting a biological sample obtained from a patient with a binding agent that is capable of binding to one of the above polypeptides; and (b) detecting in the sample a protein or polypeptide that binds to the binding agent. In preferred embodiments, the binding agent is an antibody, most preferably a monoclonal antibody.

In related aspects, methods are provided for monitoring the progression of breast cancer in a patient, comprising: (a) contacting a biological sample obtained from a patient with a binding agent that is capable of binding to one of the above polypeptides; (b) determining in the sample an amount of a protein or polypeptide that binds to the binding agent; (c) repeating steps (a) and (b); and comparing the amounts of polypeptide detected in steps (b) and (c).

Within related aspects, the present invention provides antibodies, preferably monoclonal antibodies, that bind to the inventive polypeptides, as well as diagnostic kits comprising such antibodies, and methods of using such antibodies to inhibit the development of breast cancer.

The present invention further provides methods for detecting breast cancer comprising: (a) obtaining a biological sample from a patient; (b) contacting the sample with a first and a second oligonucleotide primer in a polymerase chain reaction, at least one of the oligonucleotide primers being specific for a polynucleotide that encodes one of the above polypeptides; and (c) detecting in the sample a DNA sequence that amplifies in the presence of the first and second oligonucleotide primers. In a preferred embodiment, at least one of the oligonucleotide primers comprises at least about 10 contiguous nucleotides of a polynucleotide comprising a sequence selected from the group consisting of SEQ ID NO: 1–61, 63–175, 178, 180 and 182–313.

In a further aspect, the present invention provides a method for detecting breast cancer in a patient comprising: (a) obtaining a biological sample from the patient; (b) contacting the sample with an oligonucleotide probe specific for a polynucleotide that encodes one of the above polypeptides; and (c) detecting in the sample a DNA sequence that hybridizes to the oligonucleotide probe. Preferably, the oligonucleotide probe comprises at least about 15 contiguous nucleotides of a polynucleotide comprising a sequence selected from the group consisting of SEQ ID NO: 1–61, 63–175, 178, 180 and 182–313.

In related aspects, diagnostic kits comprising the above oligonucleotide probes or primers are provided.

These and other aspects of the present invention will become apparent upon reference to the following detailed description. All references disclosed herein are hereby incorporated by reference in their entirety as if each was incorporated individually.

BRIEF DESCRIPTION OF THE DRAWING AND SEQUENCE IDENTIFIERS

FIG. 1 shows the results of a Northern blot of the clone SYN18C6 (SEQ ID NO: 40).

SEQ ID NO: 1 is the determined cDNA sequence of JBT2.

SEQ ID NO: 2 is the determined cDNA sequence of JBT6.

SEQ ID NO: 3 is the determined cDNA sequence of JBT7.

SEQ ID NO: 4 is the determined cDNA sequence of JBT10.

SEQ ID NO: 5 is the determined cDNA sequence of JBT13.

SEQ ID NO: 6 is the determined cDNA sequence of JBT14.

SEQ ID NO: 7 is the determined cDNA sequence of JBT15.

SEQ ID NO: 8 is the determined cDNA sequence of JBT16.

SEQ ID NO: 9 is the determined cDNA sequence of JBT17.

SEQ ID NO: 10 is the determined cDNA sequence of JBT22.

SEQ ID NO: 11 is the determined cDNA sequence of JBT25.

SEQ ID NO: 12 is the determined cDNA sequence of JBT28.

SEQ ID NO: 13 is the determined cDNA sequence of JBT32.

SEQ ID NO: 14 is the determined cDNA sequence of JBT33.

SEQ ID NO: 15 is the determined cDNA sequence of JBT34.

SEQ ID NO: 16 is the determined cDNA sequence of JBT36.

SEQ ID NO: 17 is the determined cDNA sequence of JBT37.

SEQ ID NO: 18 is the determined cDNA sequence of JBT51.

SEQ ID NO: 19 is the determined cDNA sequence of JBTT1.

SEQ ID NO: 20 is the determined cDNA sequence of JBTT7.

SEQ ID NO: 21 is the determined cDNA sequence of JBTT11.

SEQ ID NO: 22 is the determined cDNA sequence of JBTT14.

SEQ ID NO: 23 is the determined cDNA sequence of JBTT18.

SEQ ID NO: 24 is the determined cDNA sequence of JBTT19.

SEQ If NO: 25 is the determined cDNA sequence of JBTT20.

SEQ ID NO: 26 is the determined cDNA sequence of JBTT21.

SEQ ID NO: 27 is the determined cDNA sequence of JBTT22.

SEQ ID NO: 28 is the determined cDNA sequence of JBTT28.

SEQ ID NO: 29 is the determined cDNA sequence of JBTT29.

SEQ ID NO: 30 is the determined cDNA sequence of JBTT33.

SEQ ID NO: 31 is the determined cDNA sequence of JBTT37.

SEQ ID NO: 32 is the determined cDNA sequence of JBTT38.

SEQ ID NO: 33 is the determined cDNA sequence of JBTT47.

SEQ ID NO: 34 is the determined cDNA sequence of JBTT48.

SEQ ID NO: 35 is the determined cDNA sequence of JBTT50.

SEQ ID NO: 36 is the determined cDNA sequence of JBTT51.

SEQ ID NO: 37 is the determined cDNA sequence of JBTT52.

SEQ ID NO: 38 is the determined cDNA sequence of JBTT54.

SEQ ID NO: 39 is the determined cDNA sequence of SYN17F4.

SEQ ID NO: 40 is the determined cDNA sequence of SYN18C6.

SEQ ID NO: 41 is the determined cDNA sequence of SYN19A2.

SEQ ID NO: 42 is the determined cDNA sequence of SYN19C8.

SEQ ID NO: 43 is the determined cDNA sequence of SYN20A12.

SEQ ID NO: 44 is the determined cDNA sequence of SYN20G6.

SEQ ID NO: 45 is the determined cDNA sequence of SYN20G6-2.

SEQ ID NO: 46 is the determined cDNA sequence of SYN21B9.

SEQ ID NO: 47 is the determined cDNA sequence of SYN21B9-2.

SEQ ID NO: 48 is the determined cDNA sequence of SYN21C10.

SEQ ID NO: 49 is the determined cDNA sequence of SYN21G10.

SEQ ID NO: 50 is the determined cDNA sequence of SYN21G10-2.

SEQ ID NO: 51 is the determined cDNA sequence of SYN21G11.

SEQ ID NO: 52 is the determined cDNA sequence of SYN21G11-2.

SEQ ID NO: 53 is the determined cDNA sequence of SYN21 H8.

SEQ ID NO: 54 is the determined cDNA sequence of SYN22A10.

SEQ ID NO: 55 is the determined cDNA sequence of SYN22A10-2.

SEQ ID NO: 56 is the determined cDNA sequence of SYN22A12.

SEQ ID NO: 57 is the determined cDNA sequence of SYN22A2.

SEQ ID NO: 58 is the determined cDNA sequence of SYN22B4.

SEQ ID NO: 59 is the determined cDNA sequence of SYN22C2.

SEQ ID NO: 60 is the determined cDNA sequence of SYN22E10.

SEQ ID NO: 61 is the determined cDNA sequence of SYN22F2.

SEQ ID NO: 62 is a predicted amino acid sequence for SYN18C6.

SEQ ID NO: 63 is the determined cDNA sequence of B723P.

SEQ ID NO: 64 is the determined cDNA sequence for B724P.

SEQ ID NO: 65 is the determined cDNA sequence of B770P.

SEQ ID NO: 66 is the determined cDNA sequence of B716P.

SEQ ID NO: 67 is the determined cDNA sequence of B725P.

SEQ ID NO: 68 is the determined cDNA sequence of B717P.

SEQ ID NO: 69 is the determined cDNA sequence of B771P.

SEQ ID NO: 70 is the determined cDNA sequence of B722P.

SEQ ID NO: 71 is the determined cDNA sequence of B726P.

SEQ ID NO: 72 is the determined cDNA sequence of B727P.

SEQ ID NO: 73 is the determined cDNA sequence of B728P.

SEQ ID NO: 74–87 are the determined cDNA sequences of isolated clones which show homology to known sequences.

SEQ ID NO: 88 is the determined cDNA sequence of 13053.

SEQ ID NO: 89 is the determined cDNA sequence of 13057.

SEQ ID NO: 90 is the determined cDNA sequence of 13059.

SEQ ID NO: 91 is the determined cDNA sequence of 13065.

SEQ ID NO: 92 is the determined cDNA sequence of 13067.

SEQ ID NO: 93 is the determined cDNA sequence of 13068.

SEQ ID NO: 94 is the determined cDNA sequence of 13071.

SEQ ID NO: 95 is the determined cDNA sequence of 13072.

SEQ ID NO: 96 is the determined cDNA sequence of 13073.

SEQ ID NO: 97 is the determined cDNA sequence of 13075.

SEQ ID NO: 98 is the determined cDNA sequence of 13078.

SEQ ID NO: 99 is the determined cDNA sequence of 13079.

SEQ ID NO: 100 is the determined cDNA sequence of 13081.

SEQ ID NO: 101 is the determined cDNA sequence of 13082.

SEQ ID NO: 102 is the determined cDNA sequence of 13092.

SEQ ID NO: 103 is the determined cDNA sequence of 13097.

SEQ ID NO: 104 is the determined cDNA sequence of 13101.

SEQ ID NO: 105 is the determined cDNA sequence of 13102.

SEQ ID NO: 106 is the determined cDNA sequence of 13119.

SEQ ID NO: 107 is the determined cDNA sequence of 13131.

SEQ ID NO: 108 is the determined cDNA sequence of 13133.

SEQ ID NO: 109 is the determined cDNA sequence of 13135.

SEQ ID NO: 110 is the determined cDNA sequence of 13139.

SEQ ID NO: 111 is the determined cDNA sequence of 13140.

SEQ ID NO: 112 is the determined cDNA sequence of 13146.

SEQ ID NO: 113 is the determined cDNA sequence of 13147.

SEQ ID NO: 114 is the determined cDNA sequence of 13148.

SEQ ID NO: 115 is the determined cDNA sequence of 13149.

SEQ ID NO: 116 is the determined cDNA sequence of 13151.

SEQ ID NO: 117 is the determined cDNA sequence of 13051

SEQ ID NO: 118 is the determined cDNA sequence of 13052

SEQ ID NO: 119 is the determined cDNA sequence of 13055

SEQ ID NO: 120 is the determined cDNA sequence of 13058

SEQ ID NO: 121 is the determined cDNA sequence of 13062

SEQ ID NO: 122 is the determined cDNA sequence of 13064

SEQ ID NO: 123 is the determined cDNA sequence of 13080

SEQ ID NO: 124 is the determined cDNA sequence of 13093

SEQ ID NO: 125 is the determined cDNA sequence of 13094

SEQ ID NO: 126 is the determined cDNA sequence of 13095

SEQ ID NO: 127 is the determined cDNA sequence of 13096
SEQ ID NO: 128 is the determined cDNA sequence of 13099
SEQ ID NO: 129 is the determined cDNA sequence of 13100
SEQ ID NO: 130 is the determined cDNA sequence of 13103
SEQ ID NO: 131 is the determined cDNA sequence of 13106
SEQ ID NO: 132 is the determined cDNA sequence of 13107
SEQ ID NO: 133 is the determined cDNA sequence of 13108
SEQ ID NO: 134 is the determined cDNA sequence of 13121
SEQ ID NO: 135 is the determined cDNA sequence of 13126
SEQ ID NO: 136 is the determined cDNA sequence of 13129
SEQ ID NO: 137 is the determined cDNA sequence of 13130
SEQ ID NO: 138 is the determined cDNA sequence of 13134
SEQ ID NO: 139 is the determined cDNA sequence of 13141
SEQ ID NO: 140 is the determined cDNA sequence of 13142
SEQ ID NO: 141 is the determined cDNA sequence of 14376
SEQ ID NO: 142 is the determined cDNA sequence of 14377
SEQ ID NO: 143 is the determined cDNA sequence of 14383
SEQ ID NO: 144 is the determined cDNA sequence of 14384
SEQ ID NO: 145 is the determined cDNA sequence of 14387
SEQ ID NO: 146 is the determined cDNA sequence of 14392
SEQ ID NO: 147 is the determined cDNA sequence of 14394
SEQ ID NO: 148 is the determined cDNA sequence of 14398
SEQ ID NO: 149 is the determined cDNA sequence of 14401
SEQ ID NO: 150 is the determined cDNA sequence of 14402
SEQ ID NO: 151 is the determined cDNA sequence of 14405
SEQ ID NO: 152 is the determined cDNA sequence of 14409
SEQ ID NO: 153 is the determined cDNA sequence of 14412
SEQ ID NO: 154 is the determined cDNA sequence of 14414
SEQ ID NO: 155 is the determined cDNA sequence of 14415
SEQ ID NO: 156 is the determined cDNA sequence of 14416
SEQ ID NO: 157 is the determined cDNA sequence of 14419
SEQ ID NO: 158 is the determined cDNA sequence of 14426
SEQ ID NO: 159 is the determined cDNA sequence of 14427
SEQ ID NO: 160 is the determined cDNA sequence of 14375
SEQ ID NO: 161 is the determined cDNA sequence of 14378
SEQ ID NO: 162 is the determined cDNA sequence of 14379
SEQ ID NO: 163 is the determined cDNA sequence of 14380
SEQ ID NO: 164 is the determined cDNA sequence of 14381
SEQ ID NO: 165 is the determined cDNA sequence of 14382
SEQ ID NO: 166 is the determined cDNA sequence of 14388
SEQ ID NO: 167 is the determined cDNA sequence of 14399
SEQ ID NO: 168 is the determined cDNA sequence of 14406
SEQ ID NO: 169 is the determined cDNA sequence of 14407
SEQ ID NO: 170 is the determined cDNA sequence of 14408
SEQ ID NO: 171 is the determined cDNA sequence of 14417
SEQ ID NO: 172 is the determined cDNA sequence of 14418
SEQ ID NO: 173 is the determined cDNA sequence of 14423
SEQ ID NO: 174 is the determined cDNA sequence of 14424
SEQ ID NO: 175 is the determined cDNA sequence of B726P-20
SEQ ID NO: 176 is the predicted amino acid sequence of B726P-20
SEQ ID NO: 177 is a PCR primer
SEQ ID NO: 178 is the determined cDNA sequence of B726P-74
SEQ ID NO: 179 is the predicted amino acid sequence of B726P-74
SEQ ID NO: 180 is the determined cDNA sequence of B726P-79
SEQ ID NO: 181 is the predicted amino acid sequence of B726P-79
SEQ ID NO: 182 is the determined cDNA sequence of 19439.1, showing homology to the mammaglobin gene
SEQ ID NO: 183 is the determined cDNA sequence of 19407.1, showing homology to the human keratin gene
SEQ ID NO: 184 is the determined cDNA sequence of 19428.1, showing homology to human chromosome 17 clone
SEQ ID NO: 185 is the determined cDNA sequence of B808P (19408), showing no significant homology to any known gene
SEQ ID NO: 186 is the determined cDNA sequence of 19460.1, showing no significant homology to any known gene
SEQ ID NO: 187 is the determined cDNA sequence of 19419.1, showing homology to Ig kappa light chain SEQ ID NO: 188 is the determined cDNA sequence of 19411.1, showing homology to human alpha-1 collagen SEQ ID NO: 189 is the determined cDNA sequence of 19420.1, showing homology to mus musculus proteinase-3

SEQ ID NO: 190 is the determined cDNA sequence of 19432.1, showing homology to human high motility group box SEQ ID NO: 191 is the determined cDNA sequence of 19412.1, showing homology to the human plaminogen activator gene SEQ ID NO: 192 is the determined cDNA sequence of 19415.1, showing homology to mitogen activated protein kinase SEQ ID NO: 193 is the determined cDNA sequence of 19409.1, showing homology to the chondroitin sulfate proteoglycan protein SEQ ID NO: 194 is the determined cDNA sequence of 19406.1, showing no significant homology to any known gene SEQ ID NO: 195 is the determined cDNA sequence of 19421.1, showing homology to human fibronectin SEQ ID NO: 196 is the determined cDNA sequence of 19426.1, showing homology to the retinoic acid receptor responder 3

SEQ ID NO: 197 is the determined cDNA sequence of 19425.1, showing homology to MyD88 mRNA SEQ ID NO: 198 is the determined cDNA sequence of 19424.1, showing homology to peptide transporter (TAP-1) mRNA SEQ ID NO: 199 is the determined cDNA sequence of 19429.1, showing no significant homology to any known gene SEQ ID NO: 200 is the determined cDNA sequence of 19435.1, showing homology to human polymorphic epithelial mucin SEQ ID NO: 201 is the determined cDNA sequence of B813P (19434.1), showing homology to human GATA-3 transcription factor SEQ ID NO: 202 is the determined cDNA sequence of 19461.1, showing homology to the human AP-2 gene SEQ ID NO: 203 is the determined cDNA sequence of 19450.1, showing homology to DNA binding regulatory factor SEQ ID NO: 204 is the determined cDNA sequence of 19451.1, showing homology to Na/H exchange regulatory co-factor SEQ ID NO: 205 is the determined cDNA sequence of 19462.1, showing no significant homology to any known gene SEQ ID NO: 206 is the determined cDNA sequence of 19455.1, showing homology to human mRNA for histone HAS.Z SEQ ID NO: 207 is the determined cDNA sequence of 19459.1, showing homology to PAC clone 179N16

SEQ ID NO: 208 is the determined cDNA sequence of 19464.1, showing no significant homology to any known gene SEQ ID NO: 209 is the determined cDNA sequence of 19414.1, showing homology to lipophilin B SEQ ID NO: 210 is the determined cDNA sequence of 19413.1, showing homology to chromosome 17 clone hRPK.209_J.20

SEQ ID NO: 211 is the determined cDNA sequence of 19416.1, showing no significant homology to any known gene SEQ ID NO: 212 is the determined cDNA sequence of 19437.1, showing homology to human clone 24976 mRNA SEQ ID NO: 213 is the determined cDNA sequence of 19449.1, showing homology to mouse DNA for PG-M core protein SEQ ID NO: 214 is the determined cDNA sequence of 19446.1, showing no significant homology to any known gene SEQ ID NO: 215 is the determined cDNA sequence of 19452.1, showing no significant homology to any known gene SEQ ID NO: 216 is the determined cDNA sequence of 19483.1, showing no significant homology to any known gene SEQ ID NO: 217 is the determined cDNA sequence of 19526.1, showing homology to human lipophilin C SEQ ID NO: 218 is the determined cDNA sequence of 19484.1, showing homology to the secreted cement gland protein XAG-2

SEQ ID NO: 219 is the determined cDNA sequence of 19470.1, showing no significant homology to any known gene SEQ ID NO: 220 is the determined cDNA sequence of 19469.1, showing homology to the human HLA-DM gene SEQ ID NO: 221 is the determined cDNA sequence of 19482.1, showing homology to the human pS2 protein gene SEQ ID NO: 222 is the determined cDNA sequence of B805P (19468.1), showing no significant homology to any known gene SEQ ID NO: 223 is the determined cDNA sequence of 19467.1, showing homology to human thrombospondin mRNA SEQ ID NO: 224 is the determined cDNA sequence of 19498.1, showing homology to the CDC2 gene involved in cell cycle control SEQ ID NO: 225 is the determined cDNA sequence of 19506.1, showing homology to human cDNA for TREB protein SEQ ID NO: 226 is the determined cDNA sequence of B806P (19505.1), showing no significant homology to any known gene SEQ ID NO: 227 is the determined cDNA sequence of 19486.1, showing homology to type I epidermal keratin SEQ ID NO: 228 is the determined cDNA sequence of 19510.1, showing homology to glucose transporter for glycoprotein SEQ ID NO: 229 is the determined cDNA sequence of 19512.1, showing homology to the human lysyl hydroxylase gene SEQ ID NO: 230 is the determined cDNA sequence of 19511.1 showing homology to human palimotoyl-protein thioesterase SEQ ID NO: 231 is the determined cDNA sequence of 19508.1, showing homology to human alpha enolase SEQ ID NO: 232 is the determined cDNA sequence of B807P (19509.1), showing no significant homology to any known gene SEQ ID NO: 233 is the determined cDNA sequence of B809P (19520.1), showing homology to clone 102D24 on chromosome 11q13.31

SEQ ID NO: 234 is the determined cDNA sequence of 19507.1, showing homology toprosome beta-subunit SEQ ID NO: 235 is the determined cDNA sequence of 19525.1, showing homology to human pro-urokinase precursor SEQ ID NO: 236 is the determined cDNA sequence of 19513.1, showing no significant homology to any known gene SEQ ID NO: 237 is the determined cDNA sequence of 19517.1, showing homology to human PAC 128M 19 clone SEQ ID NO: 238 is the determined cDNA sequence of 19564.1, showing homology to human cytochrome P450-IIB SEQ ID NO: 239 is the determined cDNA sequence of 19553.1, showing homology to human GABA-A receptor pi subunit SEQ ID NO: 240 is the determined cDNA sequence of B811 P (19575.1), showing no significant homology to any known gene SEQ ID NO: 241 is the determined cDNA sequence of B810P (19560.1), showing no significant homology to any known gene SEQ ID NO: 242 is the determined cDNA sequence of 19588.1, showing homology to aortic carboxypetidase-like protein SEQ ID NO: 243 is the determined cDNA sequence of 19551.1, showing homology to human BCL-1 gene SEQ ID NO: 244 is the determined cDNA sequence of 19567.1, showing homology to human proteasome-related mRNA SEQ ID NO: 245 is the determined cDNA sequence of B803P (19583.1), showing no significant homology to any known gene SEQ ID NO: 246 is the determined cDNA sequence of B812P (19587.1), showing no significant homology to any known gene SEQ ID NO: 247 is the determined cDNA sequence of B802P (19392.2), showing homology to human chromosome 17

SEQ ID NO: 248 is the determined cDNA sequence of 19393.2, showing homology to human nicein B2 chain SEQ ID NO: 249 is the determined cDNA sequence of 19398.2, human MHC class II DQ alpha mRNA SEQ ID NO: 250 is the determined cDNA sequence of B804P (19399.2), showing homology to human Xp22 BAC GSHB-184P14

SEQ ID NO: 251 is the determined cDNA sequence of 19401.2, showing homology to human ikB kinase-b gene SEQ ID NO: 252 is the determined cDNA sequence of 20266, showing no significant homology to any known gene SEQ ID NO: 253 is the determined cDNA sequence of B826P (20270), showing no significant homology to any known gene SEQ ID NO: 254 is the determined cDNA sequence of 20274, showing no significant homology to any known gene SEQ ID NO: 255 is the determined cDNA sequence of 20276, showing no significant homology to any known gene SEQ ID NO: 256 is the determined cDNA sequence of 20277, showing no significant homology to any known gene SEQ ID NO: 257 is the determined cDNA sequence of B823P (20280), showing no significant homology to any known gene SEQ ID NO: 258 is the determined cDNA sequence of B821P (20281), showing no significant homology to any known gene SEQ ID NO: 259 is the determined cDNA sequence of B824P (20294), showing no significant homology to any known gene SEQ ID NO: 260 is the determined cDNA sequence of 20303, showing no significant homology to any known gene SEQ ID NO: 261 is the determined cDNA sequence of 20310, showing no significant homology to any known gene SEQ ID NO: 262 is the determined cDNA sequence of B825P (20336), showing no significant homology to any known gene SEQ ID NO: 263 is the determined cDNA sequence of B827P (20341), showing no significant homology to any known gene SEQ ID NO: 264 is the determined cDNA sequence of 20941, showing no significant homology to any known gene SEQ ID NO: 265 is the determined cDNA sequence of 20954, showing no significant homology to any known gene SEQ ID NO: 266 is the determined cDNA sequence of 20961, showing no significant homology to any known gene SEQ ID NO: 267 is the determined cDNA sequence of 20965, showing no significant homology to any known gene SEQ ID NO: 268 is the determined cDNA sequence of 20975, showing no significant homology to any known gene SEQ ID NO: 269 is the determined cDNA sequence of 20261, showing homology to Human p120 catenin SEQ ID NO: 270 is the determined cDNA sequence of B822P (20262), showing homology to Human membrane glycoprotein 4F2

SEQ ID NO: 271 is the determined cDNA sequence of 20265, showing homology to Human Na, K-ATPase Alpha 1

SEQ ID NO: 272 is the determined cDNA sequence of 20267, showing homology to Human heart HS 90, partial cds SEQ ID NO: 273 is the determined cDNA sequence of 20268, showing homology to Human mRNA GPI-anchored protein p137

SEQ ID NO: 274 is the determined cDNA sequence of 20271, showing homology to Human cleavage stimulation factor 77 kDa subunit SEQ ID NO: 275 is the determined cDNA sequence of 20272, showing homology to Human p 190-B SEQ ID NO: 276 is the determined cDNA sequence of 20273, showing homology to Human ribophorin SEQ ID NO: 277 is the determined cDNA sequence of 20278, showing homology to Human ornithine amino transferase SEQ ID NO: 278 is the determined cDNA sequence of 20279, showing homology to Human S-adenosylmethionine synthetase SEQ ID NO: 279 is the determined cDNA sequence of 20293, showing homology to Human x inactivation transcript SEQ ID NO: 280 is the determined cDNA sequence of 20300, showing homology to Human cytochrome p450

SEQ ID NO: 281 is the determined cDNA sequence of 20305, showing homology to Human elongation factor-1 alpha SEQ ID NO: 282 is the determined cDNA sequence of 20306, showing homology to Human epithelial ets protein SEQ ID NO: 283 is the determined cDNA sequence of 20307, showing homology to Human signal transducer mRNA SEQ ID NO: 284 is the determined cDNA sequence of 20313, showing homology to Human GABA-A receptor pi subunit mRNA SEQ ID NO: 285 is the determined cDNA sequence of 20317, showing homology to Human tyrosine phosphatase SEQ ID NO: 286 is the determined cDNA sequence of 20318, showing homology to Human cathepsine B proteinase SEQ ID NO: 287 is the determined cDNA sequence of 20320, showing homology to Human 2-phosphopyruvate-hydratase-alpha-enolase SEQ ID NO: 288 is the determined cDNA sequence of 20321, showing homology to Human E-cadherin SEQ ID NO: 289 is the determined cDNA sequence of 20322, showing homology to Human hsp86

SEQ ID NO: 290 is the determined cDNA sequence of B828P (20326), showing homology to Human x inactivation transcript SEQ ID NO: 291 is the determined cDNA sequence of 20333, showing homology to Human chromatin regulator, SMARCA5

SEQ ID NO: 292 is the determined cDNA sequence of 20335, showing homology to Human sphingolipid activator protein 1

SEQ ID NO: 293 is the determined cDNA sequence of 20337, showing homology to Human hepatocyte growth factor activator inhibitor type 2

SEQ ID NO: 294 is the determined cDNA sequence of 20338, showing homology to Human cell ashesion molecule CD44

SEQ ID NO: 295 is the determined cDNA sequence of 20340, showing homology to Human nuclear factor (erythroid-derived)-like 1

SEQ ID NO: 296 is the determined cDNA sequence of 20938, showing homology to Human vinculin mRNA SEQ ID NO: 297 is the determined cDNA sequence of 20939, showing homology to Human elongation factor EF-1-alpha SEQ ID NO: 298 is the determined cDNA sequence of 20940, showing homology to Human nestin gene SEQ ID NO: 299 is the determined cDNA sequence of 20942, showing homology to Human pancreatic ribonuclease SEQ ID NO: 300 is the determined cDNA sequence of 20943, showing homology to Human transcobalamin I SEQ ID NO: 301 is the determined cDNA sequence of 20944, showing homology to Human beta-tubulin SEQ ID NO: 302 is the determined cDNA sequence of 20946, showing homology to Human HS1 protein SEQ ID NO: 303 is the determined cDNA sequence of 20947, showing homology to Human cathepsin B SEQ ID NO: 304 is the determined cDNA sequence of 20948, showing homology to Human testis enhanced gene transcript SEQ ID NO: 305 is the determined cDNA sequence of 20949, showing homology to Human elongation factor EF-1-alpha SEQ ID NO: 306 is the determined cDNA sequence of 20950, showing homology to Human ADP-ribosylation factor 3

SEQ ID NO: 307 is the determined cDNA sequence of 20951, showing homology to Human IFP53 or WRS for tryptophanyl-tRNA synthetase SEQ ID NO: 308 is the determined cDNA sequence of 20952, showing homology to Human cyclin-dependent protein kinase SEQ ID NO: 308 is the determined cDNA sequence of 20957, showing homology to Human alpha-tubulin sioform 1

SEQ ID NO: 309 is the determined cDNA sequence of 20959, showing homology to Human tyrosine phosphatase-61bp deletion SEQ ID NO: 310 is the determined cDNA sequence of 20966, showing homology to Human tyrosine phosphatase SEQ ID NO: 311 is the determined cDNA sequence of B830P (20976), showing homology to Human nuclear factor NF 45

SEQ ID NO: 312 is the determined cDNA sequence of B829P (20977), showing homology to Human delta-6 fatty acid desaturase SEQ ID NO: 313 is the determined cDNA sequence of 20978, showing homology to Human nuclear aconitase SEQ ID NO: 314 is the determined cDNA sequence of 19465, showing no significant homology to any known gene.

DETAILED DESCRIPTION OF THE INVENTION

As noted above, the present invention is generally directed to compositions and methods for the treatment and diagnosis of breast cancer. The inventive compositions are generally isolated polypeptides that comprise at least a portion of a breast tumor antigen. Also included within the present invention are molecules (such as an antibody or fragment thereof) that bind to the inventive polypeptides. Such molecules are referred to herein as "binding agents."

In particular, the subject invention discloses polypeptides comprising at least a portion of a human breast tumor antigen, or a variant thereof, wherein the breast tumor antigen includes an amino acid sequence encoded by a polynucleotide including a sequence selected from the group consisting of: nucleotide sequences recited in SEQ ID NO: 1–61, 63–175, 178, 180 and 182–313, the complements of said nucleotide sequences, and variants thereof. As used herein, the term "polypeptide" encompasses amino acid chains of any length, including full length proteins, wherein the amino acid residues are linked by covalent peptide bonds. Thus, a polypeptide comprising a portion of one of the above breast antigens may consist entirely of the portion, or the portion may be present within a larger polypeptide that contains additional sequences. The additional sequences may be derived from the native protein or may be heterologous, and such sequences may be immunoreactive and/or antigenic.

As used herein, an "immunogenic portion" of a human breast tumor antigen is a portion that is capable of eliciting an immune response in a patient inflicted with breast cancer and as such binds to antibodies present within sera from a breast cancer patient. Such immunogenic portions generally comprise at least about 5 amino acid residues, more preferably at least about 10, and most preferably at least about 20 amino acid residues. Immunogenic portions of the proteins described herein may be identified in antibody binding assays. Such assays may generally be performed using any of a variety of means known to those of ordinary skill in the art, as described, for example, in Harlow and Lane, *Antibodies: A Laboratory Manual,* Cold Spring Harbor Laboratory, Cold Spring Harbor, N.Y., 1988. For example, a polypeptide may be immobilized on a solid support (as described below) and contacted with patient sera to allow binding of antibodies within the sera to the immobilized polypeptide. Unbound sera may then be removed and bound antibodies detected using, for example, $^{125}$I-labeled Protein A. Alternatively, a polypeptide may be used to generate monoclonal and polyclonal antibodies for use in detection of the polypeptide in blood or other fluids of breast cancer patients. Methods for preparing and identifying immunogenic portions of antigens of known sequence are well known in the art and include those summarized in Paul, *Fundamental Immunology*, 3$^{rd}$ ed., Raven Press, 1993, pp. 243–247.

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a polynucleotide in a generally one-to-one manner. An mRNA molecule corresponds to an HnRNA and polynucleotide from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments.

The compositions and methods of the present invention also encompass variants of the above polypeptides and polynucleotides. Such variants include, but are not limited to, naturally occurring allelic variants of the inventive sequences.

A polypeptide "variant," as used herein, is a polypeptide that differs from the recited polypeptide only in conservative substitutions and/or modifications, such that the antigenic properties of the polypeptide are retained. In a preferred embodiment, variant polypeptides differ from an identified sequence by substitution, deletion or addition of five amino acids or fewer. Such variants may generally be identified by modifying one of the above polypeptide sequences, and evaluating the antigenic properties of the modified polypeptide using, for example, the representative procedures described herein. Polypeptide variants preferably exhibit at least about 70%, more preferably at least about 90% and most preferably at least about 95% identity (determined as described below) to the identified polypeptides.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his.

Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (*DNA*, 2:183, 1983). Nucleotide variants may be naturally occurring allelic variants, or non-naturally occurring variants. Variant nucleotide sequences preferably exhibit at least about 70%, more preferably at least about 80% and most preferably at least about 90% identity (determined as described below) to the recited sequence.

The breast tumor antigens provided by the present invention include variants that are encoded by DNA sequences which are substantially homologous to one or more of the DNA sequences specifically recited herein. "Substantial homology," as used herein, refers to DNA sequences that are capable of hybridizing under moderately stringent conditions. Suitable moderately stringent conditions include prewashing in a solution of 5×SSC, 0.5% SDS, 1.0 mM EDTA (pH 8.0); hybridizing at 50° C.–65° C., 5×SSC, overnight or, in the event of cross-species homology, at 45° C. with 0.5×SSC; followed by washing twice at 65° C. for 20 minutes with each of 2×, 0.5× and 0.2×SSC containing 0.1% SDS. Such hybridizing DNA sequences are also within the scope of this invention, as are nucleotide sequences that, due to code degeneracy, encode an immunogenic polypeptide that is encoded by a hybridizing DNA sequence.

Two nucleotide or polypeptide sequences are said to be "identical" if the sequence of nucleotides or amino acid residues in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Resarch Foundaiton, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) Fast and sensitive multiple sequence alignments on a microcomputer *CABIOS* 5:151–153; Myers, E. W. and Muller W. (1988) Optimal alignments in linear space *CABIOS* 4:11–17; Robinson. E. D. (1971) *Comb. Theor* 11: 105; Santou, N. Nes, M. (1987) The neighbor joining method. A new method for reconstructing phylogenetic trees *Mol. Biol. Evol.* 4:406–425, Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) Rapid similarity searches of nucleic acid and protein data banks *Proc. Natl. Acad., Sci. USA* 80:726–730.

Preferably, the "percentage of sequence identity" is determined by comparing two optimally aligned sequences over a window of comparison of at least 20 positions, wherein the portion of the polynucleotide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

The breast tumor antigens of the present invention, and polynucleotides encoding such antigens, may be isolated from breast tumor tissue using any of a variety of methods well known in the art. DNA sequences corresponding to a gene (or a portion thereof) encoding one of the inventive breast tumor antigens may be isolated from a breast tumor cDNA library using a subtraction technique as described in detail below. Examples of such DNA sequences are provided in SEQ ID NO: 1–61, 63–175, 178, 180 and 182–313. Partial DNA sequences thus obtained may be used to design oligonucleotide primers for the amplification of full-length DNA sequences in a polymerase chain reaction (PCR), using techniques well known in the art (see, for example, Mullis et al., *Cold Spring Harbor Symp. Quant. Biol.*, 51:263, 1987; Erlich ed., *PCR Technology,* Stockton Press, NY, 1989). Once a DNA sequence encoding a polypeptide is obtained, any of the above modifications may be readily introduced using standard mutagenesis techniques, such as oligonucleotide-directed site-specific mutagenesis as taught, for example, by Adelman et al. (*DNA,* 2:183, 1983).

The breast tumor polypeptides disclosed herein may also be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain (see, for example, Merrifield, *J. Am. Chem. Soc.* 85:2149–2146, 1963). Equipment for automated synthesis of polypeptides is commercially available from suppliers such as Perkin Elmer/Applied BioSystems Division (Foster City, Calif.), and may be operated according to the manufacturer's instructions.

Alternatively, any of the above polypeptides may be produced recombinantly by inserting a DNA sequence that encodes the polypeptide into an expression vector and expressing the protein in an appropriate host. Any of a variety of expression vectors known to those of ordinary skill in the art may be employed to express recombinant polypeptides of this invention. Expression may be achieved in any appropriate host cell that has been transformed or transfected with an expression vector containing a polynucleotide that encodes a recombinant polypeptide. Suitable host cells include prokaryotes, yeast and higher eukaryotic cells. Preferably, the host cells employed are *E. coli*, yeast or a mammalian cell line, such as CHO cells. The DNA sequences expressed in this manner may encode naturally occurring polypeptides, portions of naturally occurring polypeptides, or other variants thereof.

In general, regardless of the method of preparation, the polypeptides disclosed herein are prepared in an isolated, substantially pure, form (i.e., the polypeptides are homogenous as determined by amino acid composition and primary sequence analysis). Preferably, the polypeptides are at least about 90% pure, more preferably at least about 95% pure and most preferably at least about 99% pure. In certain preferred embodiments, described in more detail below, the substantially pure polypeptides are incorporated into pharmaceutical compositions or vaccines for use in one or more of the methods disclosed herein.

In a related aspect, the present invention provides fusion proteins comprising a first and a second inventive polypeptide or, alternatively, a polypeptide of the present invention and a known breast tumor antigen, together with variants of such fusion proteins.

A DNA sequence encoding a fusion protein of the present invention is constructed using known recombinant DNA techniques to assemble separate DNA sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad Sci. USA* 83:8258–8262, 1986; U.S. Pat. Nos. 4,935,233 and 4,751,180. The linker sequence may be from 1 to about 50 amino acids in length. Peptide sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons require to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.,* 336:86–91 (1997)).

Polypeptides of the present invention that comprise an immunogenic portion of a breast tumor antigen may generally be used for immunotherapy of breast cancer, wherein the polypeptide stimulates the patient's own immune response to breast tumor cells. The present invention thus provides methods for using one or more of the immunoreactive polypeptides encoded by a polynucleotide comprising a sequence of SEQ ID NO: 1–61, 63–175, 178, 180 and 182–313 (or fusion proteins comprising one or more such polypeptides and/or DNA encoding such polypeptides) for immunotherapy of breast cancer in a patient. As used herein, a "patient" refers to any warm-blooded animal, preferably a human. A patient may be afflicted with a disease, or may be free of detectable disease. Accordingly, the above immunoreactive polypeptides (or fusion proteins or polynucleotides encoding such polypeptides) may be used to treat breast cancer or to inhibit the development of breast cancer. The polypeptides may be administered either prior to or following surgical removal of primary tumors and/or treatment by administration of radiotherapy and conventional chemotherapeutic drugs.

In these aspects, the polypeptide or fusion protein is generally present within a pharmaceutical composition and/or a vaccine. Pharmaceutical compositions may comprise one or more polypeptides, each of which may contain one or more of the inventive sequences (or variants thereof), and a physiologically acceptable carrier. The vaccines may comprise one or more such polypeptides and a non-specific immune response enhancer, wherein the non-specific immune response enhancer is capable of eliciting or enhancing an immune response to an exogenous antigen. Examples of non-specific-immune response enhancers include adjuvants, biodegradable microspheres (e.g., polylactic galactide) and liposomes (into which the polypeptide is incorporated). Pharmaceutical compositions and vaccines may also contain other epitopes of breast tumor antigens, either incorporated into a combination polypeptide (i.e., a single polypeptide that contains multiple epitopes) or present within a separate polypeptide.

Alternatively, a pharmaceutical composition or vaccine may contain DNA encoding one or more of the above polypeptides, such that the polypeptide is generated in situ. In such pharmaceutical compositions and vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter). Bacterial delivery systems involve the administration of a bacterium (such as *Bacillus-Calmette-Gierrin*) that expresses an epitope of a breast tumor cell antigen on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *PNAS* 91:215–219, 1994; Kass-Eisler et al., *PNAS* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in published PCT application WO 90/11092, and Ulmer et al., *Science* 259:1745–1749, 1993, reviewed by Cohen, *Science* 259:1691–1692, 1993. The uptake of naked DNA may be increased by coating the DNA onto biodegradable beads, which are efficiently transported into the cells.

Routes and frequency of administration, as well as dosage, will vary from individual to individual and may parallel those currently being used in immunotherapy of other diseases. In general, the pharmaceutical compositions and vaccines may be administered by injection (e.g., intracutaneous, intramuscular, intravenous or subcutaneous), intranasally (e.g., by aspiration) or orally. Between 1 and 10 doses may be administered over a 3–24 week period. Preferably, 4 doses are administered, at an interval of 3 months, and booster administrations may be given periodically thereafter. Alternate protocols may be appropriate for individual patients. A suitable dose is an amount of polypeptide or DNA that is effective to raise an immune response (cellular and/or humoral) against breast tumor cells in a treated patient. A suitable immune response is at least 10–50% above the basal (i.e., untreated) level. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 $\mu$g. Suitable dose sizes will vary with the size of the patient, but will typically range from about 0.01 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a lipid, a wax and/or a buffer. For oral administration, any of the above carriers or a solid carrier, such as mannitol, lactose, starch, magnesium stearate, sodium saccharine, talcum, cellulose, glucose, sucrose, and/or magnesium carbonate, may be employed. Biodegradable microspheres (e.g., polylactic glycolide) may also be employed as carriers for the pharmaceutical compositions of this invention. Suitable biodegradable microspheres are disclosed, for example, in U.S. Pat. Nos. 4,897,268 and 5,075,109.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a nonspecific stimulator of immune response, such as lipid A, *Bordella pertussis* or *Mycobacterium tuberculosis*. Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

Polypeptides disclosed herein may also be employed in adoptive immunotherapy for the treatment of cancer. Adoptive immunotherapy may be broadly classified into either active or passive immunotherapy. In active immunotherapy, treatment relies on the in vivo stimulation of the endogenous host immune system to react against tumors with the administration of immune response-modifying agents (for example, tumor vaccines, bacterial adjuvants, and/or cytokines).

In passive immunotherapy, treatment involves the delivery of biologic reagents with established tumor-immune reactivity (such as effector cells or antibodies) that can directly or indirectly mediate antitumor effects and does not necessarily depend on an intact host immune system. Examples of effector cells include T lymphocytes (for example, CD8+ cytotoxic T-lymphocyte, CD4+ T-helper, gamma/delta T lymphocytes, tumor-infiltrating lymphocytes), killer cells (such as Natural Killer cells, lymphokine-activated killer cells), B cells, or antigen presenting cells (such as dendritic cells and macrophages) expressing the disclosed antigens. The polypeptides disclosed herein may also be used to generate antibodies or anti-idiotypic antibodies (as in U.S. Pat. No. 4,918,164), for passive immunotherapy.

The predominant method of procuring adequate numbers of T-cells for adoptive immunotherapy is to grow immune T-cells in vitro. Culture conditions for expanding single antigen-specific T-cells to several billion in number with retention of antigen recognition in vivo are well known in the art. These in vitro culture conditions typically utilize intermittent stimulation with antigen, often in the presence of cytokines, such as IL-2, and non-dividing feeder cells. As noted above, the immunoreactive polypeptides described herein may be used to rapidly expand antigen-specific T cell cultures in order to generate sufficient number of cells for immunotherapy. In particular, antigen-presenting cells, such as dendritic, macrophage, monocyte, fibroblast or B-cells, may be pulsed with immunoreactive polypeptides or polynucleotide sequence(s) may be introduced into antigen presenting cells, using standard techniques well known in the art. For example, antigen presenting cells may be transfected or transduced with a polynucleotide sequence, wherein said sequence contains a promoter region appropriate for inducing expression, and can be expressed as part of a recombinant virus or other expression system. Several viral vectors may be used to transduce an antigen presenting cell, including pox virus, vaccinia virus, and adenovirus. Antigen presenting cells may be transfected with polynucleotide sequences disclosed herein by a variety of means, including gene-gun technology, lipid-mediated delivery, electroporation, osmotic shock, and particulate delivery mechanisms, resulting in efficient and acceptable expression levels as determined by one of ordinary skill in the art. For cultured T-cells to be effective in therapy, the cultured T-cells must be able to grow and distribute widely and to survive long term in vivo. Studies have demonstrated that cultured T-cells can be induced to grow in vivo and to survive long term in substantial numbers by repeated stimulation with antigen supplemented with IL-2 (see, for example, Cheever et al. Ibid).

The polypeptides disclosed herein may also be employed to generate and/or isolate tumor-reactive T-cells, which can then be administered to the patient. In one technique, antigen-specific T-cell lines may be generated by in vivo immunization with short peptides corresponding to immunogenic portions of the disclosed polypeptides. The resulting antigen specific CD8+ CTL clones may be isolated from the patient, expanded using standard tissue culture techniques, and returned to the patient.

Alternatively, peptides corresponding to immunogenic portions of the polypeptides may be employed to generate tumor reactive T cell subsets by selective in vitro stimulation and expansion of autologous T cells to provide antigen-specific T cells which may be subsequently transferred to the patient as described, for example, by Chang et al. (*Crit. Rev. Oncol. Hematol.,* 22(3), 213, 1996). Cells of the immune system, such as T cells, may be isolated from the peripheral blood of a patient, using a commercially available cell separation system. The separated cells are stimulated with one or more of the immunoreactive polypeptides contained within a delivery vehicle, such as a microsphere, to provide antigen-specific T cells. The population of tumor antigen-specific T cells is then expanded using standard techniques and the cells are administered back to the patient.

In other embodiments, T-cell and/or antibody receptors specific for the polypeptides disclosed herein can be cloned, expanded, and transferred into other vectors or effector cells for use in adoptive immunotherapy. In particular, T cells may be transfected with the appropriate genes to express the variable domains from tumor specific monoclonal antibodies as the extracellular recognition elements and joined to the T cell receptor signaling chains, resulting in T cell activation, specific lysis, and cytokine release. This enables the T cell to redirect its specificity in an MHC-independent manner. See for example, Eshhar, Z., *Cancer Immunol Immunother,* 45(3–4):131–6, 1997 and Hwu, P., et al, *Cancer Res.* 55(15):3369–73, 1995. Another embodiment may include the transfection of tumor antigen specific alpha and beta T cell receptor chains into alternate T cells, as in Cole, D J, et al, *Cancer Res,* 55(4):748–52, 1995.

In further embodiments, syngeneic or autologous dendritic cells may be pulsed with peptides corresponding to at least an immunogenic portion of a polypeptide disclosed herein. The resulting antigen-specific dendritic cells may either be transferred into a patient, or employed to stimulate T cells to provide antigen-specific T cells which may, in turn, be administered to a patient. The use of peptide-pulsed dendritic cells to generate antigen-specific T cells and the subsequent use of such antigen-specific T cells to eradicate tumors in a murine model has been demonstrated by Cheever et al. ("Therapy With Cultured T Cells: Principles Revisited," *Immunological Reviews,* 157:177, 1997). Additionally vectors expressing the disclosed polynucleotides may be introduced into stem cells taken from the patient and clonally propagated in vitro for autologous transplant back into the same patient.

In one specific embodiment, cells of the immune system, such as T cells, may be isolated from the peripheral blood of a patient, using a commercially available cell separation system, such as CellPro Incorporated's (Bothell, Wash.) CEPRATE™ system (see U.S. Pat. Nos. 5,240,856; 5,215,926, WO 89/06280; WO 91/16116 and WO 92/07243). The separated cells are stimulated with one or more of the immunoreactive polypeptides contained within a delivery vehicle, such as a microsphere, to provide antigen-specific T cells. The population of tumor antigen-specific T cells is then expanded using standard techniques and the cells are administered back to the patient.

Additionally vectors expressing the disclosed polynucleotides may be introduced into stem cells taken from the patient and clonally propagated in vitro for autologous transplant back into the same patient.

Polypeptides of the present invention may also, or alternatively, be used to generate binding agents, such as antibodies or fragments thereof, that are capable of detecting metastatic human breast tumors. Binding agents of the present invention may generally be prepared using methods known to those of ordinary skill in the art, including the representative procedures described herein. Binding agents are capable of differentiating between patients with and without breast cancer, using the representative assays described herein. In other words, antibodies or other binding agents raised against a breast tumor antigen, or a suitable portion thereof, will generate a signal indicating the presence of primary or metastatic breast cancer in at least about 20% of patients afflicted with the disease, and will generate a negative signal indicating the absence of the disease in at least about 90% of individuals without primary or metastatic breast cancer. Suitable portions of such breast tumor antigens are portions that are able to generate a binding agent that indicates the presence of primary or metastatic breast cancer in substantially all (i.e., at least about 80%, and preferably at least about 90%) of the patients for which breast cancer would be indicated using the full length antigen, and that indicate the absence of breast cancer in substantially all of those samples that would be negative when tested with full length antigen. The representative assays described below, such as the two-antibody sandwich assay, may generally be employed for evaluating the ability of a binding agent to detect metastatic human breast tumors.

The ability of a polypeptide prepared as described herein to generate antibodies capable of detecting primary or metastatic human breast tumors may generally be evaluated by raising one or more antibodies against the polypeptide (using, for example, a representative method described herein) and determining the ability of such antibodies to detect such tumors in patients. This determination may be made by assaying biological samples from patients with and without primary or metastatic breast cancer for the presence of a polypeptide that binds to the generated antibodies. Such test assays may be performed, for example, using a representative procedure described below. Polypeptides that generate antibodies capable of detecting at least 20% of primary or metastatic breast tumors by such procedures are considered to be useful in assays for detecting primary or metastatic human breast tumors. Polypeptide specific antibodies may be used alone or in combination to improve sensitivity.

Polypeptides capable of detecting primary or metastatic human breast tumors may be used as markers for diagnosing breast cancer or for monitoring disease progression in patients. In one embodiment, breast cancer in a patient may be diagnosed by evaluating a biological sample obtained from the patient for the level of one or more of the above polypeptides, relative to a predetermined cut-off value. As used herein, suitable "biological samples" include blood, sera and urine.

The level of one or more of the above polypeptides may be evaluated using any binding agent specific for the polypeptide(s). A "binding agent," in the context of this invention, is any agent (such as a compound or a cell) that binds to a polypeptide as described above. As used herein, "binding" refers to a noncovalent association between two separate molecules (each of which may be free (i.e., in solution) or present on the surface of a cell or a solid support), such that a "complex" is formed. Such a complex may be free or immobilized (either covalently or noncovalently) on a support material The ability to bind may generally be evaluated by determining a binding constant for the formation of the complex. The binding constant is the value obtained when the concentration of the complex is divided by the product of the component concentrations. In general, two compounds are said to "bind" in the context of the present invention when the binding constant for complex formation exceeds about $10^3$ L/mol. The binding constant may be determined using methods well known to those of ordinary skill in the art.

Any agent that satisfies the above requirements may be a binding agent. For example, a binding agent may be a ribosome with or without a peptide component, an RNA molecule or a peptide. In a preferred embodiment, the binding partner is an antibody, or a fragment thereof. Such antibodies may be polyclonal, or monoclonal. In addition, the antibodies may be single chain, chimeric, CDR-grafted or humanized. Antibodies may be prepared by the methods described herein and by other methods well known to those of skill in the art.

There are a variety of assay formats known to those of ordinary skill in the art for using a binding partner to detect polypeptide markers in a sample. See, e.g., Harlow and Lane, *Antibodies: A Laboratory Manual*, Cold Spring Harbor Laboratory, 1988. In a preferred embodiment, the assay involves the use of binding partner immobilized on a solid support to bind to and remove the polypeptide from the remainder of the sample. The bound polypeptide may then be detected using a second binding partner that contains a reporter group. Suitable second binding partners include antibodies that bind to the binding partner/polypeptide complex. Alternatively, a competitive assay may be utilized, in which a polypeptide is labeled with a reporter group and allowed to bind to the immobilized binding partner after incubation of the binding partner with the sample. The extent to which components of the sample inhibit the binding of the labeled polypeptide to the binding partner is indicative of the reactivity of the sample with the immobilized binding partner.

The solid support may be any material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 µg, and preferably about 100 ng to about 1 µg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with. the sample, such that polypeptides within the sample are allowed to bind to the immobilized antibody. Unbound sample is then removed from the immobilized polypeptide-antibody complexes and a second antibody (containing a reporter group) capable of binding to a different site on the polypeptide is added. The amount of second antibody that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is that period of time that is sufficient to detect the presence of polypeptide within a sample obtained from an individual with breast cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween20™ The second antibody, which contains a reporter group, may then be added to the solid support. Preferred reporter groups include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

The second antibody is then incubated with the immobilized antibody-polypeptide complex for an amount of time sufficient to detect the bound polypeptide. An appropriate amount of time may generally be determined by assaying the level of binding that occurs over a period of time. Unbound second antibody is then removed and bound second antibody is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of breast cancer, the signal detected from the reporter group that remains bound to the solid support is generally compared to a signal that corresponds to a predetermined cut-off value. In one preferred embodiment, the cut-off value is the average mean signal obtained when the immobilized antibody is incubated with samples from patients without breast cancer. In general, a sample generating a signal that is three standard deviations above the predetermined cut-off value is considered positive for breast cancer. In an alternate preferred embodiment, the cut-off value is determined using a Receiver Operator Curve, according to the method of Sackett et al., *Clinical Epidemiology: A Basic Science for Clinical Medicine,* Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for breast cancer.

In a related embodiment., the assay is performed in a flow-through or strip test format, wherein the antibody is immobilized on a membrane, such as nitrocellulose. In the flow-through test, polypeptides within the sample bind to the immobilized antibody as the sample passes through the membrane. A second, labeled antibody then binds to the antibody-polypeptide complex as a solution containing the second antibody flows through the membrane. The detection of bound second antibody may then be performed as described above. In the strip test format, one end of the membrane to which antibody is bound is immersed in a solution containing the sample. The sample migrates along the membrane through a region containing second antibody and to the area of immobilized antibody. Concentration of second antibody at the area of immobilized antibody indicates the presence of breast cancer. Typically, the concentration of second antibody at that site generates a pattern, such as a line, that can be read visually. The absence of such a pattern indicates a negative result. In general, the amount of antibody immobilized on the membrane is selected to generate a visually discernible pattern when the biological sample contains a level of polypeptide that would be sufficient to generate a positive signal in the two-antibody sandwich assay, in the format discussed above. Preferably, the amount of antibody immobilized on the membrane ranges from about 25 ng to about 1 $\mu$g, and more preferably from about 50 ng to about 500 ng. Such tests can typically be performed with a very small amount of biological sample.

Of course, numerous other assay protocols exist that are suitable for use with the antigens or antibodies of the present invention. The above descriptions are intended to be exemplary only.

In another embodiment, the above polypeptides may be used as markers for the progression of breast cancer. In this embodiment, assays as described above for the diagnosis of breast cancer may be performed over time, and the change in the level of reactive polypeptide(s) evaluated. For example, the assays may be performed every 24–72 hours for a period of 6 months to 1 year, and thereafter performed as needed. In general, breast cancer is progressing in those patients in whom the level of polypeptide detected by the binding agent increases over time. In contrast, breast cancer is not progressing when the level of reactive polypeptide either remains constant or decreases with time.

Antibodies for use in the above methods may be prepared by any of a variety of techniques known to those of ordinary skill in the art. See, e.g., Harlow and Lane, *Antibodies: A Laboratory Manual,* Cold Spring Harbor Laboratory, 1988. In one such technique, an immunogen comprising the antigenic polypeptide is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Monoclonal antibodies of the present invention may also be used as therapeutic reagents, to diminish or eliminate breast tumors. The antibodies may be used on their own (for instance, to inhibit metastases) or coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group. such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co:, Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify breast tumor-specific cDNA derived from a biological sample, wherein at least one of the oligonucleotide primers is specific for a polynucleotide encoding a breast tumor protein of the present invention. The presence of the amplified cDNA is then detected using techniques well known in the art, such as gel electrophoresis. Similarly, oligonucleotide probes specific for a polynucleotide encoding a breast tumor protein of the present invention may be used in a hybridization assay to detect the presence of an inventive polypeptide in a biological sample.

As used herein, the term "oligonucleotide primer/probe specific for a polynucleotide" means an oligonucleotide sequence that has at least about 60%, preferably at least about 75% and more preferably at least about 90%, identity to the polynucleotide in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a polynucleotide comprising a sequence selected from SEQ ID NO: 1–61, 63–175, 178, 180 and 182–313. Preferably, oligonucleotide probes for use in the inventive diagnostic methods comprise at least about 15 contiguous oligonucleotides of a polynucleotide comprising a sequence provided in SEQ ID NO: 1–61, 63–175, 178, 180 and 182–313. Techniques for both PCR based assays and hybridization assays are well known in the art (see, for example, Mullis et al. *Ibid*; Ehrlich, *Ibid*). Primers or probes may thus be used to detect breast tumor-specific sequences in biological samples, including blood, urine and/or breast tumor tissue.

The following Examples are offered by way of illustration and not by way of limitation.

EXAMPLES

Example 1

Isolation and Characterization of Breast Tumor Polypeptides

This Example describes the isolation of breast tumor polypeptides from a breast tumor cDNA library.

A cDNA subtraction library containing cDNA from breast tumor subtracted with normal breast cDNA was constructed as follows. Total RNA was extracted from primary tissues using Trizol reagent (Gibco BRL Life Technologies, Gaithersburg, Md.) as described by the manufacturer. The polyA+ RNA was purified using an oligo(dT) cellulose column according to standard protocols First strand cDNA was synthesized using the primer supplied in a Clontech PCR-Select cDNA Subtraction Kit (Clontech, Palo Alto, Calif.). The driver DNA consisted of cDNAs from two normal breast tissues with the tester cDNA being from three primary breast tumors. Double-stranded cDNA was synthesized for both tester and driver, and digested with a combination of endonucleases (MluI, MscI, PvuII, SalI and StuI) which recognize six base pairs DNA. This modification increased the average cDNA size dramatically compared with cDNAs generated according to Clontech's protocol. The digested tester cDNAs were ligated to two different adaptors and the subtraction was performed according to Clontech's protocol. The subtracted cDNAs were subjected to two rounds of PCR amplification, following the manufacturer's protocol. The resulting PCR products were subcloned into the TA cloning vector, pCRII (Invitrogen, San Diego, Calif.) and transformed into ElectroMax *E. coli* DH10B cells (Gibco BRL Life, Technologies) by electroporation. DNA was isolated from independent clones and sequenced using a Perkin Elmer/Applied Biosystems Division (Foster City, Calif.) Automated Sequencer Model 373A.

Sixty-three distinct cDNA clones were found in the subtracted breast tumor-specific cDNA library. The determined one strand (5' or 3') cDNA sequences for the clones are provided in SEQ ID NO: 1–61, 72 and 73, respectively. Comparison of these cDNA sequences with known sequences in the gene bank using the EMBL and GenBank databases (Release 97) revealed no significant homologies to the sequences provided in SEQ ID NO: 14, 21, 22, 27, 29, 30, 32, 38, 44, 45, 53, 72 and 73. The sequences of SEQ ID NO: 1, 3, 16, 17, 34, 48, 57, 60 and 61 were found to represent known human genes. The sequences of SEQ ID NO: 2, 4, 23, 39 and 50 were found to show some similarity to previously identified non-human genes. The remaining clones (SEQ ID NO: 5–13, 15, 18–20, 24–26, 28, 31, 33, 35–37, 40–43, 46, 47, 49, 51, 52, 54–56, 58 and 59) were found to show at least some degree of homology to previously identified expressed sequence tags (ESTs).

To determine mRNA expression levels of the isolated cDNA clones, cDNA clones from the breast subtraction described above were randomly picked and colony PCR amplified. Their mRNA expression levels in breast tumor, normal breast and various other normal tissues were determined using microarray technology (Synteni, Palo Alto, Calif.). Briefly, the PCR amplification products were arrayed onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. Data was analyzed using Synteni provided GEMTOOLS Software. Of the seventeen cDNA clones examined, those of SEQ ID NO: 40, 46, 59 and 73 were found to be over-expressed in breast tumor and expressed at low levels in all normal tissues tested (breast, BMC, colon, fetal tissue, salivary gland, bone marrow, lung, pancreas, large intestine, spinal cord, adrenal gland, kidney, pancreas, liver, stomach, skeletal muscle, heart, small intestine, skin, brain and human mammary epithelial cells). The clones of SEQ ID NO: 41 and 48 were found to be over-expressed in breast tumor and expressed at low levels in all other tissues tested, with the exception of bone marrow. The clone of SEQ ID NO: 42 was found to be over-expressed in breast tumor and expressed at low levels in all other tissues tested except bone marrow and spinal cord. The clone of SEQ ID NO: 43 was found to be over-expressed in breast tumor and expressed at low levels in all other tissues tested with the exception of spinal cord, heart and small intestine. The clone of SEQ ID NO: 51 was found to be over-expressed in breast tumor and expressed at low levels in all other tissues tested with the exception of large intestine. The clone of SEQ ID NO: 54 was found to be over-expressed in breast tumor and expressed at low levels in all other tissues tested with the exception of PBMC, stomach and small intestine. The clone of SEQ ID NO: 56 was found to be over-expressed in breast tumor and expressed at low levels in all other tissues tested with the exception of large and small intestine, human mammary epithelia cells and SCID mouse-passaged breast tumor. The clone of SEQ ID NO: 60 was found to be over-expressed in breast tumor and expressed at low levels in all other tissues tested with the exception of spinal cord and heart. The clone of SEQ ID NO: 61 was found to be over-expressed in breast tumor and expressed at low levels in all other tissues tested with the exception of small intestine. The clone of SEQ ID NO: 72 was found to be over-expressed in breast tumor and expressed at low levels in all other tissues tested with the exception of colon and salivary gland.

The results of a Northern blot analysis of the clone SYN18C6 (SEQ ID NO: 40) are shown in FIG. 1. A predicted protein sequence encoded by SYN18C6 is provided in SEQ ID NO: 62.

Additional cDNA clones that are over-expressed in breast tumor tissue were isolated from breast cDNA subtraction libraries as follows. Breast subtraction libraries were prepared, as described above, by PCR-based subtraction employing pools of breast tumor cDNA as the tester and pools of either normal breast cDNA or cDNA from other normal tissues as the driver. cDNA clones from breast subtraction were randomly picked and colony PCR amplified and their mRNA expression levels in breast tumor, normal breast and various other normal tissues were determined using the microarray technology described above. Twenty-four distinct cDNA clones were found to be over-expressed in breast tumor and expressed at low levels in all normal tissues tested (breast, brain, liver, pancreas, lung, salivary gland, stomach, colon, kidney, bone marrow, skeletal muscle, PBMC, heart, small intestine, adrenal gland, spinal cord, large intestine and skin). The determined partial cDNA sequences for these clones are provided in SEQ ID NO: 63–87. Comparison of the sequences of SEQ ID NO: 74–87 with those in the gene bank as described above, revealed homology to previously identified human genes. No significant homologies were found to the sequences of SEQ ID NO: 63–73.

Three DNA isoforms for the clone B726P (partial sequence provided in SEQ ID NO: 71 were isolated as follows. A radioactive probe was synthesized from B726P by excising B726P DNA from a pT7Blue vector (Novagen) by a BamHI/XbaI restriction digest and using the resulting DNA as the template in a single-stranded PCR in the presence of [α-32P]dCTP. The sequence of the primer employed for this PCR is provided in SEQ ID NO: 177. The resulting radioactive probe was used to probe a directional cDNA library and a random-primed cDNA library made using RNA isolated from breast tumors. Eighty-five clones were identified, excised, purified and sequenced. Of these 85 clones, three were found to each contain a significant open reading frame. The determined cDNA sequence of the isoform B726P-20 is provided in SEQ ID NO: 175, with the corresponding predicted amino acid sequence being provided in SEQ ID NO: 176. The determined cDNA sequence of the isoform B726P-74 is provided in SEQ ID NO: 178, with the corresponding predicted amino acid sequence being provided in SEQ ID NO: 179. The determined cDNA sequence of the isoform B726P-79 is provided in SEQ ID NO: 180, with the corresponding predicted amino acid sequence being provided in SEQ ID NO: 181.

Further isolation of individual clones that are over-expressed in breast tumor tissue was conducted using cDNA subtraction library techniques described above. In particular, a cDNA subtraction library containing cDNA from breast tumors subtracted with five other normal human tissue cDNAs (brain, liver, PBMC, pancreas and normal breast) was utilized in this screening. From the original subtraction, one hundred seventy seven clones were selected to be further characterized by DNA sequencing and microarray analysis. Microarray analysis demonstrated that the sequences in SEQ ID NO: 182–251 were 2 or more fold over-expressed in human breast tumor tissues over normal human tissues. No significant homologies were found for nineteen of these clones, including, SEQ ID NO: 185, 186, 194, 199, 205, 208, 211, 214–216, 219, 222, 226, 232, 236, 240, 241, 245 and 246, with the exception of some previously identified expressed sequence tags (ESTs). The remaining clones share some homology to previously identified genes, specifically SEQ ID NO: 181–184, 187–193, 195–198, 200–204, 206, 207, 209, 210, 212, 213, 217, 218, 220, 221, 223–225, 227–231, 233–235, 237–239, 242–244 and 247–251.

Of the seventy clones showing over-expression in breast tumor tissues, fifteen demonstrated particularly good expression levels in breast tumor over normal human tissues. The following eleven clones did not show any significant homology to any known genes. Clone 19463.1 (SEQ ID NO: 185) was over-expressed in the majority of breast tumors and also in the SCID breast tumors tested (refer to Example 2); additionally, over-expression was found in a majority of normal breast tissues. Clone 19483.1 (SEQ ID NO: 216) was over-expressed in a few breast tumors, with no over-expression in any normal tissues tested. Clone 19470.1 (SEQ ID NO: 219) was found to be slightly over-expressed in some breast tumors. Clone 19468.1 (SEQ ID NO: 222) was found to be slightly over-expressed in the majority of breast tumors tested. Clone 19505.1 (SEQ ID NO: 226) was found to be slightly over-expressed in 50% of breast tumors, as well as in SCID tumor tissues, with some degree of over-expression in found in normal breast. Clone 1509.1 (SEQ ID NO: 232) was found to be over-expressed in very few breast tumors, but with a certain degree of over-expression in metastatic breast tumor tissues, as well as no significant over-expression found in normal tissues. Clone 19513.1 (SEQ ID NO: 236) was shown to be slightly over-expressed in few breast tumors, with no significant over-expression levels found in normal tissues. Clone 19575.1 (SEQ ID NO: 240) showed low level over-expression in some breast tumors and also in normal breast. Clone 19560.1 (SEQ ID NO: 241) was over-expressed in 50% of breast tumors tested, as well as in some normal breast tissues. Clone 19583.1 (SEQ ID NO: 245) was slightly over-expressed in some breast tumors, with very low levels of over-expression found in normal tissues. Clone 19587.1 (SEQ ID NO: 246) showed low level over-expression in some breast tumors and no significant over-expression in normal tissues.

Clone 19520.1 (SEQ ID NO: 233), showing homology to clone 102D24 on chromosome 11q3.31, was found to be over-expressed in breast tumors and in SCID tumors. Clone 19517.1 (SEQ ID NO: 237), showing homology to human PAC 128M19 clone, was found to be slightly over-expressed in the majority of breast tumors tested. Clone 19392.2 (SEQ ID NO: 247), showing homology to human chromosome 17, was shown to be over-expressed in 50% of breast tumors tested. Clone 19399.2 (SEQ ID NO: 250), showing homology to human Xp22 BAC GSHB-184P14, was shown to be slightly over-expressed in a limited number of breast tumors tested.

Example 2

Isolation and Characterization of Breast Tumor Polypeptides Obtained by PCR-Based Subtracting Using SCID-Passaged Tumor RNA Human breast tumor antigens were obtained by PCR-based subtraction using SCID mouse passaged breast tumor RNA as follows. Human breast tumor was implanted in SCID mice and harvested on the first or sixth serial passage, as described in patent application Ser. No. 08/556,659 filed Nov. 13, 1995, U.S. Pat. No. 5,986,170. Genes found to be differentially expressed between early and late passage SCID tumor may be stage specific and therefore useful in therapeutic and diagnostic applications. Total RNA was prepared from snap frozen SCID passaged human breast tumor from both the first and sixth passage.

PCR-based subtraction was performed essentially as described above. In the first subtraction (referred to as T9), RNA from first passage tumor was subtracted from sixth passage tumor RNA to identify more aggressive, later passage-specific antigens. Of the 64 clones isolated and sequenced from this subtraction, no significant homologies were found to 30 of these clones, hereinafter referred to as: 13053, 13057, 13059, 13065, 13067, 13068, 13071–13073, 13075, 13078, 13079, 13081, 13082, 13092, 13097, 13101, 13102, 13131, 13133, 13119, 13135, 13139, 13140, 13146–13149, and 13151, with the exception of some previously identified expressed sequence tags (ESTs). The determined cDNA sequences for these clones are provided in SEQ ID NO: 88–116, respectively. The isolated cDNA sequences of SEQ ID NO: 117–140 showed homology to known genes.

In a second PCR-based subtraction, RNA from sixth passage tumor was subtracted from first passage tumor RNA to identify antigens down-regulated over multiple passages. Of the 36 clones isolated and sequenced, no significant homologies were found to nineteen of these clones, hereinafter referred to as: 14376, 14377, 14383, 14384, 14387, 14392, 14394, 14398, 14401, 14402, 14405, 14409, 14412, 14414–14416, 14419, 14426, and 14427, with the exception of some previously identified expressed sequence tags (ESTs). The determined cDNA sequences for these clones are provided in SEQ ID NO: 141–159, respectively. The isolated cDNA sequences of SEQ ID NO: 160–174 were found to show homology to previously known genes.

Further analysis of human breast tumor antigens through PCR-based subtraction using first and sixth passage SCID tumor RNA was performed. Sixty three clones were found to be differentially expressed by a two or more fold margin, as determined by microarray analysis, i.e., higher expression in early passage tumor over late passage tumor, or vice versa. Seventeen of these clones showed no significant homology to any known genes, although some degree of homology with previously identified expressed sequence tags (ESTs) was found, hereinafter referred to as 20266, 20270, 20274, 20276, 20277, 20280, 20281, 20294, 20303, 20310, 20336, 20341, 20941, 20954, 20961, 20965 and 20975 (SEQ ID NO: 252–268, respectively). The remaining clones were found to share some degree of homology to known genes, which are described in the Brief Description of the Drawings and Sequence Identifiers section above, hereinafter referred to as 20261, 20262, 20265, 20267, 20268, 20271, 20272, 20273, 20278, 20279, 20293, 20300, 20305, 20306, 20307, 20313, 20317, 20318, 20320, 20321, 20322, 20326, 20333, 20335, 20337, 20338, 20340, 20938, 20939, 20940, 20942, 20943, 20944, 20946, 20947, 20948, 20949, 20950, 20951, 20952, 20957, 20959, 20966, 20976, 20977 and 20978. The determined cDNA sequences for these clones are provided in SEQ ID NO: 269–313, respectively.

Example 3

Synthesis of Polypeptides

Polypeptides may be synthesized on an Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

From the foregoing, it will be appreciated that, although specific embodiments of the invention have been described herein for the purposes of illustration, various modifications may be made without deviating from the spirit and scope of the invention.

What is claimed is:

1. A isolated polynucleotide consisting of SEQ ID NO:40.

2. An isolated polynucleotide comprising SEQ ID NO:175.

3. An isolated polynucleotide comprising SEQ ID NO:178.

4. An isolated polynucleotide consisting of SEQ ID NO:180.

5. An isolated polynucleotide comprising a sequence selected from the group consisting of sequences having at least 90% identity to SEQ ID NO:175, wherein the polynucleotide can be used to detect expression of the polynucleotide set forth in SEQ ID NO:175 in a biological sample.

6. An isolated polynucleotide comprising a sequence selected from the group consisting of sequences having at least 90% identity to SEQ ID NO:178, wherein the polynucleotide can be used to detect expression of the polynucleotide set forth in SEQ ID NO:178 in a biological sample.

7. An isolated polynucleotide consisting of a sequence selected from the group consisting of sequences having at least 90% identity to SEQ ID NO:180, wherein the polynucleotide can be used to detect expression of the polynucleotide set forth in SEQ ID NO:180 in a biological sample.

8. An expression vector comprising a polynucleotide according to any one of claims 1–7.

9. A host cell transformed with the expression vector of claim 8.

10. The host cell of claim 9 wherein the host cell is selected from the group consisting of *E coli*, yeast and mammalian cell lines.

* * * * *